(12) United States Patent
Nakae

(10) Patent No.: US 11,779,269 B2
(45) Date of Patent: Oct. 10, 2023

(54) PAIN ESTIMATING DEVICE, PAIN ESTIMATING METHOD, AND PAIN CLASSIFICATION

(71) Applicant: Osaka University, Osaka (JP)

(72) Inventor: Aya Nakae, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 858 days.

(21) Appl. No.: 16/374,002

(22) Filed: Apr. 3, 2019

(65) Prior Publication Data
US 2019/0239801 A1    Aug. 8, 2019

Related U.S. Application Data

(62) Division of application No. 16/326,789, filed as application No. PCT/JP2017/029991 on Aug. 22, 2017.

(30) Foreign Application Priority Data

Aug. 22, 2016   (JP) .................................. 2016-162195
Jul. 7, 2017    (JP) .................................. 2017-133424

(51) Int. Cl.
A61B 5/00      (2006.01)
A61B 5/316     (2021.01)
(Continued)

(52) U.S. Cl.
CPC ............ *A61B 5/4824* (2013.01); *A61B 5/316* (2021.01); *A61B 5/369* (2021.01); *A61B 5/377* (2021.01);
(Continued)

(58) Field of Classification Search
CPC ....... A61B 5/4826; A61B 5/316; A61B 5/369; A61B 5/377; A61B 5/7264; A61B 5/4824;
(Continued)

(56) References Cited

U.S. PATENT DOCUMENTS 9,402,558 B2    8/2016  John et al.
2003/0100931 A1  5/2003  Mullett
(Continued)

FOREIGN PATENT DOCUMENTS

CN   101677775 A   3/2010
CN   103405225 A   8/2016
(Continued)

OTHER PUBLICATIONS

Granovsky, Yelena, et al. "Objective correlate of subjective pain perception by contact heat-evoked potentials." The Journal of Pain 9.1 (2008): 53-63. IDS filed Jul. 15, 2019 (Year: 2008).*
(Continued)

*Primary Examiner* — Puya Agahi
(74) *Attorney, Agent, or Firm* — Muncy, Geissler, Olds & Lowe, P.C.

(57) ABSTRACT

Provided is a pain estimating device with which it is possible to estimate objectively and accurately pain being experienced by a subject. A pain estimating device 110 estimates the magnitude of pain being experienced by a subject, on the basis of brainwaves of the subject, and is provided with: a measurement unit 111 which acquires a plurality of items of brainwave data or analysis data thereof by measuring brainwaves from the subject a plurality of times; and an estimation unit 112 which estimates the relative magnitude of the pain being experienced when the brainwave measurements were conducted a plurality of times, from the plurality of items of brainwave data or the analysis data thereof (for example the amplitude), on the basis of the linearity of a relationship between the brainwave data or the analysis data thereof (for example the amplitude) and the pain. The present invention also provides a pain estimating method and device with which it is possible to estimate objectively and accurately pain being experienced by a subject, and to
(Continued)

classify simply the quality and quantity thereof. The present invention also provides a method for generating a pain classification value for classifying pain being experienced by the subject, on the basis of brainwaves of the subject.

4 Claims, 24 Drawing Sheets

(51) Int. Cl.
*A61B 5/369* (2021.01)
*A61B 5/377* (2021.01)
(52) U.S. Cl.
CPC ........ *A61B 5/7264* (2013.01); *G06F 2218/14* (2023.01)
(58) Field of Classification Search
CPC ....... A61B 5/483; A61B 5/4064; A61B 5/372; A61B 5/163; G06K 9/00543
See application file for complete search history.

(56) References Cited

U.S. PATENT DOCUMENTS

| | | | |
|---|---|---|---|
| 2008/0249430 A1 | 10/2008 | Hiesiger et al. | |
| 2013/0310660 A1* | 11/2013 | Zuckerman-Stark | .... A61B 5/24 600/301 |
| 2014/0148657 A1* | 5/2014 | Hendler | ................. A61B 5/291 600/545 |
| 2014/0276188 A1 | 9/2014 | Jardin | |
| 2016/0081575 A1* | 3/2016 | Wu | ....................... A63F 13/332 600/301 |
| 2018/0242904 A1* | 8/2018 | Nakae | ..................... A61B 5/377 |
| 2018/0310851 A1* | 11/2018 | Das | ...................... A61B 5/7203 |
| 2019/0223783 A1 | 7/2019 | Nakae | |

FOREIGN PATENT DOCUMENTS

| | | |
|---|---|---|
| CN | 103405225 B | 8/2016 |
| JP | 2010523226 A | 7/2010 |
| JP | 2013523274 A | 6/2013 |
| JP | 2016162195 A | 9/2016 |
| JP | 2017133424 A | 8/2017 |
| WO | 2008124566 A2 | 10/2008 |
| WO | 2013140106 A1 | 9/2013 |
| WO | 2016049041 A1 | 3/2016 |
| WO | 2016125158 A1 | 8/2016 |
| WO | 2018038121 A1 | 3/2018 |

OTHER PUBLICATIONS

Johnstone, Tom, Tim V. Salomons, and Richard J. Davidson. "Turning on the alarm: the neural mechanisms of the transition from innocuous to painful sensation." Neuroimage 59.2 (2012): 1594-1601. (Year: 2012).*

Partial English translation of Office Action issued in Japanese Application No. 2019-208786 dated Mar. 30, 2021, 5 pages.
English translation of Final Office Action issued in Japanese counterpart Application No. 2019-208786, dated Nov. Sep. 29, 2021, 5 pages.
English translation of second Office Action issued in Chinese counterpart Application No. 201780064224.0, dated Oct. 9, 2021, 12 pages.
Summons to attend Oral Proceedings pursuant to Rule 115(1) EPC dated Nov. 22, 2021, issued in the counterpart European Application No. 17843599.6, 5 pages.
Research on Objective Detection Method of Current Sensory Threshold based on EEG, Yi Qiu, Chinese Master's Theses Full-text Database, Medicine and Health Sciences, Issue 3, published on Mar. 15, 2012, pp. 1-65.
Aoki (Nov. 16, 1995) "EEG fluctuation at the time of pain sensation," IEICE technical report—ME and bio cybernetics. 95(356):71-78.
Granovsky et al. (Jan. 2008) "Objective correlate of subjective pain perception by contact heat-evoked potentials," The journal of pain: official journal of the American Pain Society. 9(1):53-63.
Huang et al. (Nov. 1, 2013) "A novel approach to predict subjective pain perception from single-trial laser-evoked potentials," Neuroimage. 81:283-293.
Yoneda (Nov. 17, 1998) "Measurement of event-related potentials for electrical novel stimuli that induce pain," IEICE technical report—ME and bio cybernetics. 98(400):7-12.
Japanese Patent Application No. 2016-162195, by Osaka University, filed Aug. 22, 2016, 30 pages.
Japanese Patent Application No. 2017-133424, by Osaka University, filed Jul. 7, 2017, 57 pages.
Non-Final Office Action issued in U.S. counterpart U.S. Appl. No. 16/326,789, dated Dec. 8, 2021, 51 pages.
Wager T.D. et al., "Placebo effects in laser-evoked pain potentials", Brain, Behavior, and Immunity, vol. 20, Issue 3, May 2006, 219-230.
European Search Report for Application No. 17843599.6 dated Apr. 2, 2020 (11 pages).
Communication pursuant to Rules 70(2) and 70a(2) EPC dated Apr. 21, 2020, received in EP Application No. 17843599.6 (1 page).
English translation of Office Action issued in Chinese Application No. 201780064224.0, dated Mar. 26, 2021, 7 pages.
Partial English translation of Office Action issued in Japanese Application No. 2019-208786 dated Mar. 25, 2021, 5 pages.
Communication pursuant to Article 94(3) EPC issued in the European Application 17843599.6-1113 dated Feb. 9, 2021, 4 pages.
Huishi Zhang Clara et al: "Spectral and spatial changes of brain rhythmic activity in response to the sustained thermal pain stimulation: EEG Imaging of Tonic Thermal Pain", Human Brain Mapping, Aug. 1, 2016, pp. 2976-2991, vol. 37, No. 8, XP055904572.
Iannetti G D et al: "Operculoinsular cortex encodes pain intensity at the earliest stages of cortical processing as indicated by amplitude of laser-evoked potentials in humans", Neuroscience, Jan. 1, 2005, pp. 199-208, vol. 131, No. 1, New York, NY, US, XP027844491.

* cited by examiner

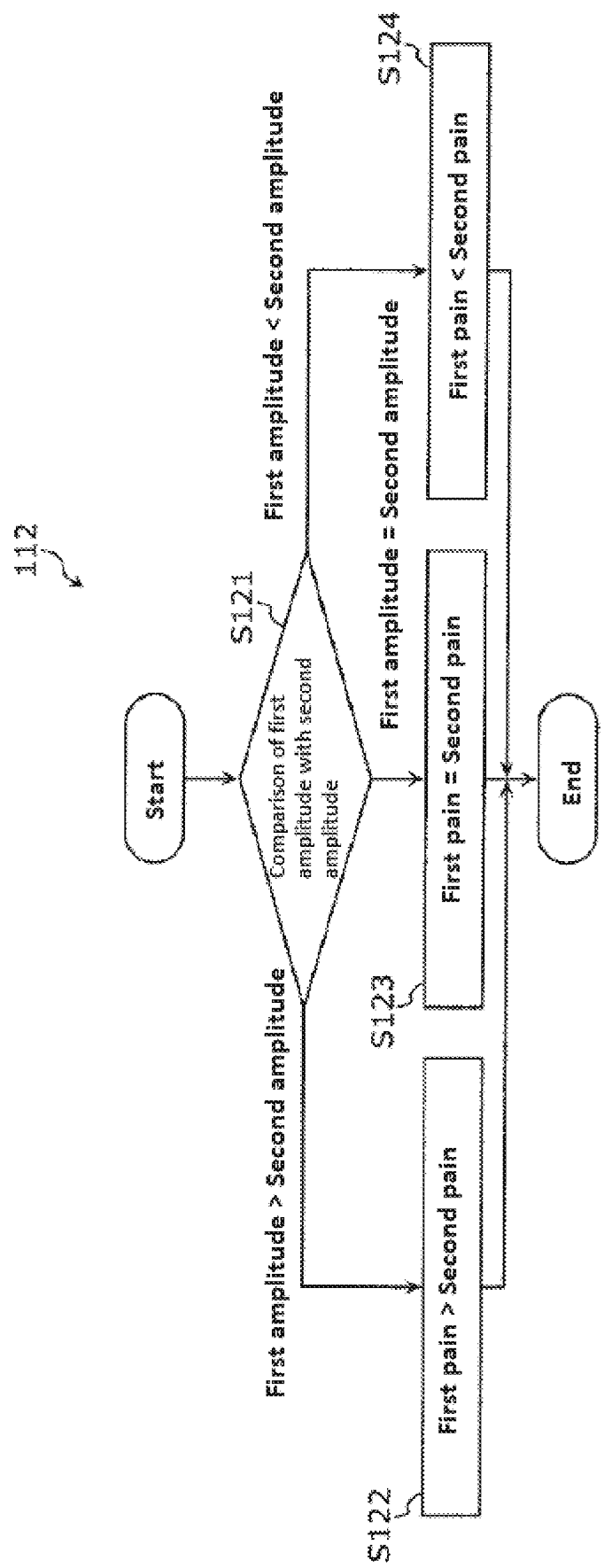

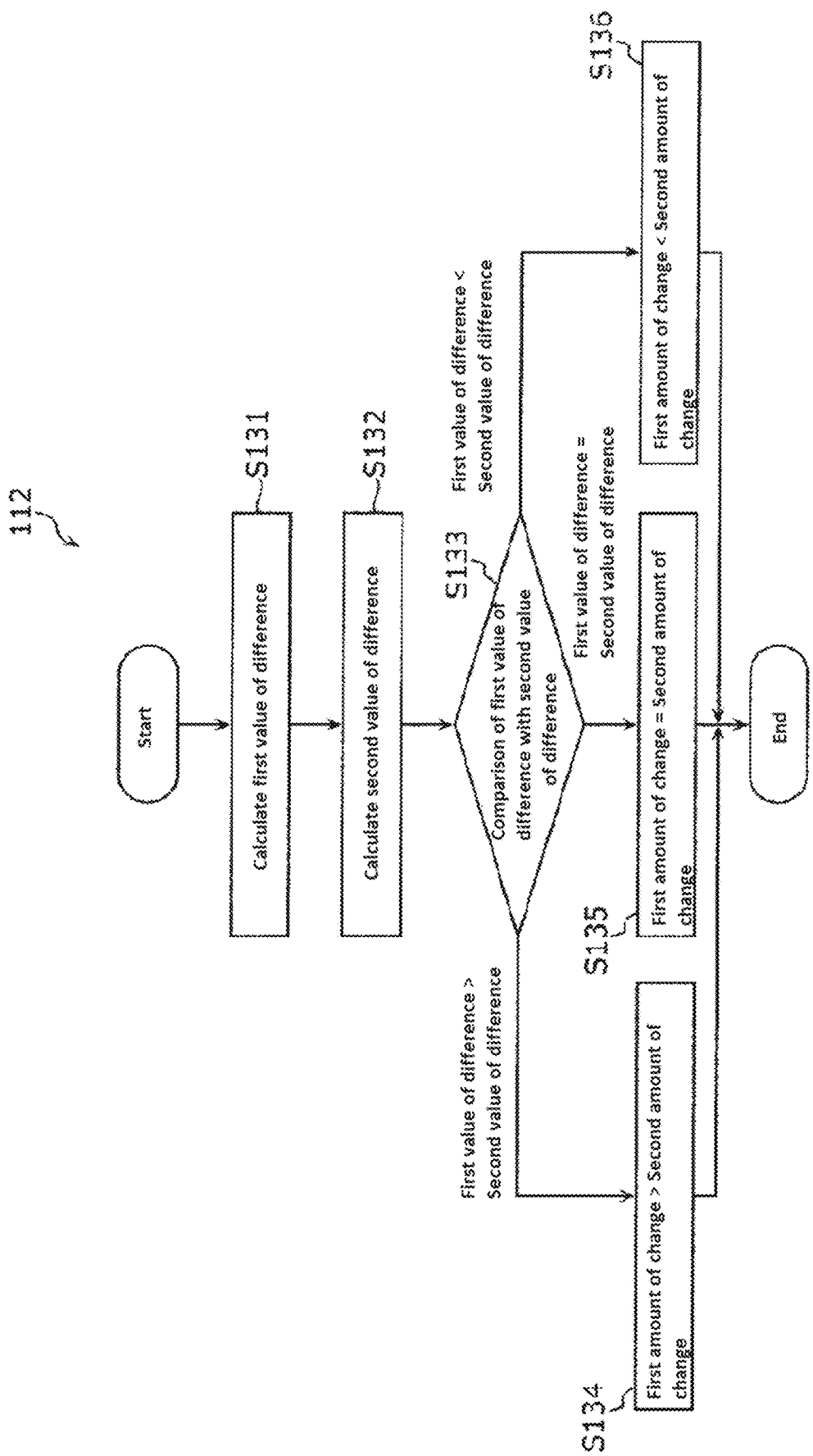

FIG.27
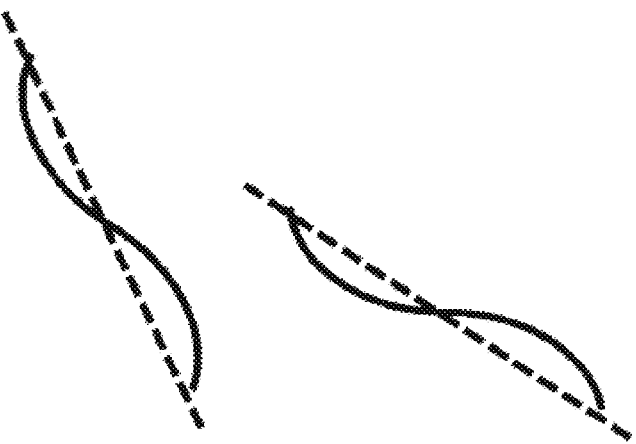
A Sigmoid function
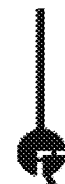
B Individual differences in pain response and pain reaction prediction using linear function approximation
Differences in slopes
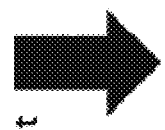
Modulation start point
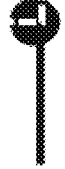
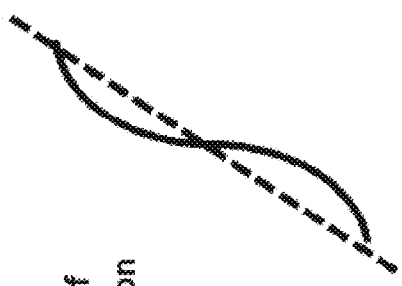
Linear function approximation of modulation region

PAIN ESTIMATING DEVICE, PAIN ESTIMATING METHOD, AND PAIN CLASSIFICATION

CROSS-REFERENCE TO RELATED APPLICATIONS

This application is a divisional application being filed under 35 U.S.C. § 120, of U.S. National Stage application Ser. No. 16/326,789, filed on Feb. 20, 2019 under 35 U.S.C. § 371, of International Patent Application No. PCT/JP2017/029991, filed Aug. 22, 2017, which claims the benefit of and priority under 35 U.S.C. § 119 to Japanese Patent Application Nos. 2016-162195, filed Aug. 22, 2016, and 2017-133424, filed on Jul. 7, 2017 the contents of each of which is incorporated herein by reference in their entirety.

TECHNICAL FIELD

The present invention relates to a pain estimation apparatus and a pain estimation method for estimating the magnitude of pain of an object being estimated based on a brainwave of the object being estimated. The present invention also relates to applying a biological signal such as a brainwave obtained from an object being estimated to a pain function (e.g., linear function with a linear approximation of the modulation range, or a more comprehensive sigmoid function encompassing the same) and classifying the quality and amount of pain using a characteristic value obtained thereby. More specifically, the present invention relates to objectively showing a pain level (e.g., weak pain, strong pain, or the like), which varies by individual, from a signal value.

BACKGROUND ART

Pain is intrinsically subjective, but objective evaluation is desirable for therapy. Patients often suffer from an adverse experience by underestimating pain. In this regard, a method for objectively estimating pain using a brainwave has been proposed (see, for example, Patent Literature 1).

However, the intensity of pain is subjective, such that objective evaluation is challenging. Whether the pain is particularly unbearable or tolerable to a certain extent cannot be expressed only by a subjective opinion of "painful". The expression also varies by individual, such that objective evaluation is challenging. While classification of pain is desirable for observing therapeutic effects, such a technology has not been provided.

CITATION LIST

Patent Literature

[PTL 1] Japanese National Phase PCT Laid-open Publication No. 2010-523226

SUMMARY OF INVENTION

Solution to Problem

The present invention has solved the problem of being unable to accurately estimate pain, when using data indicating brainwave activity of multipole individuals in a plurality of pain as reference data, by using a pain function (e.g., linear function with a linear approximation of the modulation range, or a more comprehensive sigmoid function encompassing the same).

In other words, the present invention provides a pain estimation apparatus that can objectively and accurately estimate pain of an object being estimated.

The present invention also provides a pain estimation method and apparatus that can objectively and accurately estimate pain of an object being estimated and readily classify the quality and amount thereof. The present invention also provides a technology for generating a pain classifier for such pain classification.

A pain estimation apparatus according to one embodiment of the invention is a pain estimation apparatus for estimating a magnitude of pain of an object being estimated based on a brainwave of the object being estimated, comprising: a measurement unit for obtaining a plurality of brainwave data or analysis data thereof (including, for example, amplitude) by measuring a brainwave a plurality of times from the object being estimated; and an estimation unit for estimating a relative magnitude of pain upon the measurement of brainwave a plurality of times from the plurality of brainwave data or analysis data thereof (including, for example, amplitude) based on a pain function (where examples of pain function patterns include linear and non-linear patterns, so that the function can be based on linearity) for the relationship between the brainwave data or analysis data thereof (e.g., amplitude) and pain. Linearity can be a value other than amplitude such as a frequency or wavelet processing value, as long as the value is a characteristic amount of a brainwave. Linearity in a modulation range is found not only in the characteristic amount of a brainwave, but also in subjective evaluation.

This configuration can estimate the relative magnitude of pain upon measurements of a brainwave a plurality of times from a plurality of brainwave data or analysis data thereof (including, for example, amplitude) based on linearity in the relationship between the brainwave or analysis data thereof (including, for example, amplitude) and pain. Existence of linearity between brainwave or analysis data thereof (including, for example, amplitude) and pain is a phenomenon elucidated by the inventor. The magnitude of pain can be estimated without using the magnitude of pain declared by the object being estimated by utilizing the linearity in the relationship between brainwave or analysis data thereof (including, for example, amplitude) and pain, so that pain of the object being estimated can be objectively and accurately estimated. Furthermore, brainwave data does not need to be collected in advance from the object being estimated or the like, such that the magnitude of pain can be more readily estimated.

For example, the plurality of brainwave data comprise first brainwave data and second brainwave data, and the estimation unit can (i) estimate that first pain corresponding to the first brainwave data or analysis data thereof (including, for example, amplitude) is greater than second pain corresponding to the second brainwave data or analysis data thereof (including, for example, amplitude) if the first brainwave data is greater than the second brainwave data, and (ii) estimate that the first pain is less than the second pain if the first brainwave data or analysis data thereof (including, for example, amplitude) is less than the second brainwave data or analysis data thereof (including, for example, amplitude).

This configuration can compare the first brainwave data or analysis data thereof (including, for example, amplitude) with the second brainwave data or analysis data thereof (including, for example, amplitude) to estimate which pain is greater between the first pain corresponding to the first brainwave data or analysis data thereof and the second brainwave data or analysis data thereof (including, for example, amplitude). For example, the magnitude of pain before and after therapy can therefore be compared to evaluate a therapeutic effect by measuring brainwave data or analysis data thereof (including, for example, amplitude) before and after therapy.

For example, the plurality of brainwave data or analysis data thereof (including, for example, amplitude) further comprise third brainwave data or analysis data thereof and fourth brainwave data or analysis data thereof (including, for example, amplitude). The estimation unit can further estimate a relative amount of change between a first change from the first pain to the second pain and a second change from third pain corresponding to the third brainwave data or analysis data thereof (including, for example, amplitude) to fourth pain corresponding to the fourth brainwave data or analysis data thereof (including, for example, amplitude), based on a first value of difference between the first brainwave data or analysis data thereof (including, for example, amplitude) and the second brainwave data or analysis data thereof (including, for example, amplitude) and a second value of difference between the third brainwave data or analysis data thereof (including, for example, amplitude) and the fourth brainwave data or analysis data thereof (including, for example, amplitude).

This configuration can compare the value of difference in data such as a pair of amplitudes of two sets of brainwave data or analysis data thereof to estimate the relative amount of change in pain. For example, a change in pain due to first therapy can therefore be compared to a change in pain due to second therapy to evaluate the relative effect of the first therapy and the second therapy.

A pain estimation apparatus according to another embodiment of the invention is a pain estimation apparatus for estimating a magnitude of pain of an object being estimated based on a brainwave of the object being estimated, comprising: a measurement unit for obtaining brainwave data corresponding to stimulation of each magnitude by measuring a brainwave from the object being estimated sequentially inflicted with stimulation of a plurality of magnitudes; and an identification unit for identifying an upper limit value and a lower limit value of brainwave or analysis data thereof (including, for example, amplitude) of the object being estimated, wherein the measurement unit further measures a brainwave from the object being estimated to obtain object's brainwave data, and the pain estimation apparatus further comprises an estimation unit for estimating a value of the magnitude of pain corresponding to the object's brainwave data based on a relative magnitude of the object's brainwave data or analysis data thereof (including, for example, amplitude) with respect to the upper limit value and the lower limit value.

This configuration can estimate a value of magnitude of pain corresponding to the object's brainwave data based on the relative magnitude of object's brainwave data or analysis data thereof (including, for example, amplitude) with respect to the upper limit value and lower limit value of brainwave of the object being estimated or analysis data thereof (including, for example, amplitude), such that the magnitude of pain can be quantified. Neither identification of the upper limit value and the lower limit value nor estimation of a value of the magnitude of pain requires the use of the magnitude of pain declared by the object being estimated. Thus, pain of the object being estimated can be objectively estimated.

For example, the estimation unit can also estimate a ratio of a value of difference between the object's brainwave data or analysis data thereof (including, for example, amplitude) and the lower limit value to a value of difference between the upper limit value and the lower limit value as a value of the magnitude of pain.

This configuration can estimate the value of the magnitude of pain by using a ratio of a value of difference between object's brainwave data or analysis data thereof (including, for example, amplitude) and the lower limit value to a value of difference between the upper limit value and the lower limit value. Therefore, a value of the magnitude of pain can be estimated more readily.

These comprehensive or specific embodiments can be materialized with a system, method, integrated circuit, computer program, or a storage medium such as a computer readable CD-ROM or any combination of a system, method, integrated circuit, computer program and storage medium.

The present invention also provides the following.

(A1) A pain estimation apparatus for estimating a magnitude of pain of an object being estimated based on a brainwave of the object being estimated, comprising:
 a measurement unit for measuring a brainwave a plurality of times from the object being estimated to obtain a plurality of brainwave data or analysis data thereof; and
 an estimation unit for estimating a relative magnitude of pain upon the measurement of a brainwave a plurality of times from the plurality of brainwave data or analysis data thereof, based on a pain function for a relationship between brainwave data or analysis data thereof and pain.

(A2) The pain estimation apparatus of item A1,
 wherein the plurality of brainwave data or analysis data thereof comprise first brainwave data or analysis data thereof and second brainwave data or analysis data thereof,
 wherein the estimation unit
 (i) estimates that first pain corresponding to the first brainwave data or analysis data thereof is greater than second pain corresponding to the second brainwave data or analysis data thereof if the first brainwave data is greater than the second brainwave data, and
 (ii) estimates that the first pain is less than the second pain if the first brainwave data or analysis data thereof is less than the second brainwave data or analysis data thereof.

(A3) The pain estimation apparatus of item A1 or A2,
 wherein the plurality of brainwave data or analysis data thereof further comprise third brainwave data or analysis data thereof and fourth brainwave data or analysis data thereof,
 wherein the estimation unit further estimates a relative amount of change between a first change from the first pain to the second pain and a second change from third pain corresponding to the third brainwave data to fourth pain corresponding to the fourth brainwave data, based on a first value of difference between the first brainwave data or analysis data thereof and the second brainwave data or analysis data thereof and a second value of difference between the third brainwave data or analysis data thereof and the fourth brainwave data or analysis data thereof.

(A4) The apparatus of any one of items A1 to A3, further comprising:
 a pain classifier generation unit for fitting the pain and the brainwave data or analysis data thereof to a pain function to obtain a pain function specific to the object being estimated, and identifying a pain classifier for separating a pain level to at least two based on the pain function; and a pain classification unit for classifying a pain level of the object being estimated by fitting the brainwave data or analysis data thereof to the pain classifier.

(A5) The apparatus of any one of items A1 to A4, wherein the brainwave data or analysis data thereof is an amplitude of a brainwave.

(A6) The apparatus of item A4 or A5, wherein the pain function comprises a linear function or a sigmoid function (e.g., a linear function with a linear approximation of a modulation range, or a more comprehensive sigmoid function encompassing the same).

(A6A) The apparatus of any one of items A1 to A6, wherein the estimation being based on the pain function comprises being based on a pain function pattern including linearity or non-linearity and preferably being based on linearity.

(A7) A pain estimation method for estimating a magnitude of pain of an object being estimated based on a brainwave of the object being estimated, comprising:
a measurement step for measuring a brainwave a plurality of times from the object being estimated to obtain a plurality of brainwave data or analysis data thereof; and
an estimation step for estimating a relative magnitude of pain upon the measurement of a brainwave a plurality of times from the plurality of brainwave data or analysis data thereof based on a pain function for a relationship between brainwave data or analysis data thereof and pain.

(A8) The method of item A7, wherein the brainwave data or analysis data thereof is an amplitude of a brainwave.

(A9) The method of item A7 or A8, wherein the estimation step comprises classifying a pain level of the object being estimated by fitting the brainwave data or analysis data thereof to a predetermined pain function, and the pain classifier is obtained by fitting the brainwave data or analysis data thereof of the object being estimated to a pain function curve.

(A10) The method of item A9, wherein the pain function comprises a linear function or a sigmoid function (e.g., a linear function with a linear approximation of a modulation range, or a more comprehensive sigmoid function encompassing the same).

(A10A) The method of any one of items A7 to A10, further comprising one or more features of items A1 to A6 and A6A.

(A11) A program for implementing a pain estimation method for estimating a magnitude of pain of an object being estimated based on a brainwave of the object being estimated on a computer, the method comprising:
a measurement step for measuring a brainwave a plurality of times from the object being estimated to obtain a plurality of brainwave data or analysis data thereof; and
an estimation step for estimating a relative magnitude of pain upon the measurement of a brainwave a plurality of times from the plurality of brainwave data or analysis data thereof based on a pain function for a relationship between brainwave data or analysis data thereof and pain.

(A11A) The program of item A11, further comprising one or more features of items A1 to A6, A6A, A7 to A10, and A10A.

(A12) A storage medium for storing a program implementing a pain estimation method for estimating a magnitude of pain of an object being estimated based on a brainwave of the object being estimated on a computer, the method comprising:
a measurement step for measuring a brainwave a plurality of times from the object being estimated to obtain a plurality of brainwave data or analysis data thereof; and
an estimation step for estimating a relative magnitude of pain upon the measurement of a brainwave a plurality of times from amplitudes of the plurality of brainwave data based on a pain function for a relationship between brainwave data or analysis data thereof and pain.

(A12A) The storage medium of item A12, further comprising one or more features of items A1 to A6, A6A, A7 to A10, A10A, A11, and A11A.

(A13) A pain estimation apparatus for estimating a magnitude of pain of an object being estimated based on a brainwave of the object being estimated, comprising: a measurement unit for measuring a brainwave from an object being estimated sequentially inflicted with stimulation of a plurality of magnitudes to obtain brainwave data or analysis data thereof corresponding to stimulation of each magnitude; and
an identification unit for identifying an upper limit value and a lower limit value of the brainwave data or analysis data thereof of the object being estimated based on the brainwave data or analysis data thereof,
wherein the measurement unit further measures a brainwave from the object being estimated to obtain object's brainwave data or analysis data thereof, and wherein the pain estimation apparatus further comprises an estimation unit for estimating a value of a magnitude of pain corresponding to the object's brainwave data or analysis data thereof based on a relative size of a value of the object's brainwave data or analysis data thereof with respect to the upper limit value and the lower limit value.

(A14) The pain estimation apparatus of item A13,
wherein the estimation unit estimates a ratio of a value of difference between a value of the object's brainwave data or analysis data thereof and the lower limit value to a value of difference between the upper limit value and the lower limit value as the value of the magnitude of pain.

(A15) The apparatus of item A13 or A14, further comprising:
a pain classifier generation unit for fitting the pain and the brainwave data or analysis data thereof to a pain function to obtain a pain function specific to the object being estimated, and identifying a pain classifier for separating a pain level to at least two based on the pain function; and
a pain classification unit for classifying the brainwave data or analysis data thereof to a pain level of the object being estimated based on the pain classifier.

(A16) The apparatus of any one of items A13 to A15, wherein the brainwave data or analysis data thereof comprises an amplitude.

(A17) The apparatus of any one of items A13 to A16, wherein the pain function comprises a linear function or a sigmoid function.

(A17A) The apparatus of any one of items A13 to A17, further comprising one or more features of items A1 to A6, A6A, A7 to A10, A10A, A11, A11A, A12, and A12A.

(A18) A pain estimation method for estimating a magnitude of pain of an object being estimated based on a brainwave of the object being estimated, comprising:
a first measurement step for measuring a brainwave from the object being estimated sequentially inflicted with stimulation of a plurality of magnitudes to obtain brainwave data or analysis data thereof corresponding to stimulation of each magnitude;
an identification step for identifying an upper limit value and a lower limit value of the brainwave data or analysis data thereof of the object being estimated based on the brainwave data or analysis data thereof;

a second measurement step for measuring a brainwave from the object being estimated to obtain object's brainwave data or analysis data thereof; and an estimation step for estimating a value of a magnitude of pain corresponding to the object's brainwave data, based on a relative size of a value of the object's brainwave data or analysis data thereof to the upper limit value and the lower limit value.

(A19) The method of item A18, wherein the brainwave data or analysis data thereof comprises an amplitude.

(A20) The method of item A18 or A19, wherein the estimation step comprises classifying the brainwave data or analysis data thereof to a pain level of the object being estimated based on a predetermined pain classifier, wherein the pain classifier is obtained by fitting the brainwave data or analysis data thereof of the object being estimated to a pain function.

(A21) The method of item A20, wherein the pain function comprises a linear function or a sigmoid function.

(A22) The method of item A20 or A21, wherein the pain function comprises a linear function with a linear approximation of a modulation range, or a more comprehensive sigmoid function encompassing the same.

(A22A) The method of any one of items A18 to A22, further comprising one or more features of items A1 to A6, A6A, A7 to A10, A10A, A11, A11A, A12, A12A, A13 to A17, and A17A.

(A23) A program for implementing a pain estimation method for estimating a magnitude of pain of an object being estimated based on a brainwave of the object being estimated on a computer, the method comprising:

a first measurement step for measuring a brainwave from the object being estimated sequentially inflicted with stimulation of a plurality of magnitudes to obtain brainwave data or analysis data thereof corresponding to stimulation of each magnitude;

an identification step for identifying an upper limit value and a lower limit value of the brainwave data or analysis data thereof of the object being estimated based on the brainwave data or analysis data thereof;

a second measurement step for measuring a brainwave from the object being estimated to obtain object's brainwave data or analysis data thereof; and an estimation step for estimating a value of a magnitude of pain corresponding to the object's brainwave data, based on a relative size of a value of the object's brainwave data or analysis data thereof to the upper limit value and the lower limit value.

(A23A) The program of item A23, further comprising one or more features of items A1 to A6, A6A, A7 to A10, A10A, A11, A11A, A12, A12A, A13 to A17, A17A, items A18 to A22, and A22A.

(A24) A storage medium storing a program for implementing a pain estimation method for estimating a magnitude of pain of an object being estimated based on a brainwave of the object being estimated on a computer, the method comprising:

a first measurement step for measuring a brainwave from the object being estimated sequentially inflicted with stimulation of a plurality of magnitudes to obtain brainwave data or analysis data thereof corresponding to stimulation of each magnitude;

an identification step for identifying an upper limit value and a lower limit value of the brainwave data or analysis data thereof of the object being estimated based on the brainwave data or analysis data thereof;

a second measurement step for measuring a brainwave from the object being estimated to obtain object's brainwave data or analysis data thereof; and an estimation step for estimating a value of a magnitude of pain corresponding to the object's brainwave data, based on a relative size of a value of the object's brainwave data or analysis data thereof to the upper limit value and the lower limit value.

(A24A) The storage medium of item A24, further comprising one or more features of items A1 to A6, A6A, A7 to A10, A10A, A11, A11A, A12, A12A, A13 to A17, A17A, items A18 to A22, A22A, A23, and A23A.

(A25) A method of generating a pain classifier for classifying pain of an object being estimated based on a brainwave of the object being estimated, comprising the steps of:

a) stimulating the object being estimated with a plurality of levels of stimulation intensities;

b) obtaining brainwave data or analysis data thereof of the object being estimated corresponding to the stimulation intensities;

c) plotting, and fitting to a pain function, the stimulation intensities or a subjective pain sensation level corresponding to the stimulation intensities and the brainwave data or analysis data thereof to obtain a pain function specific to the object being estimated; and d) identifying a pain classifier for separating a pain level to at least two based on the specific pain function when a regression coefficient for fitting to the specific pain function is equal to or greater than a predetermined value.

(A26) The method of item A25, further comprising the step of calibrating the pain classifier so that classification of the pain level is at a maximum.

(A27) The method of item A25 or A26, wherein the pain classifier is determined based on an infection point of a pain function or a median value, and the method optionally further comprises the step of calibrating the pain classifier so that classification of the pain level is at a maximum.

(A28) The method of any one of items A25 to A27, wherein the classification classifies whether there is pain or no pain based on a subjective view of the object being estimated.

(A29) The method of any one of items A25 to A28, wherein the stimulation intensities comprise at least one intensity that is highly invasive to the object being estimated.

(A30) The method of any one of items A25 to A29, wherein the stimulation intensities do not comprise an intensity that is highly invasive to the object being estimated.

(A31) The method of any one of items A25 to A30, wherein the brainwave data or analysis data thereof comprises at least one selected from the group consisting of amplitude data and a frequency property.

(A32) The method of any one of items A25 to A31, wherein the pain function comprises a linear function or a sigmoid function.

(A33) The method of any one of items A25 to A32, wherein the pain function comprises a linear function with a linear approximation of a modulation range, or a more comprehensive sigmoid function encompassing the same.

(A34) An apparatus for generating a pain classifier for classifying pain of an object being estimated based on a brainwave of the object being estimated, comprising:

A) a stimulation unit for stimulating the object being estimated with a plurality of levels of stimulation intensities;

B) a brainwave data obtaining unit for obtaining brainwave data or analysis data thereof of the object being estimated corresponding to the stimulation intensities; and C) a pain classifier generation unit for plotting, and fitting to a pain function, the stimulation intensities or a subjective pain sensation level corresponding to the stimulation intensities and the brainwave data or analysis data thereof to obtain a pain function specific to the object being estimated, and identifying a pain classifier for separating a pain level to at least two based on the specific pain function.

(A35) The apparatus of item A34, further having one or more features of items A25 to A33.

(A36) A method of classifying pain of an object being estimated based on a brainwave of the object being estimated, comprising the steps of:

a) stimulating the object being estimated with a plurality of levels of stimulation intensities;

b) obtaining brainwave data or analysis data thereof of the object being estimated corresponding to the stimulation intensities;

c) plotting, and fitting to a pain function, the stimulation intensities or a subjective pain sensation level corresponding to the stimulation intensities and the brainwave data or analysis data thereof to obtain a pain function specific to the object being estimated;

d) identifying a pain classifier for separating a pain level to at least two based on the specific pain function when a regression coefficient for fitting to the specific pain function is equal to or greater than a predetermined value;

e) obtaining the brainwave data or analysis data thereof of the object being estimated; and f) classifying the brainwave data or analysis data thereof to a pain level of the object being estimated based on the pain classifier.

(A37) The method of item A36, wherein the classification of the brainwave data or analysis data thereof based on the pain classifier is characterized by using a mean value.

(A38) The method of A37, wherein the mean value is characterized by using a mean value between about 15 seconds to 120 seconds.

(A39) The method of any one of items A36 to A38, wherein the pain function comprises a linear function or a sigmoid function.

(A39A) The method of any one of items A36 to A39, further having one or more features of items A25 to A35.

(A40) An apparatus for classifying pain of an object being estimated based on a brainwave of the object being estimated, comprising:

A) a stimulation unit for stimulating the object being estimated with a plurality of levels of stimulation intensities;

B) a brainwave data obtaining unit for obtaining brainwave data or analysis data thereof of the object being estimated;

C) a pain classifier generation unit for plotting, and fitting to a pain function, the stimulation intensities or a subjective pain sensation level corresponding to the stimulation intensities and the brainwave data or analysis data thereof to obtain a pain function specific to the object being estimated, and identifying a pain classifier for separating a pain level to at least two based on the specific pain function; and D) a pain classification unit for classifying the brainwave data or analysis data thereof to a pain level of the object being estimated based on the pain classifier.

(A41) The apparatus of item A40, further having one or more features of items A25 to A39.

(A42) A method of classifying pain of an object being estimated based on a brainwave of the object being estimated, comprising the steps of:

e) obtaining brainwave data or analysis data thereof of the object being estimated; and f) classifying a pain level of the object being estimated by fitting the brainwave data or analysis data thereof to a predetermined pain classifier;

wherein the pain classifier is obtained by fitting the brainwave data or analysis data thereof of the object being estimated to a pain function.

(A43) A method of item A42, wherein the pain function comprises a linear function or a sigmoid function.

(A43A) The method of item A42 or A43, further having one or more features of items A25 to A39, A39A, and A40 to A41.

(A44) An apparatus for classifying pain of an object being estimated based on a brainwave of the object being estimated, comprising:

X) an amplitude data obtaining unit for obtaining brainwave data or analysis data thereof of the object being estimated; and Y) a pain classification unit for classifying a pain level of the object being estimated by fitting the brainwave data or analysis data thereof to the pain classifier, wherein the pain classifier is obtained by fitting the brainwave data or analysis data thereof of the object being estimated to a pain function.

(A45) The apparatus of item A44, wherein the pain function comprises a linear function or a sigmoid function.

(A45A) The apparatus of item A44 or A45, further having one or more features of items A25 to A39, A39A, A40 to A43, and A43A.

(A46) A program for having a computer perform a method of generating a pain classifier for classifying pain of an object being estimated based on a brainwave of the object being estimated, the method comprising the steps of:

a) stimulating the object being estimated with a plurality of levels of stimulation intensities;

b) obtaining brainwave data or analysis data thereof of the object being estimated corresponding to the stimulation intensities;

c) plotting, and fitting to a pain function, the stimulation intensities or a subjective pain sensation level corresponding to the stimulation intensities and the brainwave data or analysis data thereof to obtain a pain function specific to the object being estimated; and d) identifying a pain classifier for separating a pain level to at least two based on the specific pain function when a regression coefficient for fitting to the specific pain function is equal to or greater than a predetermined value.

(A47) The program of item A46, wherein the pain function comprises a linear function or a sigmoid function.

(A47A) The program of item A46 or A47, further having one or more features of items A25 to A39, A39A, A40 to A43, A43A, A44 to A45, and A45A.

(A48) A storage medium comprising a program for having a computer perform a method of generating a pain classifier for classifying pain of an object being estimated based on a brainwave of the object being estimated, the method comprising the steps of:

a) stimulating the object being estimated with a plurality of levels of stimulation intensities;

b) obtaining brainwave data or analysis data thereof of the object being estimated corresponding to the stimulation intensities;

c) plotting, and fitting to a pain function, the stimulation intensities or a subjective pain sensation level corresponding to the stimulation intensities and the brainwave data or analysis data thereof to obtain a pain function specific to the object being estimated; and d) identifying a pain classifier for separating a pain level to at least two based on the pain function when a regression coefficient for fitting to the specific pain function is equal to or greater than a predetermined value.

(A49) The storage medium of item A48, wherein the pain function comprises a linear function or a sigmoid function.

(A49A) The storage medium of item A48 or A49, further having one or more features of items A25 to A39, A39A, A40 to A43, A43A, A44 to A45, A45A, A46 to A47, and A47A.

(A50) A program for having a computer execute a method of classifying pain of an object being estimated based on a brainwave of the object being estimated, the method comprising the steps of:

a) stimulating the object being estimated with a plurality of levels of stimulation intensities;

b) obtaining brainwave data or analysis data thereof of the object being estimated corresponding to the stimulation intensities;

c) plotting, and fitting to a pain function, the stimulation intensities or a subjective pain sensation level corresponding to the stimulation intensities and the brainwave data or analysis data thereof to obtain a pain function specific to the object being estimated;

d) identifying a pain classifier for separating a pain level to at least two based on the specific pain function when a regression coefficient for fitting to the specific pain function is equal to or greater than a predetermined value;

e) obtaining the brainwave data or analysis data thereof of the object being estimated; and f) classifying the brainwave data or analysis data thereof to a pain level of the object being estimated based on the pain classifier.

(A51) The program of item A50, wherein the pain function comprises a linear function or a sigmoid function.

(A51A) The program of item A50 or A51, further having one or more features of items A25 to A39, A39A, A40 to A43, A43A, A44 to A45, A45A, A46 to A47, A47A, A48 to A49, and A49A.

(A52) A storage medium comprising a program for having a computer execute a method of classifying pain of an object being estimated based on a brainwave of the object being estimated, the method comprising the steps of:

a) stimulating the object being estimated with a plurality of levels of stimulation intensities;

b) obtaining brainwave data or analysis data thereof of the object being estimated corresponding to the stimulation intensities;

c) plotting, and fitting to a pain function, the stimulation intensities or a subjective pain sensation level corresponding to the stimulation intensities and the brainwave data or analysis data thereof to obtain a pain function specific to the object being estimated;

d) identifying a pain classifier for separating a pain level to at least two based on the specific pain function when a regression coefficient for fitting to the specific pain function is equal to or greater than a predetermined value;

e) obtaining the brainwave data or analysis data thereof of the object being estimated; and f) classifying the brainwave data or analysis data thereof to a pain level of the object being estimated based on the pain classifier.

(A53) The storage medium of item A52, wherein the pain function comprises a linear function or a sigmoid function.

(A53A) The storage medium of item A52 or A53, further having one or more features of items A25 to A39, A39A, A40 to A43, A43A, A44 to A45, A45A, A46 to A47, A47A, A48 to A49, A49A, A50 to A51, and A51A.

(A54) A program for having a computer execute a method of classifying pain of an object being estimated based on a brainwave of the object being estimated, the method comprising the steps of:

e) obtaining brainwave data or analysis data thereof of the object being estimated; and f) classifying a pain level of the object being estimated by fitting the brainwave data or analysis data thereof to a predetermined pain classifier;

wherein the pain classifier is obtained by fitting the brainwave data or analysis data thereof of the object being estimated to a pain function.

(A55) The program of item A54, wherein the pain function comprises a linear function or a sigmoid function.

(A55A) The program of item A54 or A55, further having one or more features of items A25 to A39, A39A, A40 to A43, A43A, A44 to A45, A45A, A46 to A47, A47A, A48 to A49, A49A, A50 to A51, A51A, A52 to A53, and A53A.

(A56) A storage medium comprising a program for having a computer execute a method of classifying pain of an object being estimated based on a brainwave of the object being estimated, the method comprising the steps of:

e) obtaining brainwave data or analysis data thereof of the object being estimated; and f) classifying a pain level of the object being estimated by fitting the brainwave data or analysis data thereof to a predetermined pain classifier;

wherein the pain classifier is obtained by fitting the brainwave data or analysis data thereof of the object being estimated to a pain function.

(A57) The storage medium of item A56, wherein the pain function comprises a linear function or a sigmoid function.

(A57A) The storage medium of item A56 or A57, further having one or more features of items A25 to A39, A39A, A40 to A43, A43A, A44 to A45, A45A, A46 to A47, A47A, A48 to A49, A49A, A50 to A51, A51A, A52 to A53, A53A, A54 to A55, and A55A.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description as needed.

The present invention also provides the following.

(B1) A pain estimation apparatus for estimating a magnitude of pain of an object being estimated based on a brainwave of the object being estimated, comprising:

a measurement unit for measuring a brainwave a plurality of times from the object being estimated to obtain a plurality of brainwave data; and an estimation unit for estimating a relative magnitude of pain upon the measurement of a brainwave a plurality of times from an amplitude of the plurality of brainwave data, based on a linearity in a relationship between the amplitude of a brainwave and pain.

(B2) The pain estimation apparatus of item B1,
wherein the plurality of brainwave data comprise first brainwave data and second brainwave data,
wherein the estimation unit
(i) estimates that first pain corresponding to the first brainwave data is greater than second pain corresponding to the second brainwave data if an amplitude of the first brainwave data is greater than an amplitude of the second brainwave data, and
(ii) estimates that the first pain is less than the second pain if the amplitude of the first brainwave data is less than the amplitude of the second brainwave data.

(B3) The pain estimation apparatus of item B2,
wherein the plurality of brainwave data further comprise third brainwave data and fourth brainwave data,
wherein the estimation unit further estimates a relative amount of change between a first change from the first pain to the second pain and a second change from third pain corresponding to the third brainwave data to fourth pain corresponding to the fourth brainwave data, based on a first value of difference between an amplitude value of the first brainwave data and an amplitude value of the second brainwave data and a second value of difference between an amplitude value of the third brainwave data and an amplitude value of the fourth brainwave data.

(B4) A pain estimation method for estimating a magnitude of pain of an object being estimated based on a brainwave of the object being estimated, comprising:
a measurement step for measuring a brainwave a plurality of times from the object being estimated to obtain a plurality of brainwave data; and
an estimation step for estimating a relative magnitude of pain upon the measurement of a brainwave a plurality of times from an amplitude of the plurality of brainwave data based on a linearity in a relationship between the amplitude of brainwave and pain.

(B5) A pain estimation apparatus for estimating a magnitude of pain of an object being estimated based on a brainwave of the object being estimated, comprising:
a measurement unit for measuring a brainwave from an object being estimated sequentially inflicted with stimulation of a plurality of magnitudes to obtain brainwave data corresponding to stimulation of each magnitude; and
an identification unit for identifying an upper limit value and a lower limit value of a brainwave amplitude of the object being estimated based on the brainwave data;
wherein the measurement unit further measures a brainwave from the object being estimated to obtain object's brainwave data, and
wherein the pain estimation apparatus further comprises an estimation unit for estimating a value of a magnitude of pain corresponding to the object's brainwave data based on a relative size of an amplitude value of the object's brainwave data with respect to the upper limit value and the lower limit value.

(B6) The pain estimation apparatus of item B5, wherein the estimation unit estimates a ratio of a value of difference between the amplitude value of the object's brainwave data and the lower limit value to a value of difference between the upper limit value and the lower limit value as a value of the magnitude of pain.

(B7) A pain estimation method for estimating a magnitude of pain of an object being estimated based on a brainwave of the object being estimated, comprising:
a first measurement step for measuring a brainwave from the object being estimated sequentially inflicted with stimulation of a plurality of magnitudes to obtain brainwave data corresponding to stimulation of each magnitude;
an identification step for identifying an upper limit value and a lower limit value of a brainwave amplitude of the object being estimated based on the brainwave data;
a second measurement step for measuring a brainwave from the object being estimated to obtain object's brainwave data; and
an estimation step for estimating a value of magnitude of pain corresponding to the object's brainwave data, based on a relative size of an amplitude value of the object's brainwave data to the upper limit value and the lower limit value.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description as needed.

The present invention further provides the following.

(C1) A method of generating a pain classifier for classifying pain of an object being estimated based on a brainwave of the object being estimated, comprising the steps of:
a) stimulating the object being estimated with a plurality of levels of stimulation intensities;
b) obtaining brainwave data or analysis data thereof of the object being estimated corresponding to the stimulation intensities;
c) plotting, and fitting to a sigmoid function pattern, the stimulation intensities or a subjective pain sensation level corresponding to the stimulation intensities and the brainwave data or analysis data thereof to obtain a sigmoid curve specific to the object being estimated; and
d) identifying a pain classifier for separating a pain level to at least two based on the sigmoid curve when a regression coefficient for fitting to the sigmoid function pattern is equal to or greater than a predetermined value.

(C2) The method of item C1, further comprising the step of calibrating the pain classifier so that classification of the pain level is at a maximum.

(C3) The method of item C1 or C2, wherein the pain classifier is determined based on an infection point of the sigmoid curve, and the method optionally further comprises the step of calibrating the pain classifier so that classification of the pain level is at a maximum.

(C4) The method of any one of items C1 to C3, wherein the classification classifies whether there is pain or no pain based on a subjective view of the object being estimated.

(C5) The method of any one of items C1 to C4, wherein the stimulation intensities comprise at least one intensity that is highly invasive to the object being estimated.

(C6) The method of any one of items C1 to C5, wherein the stimulation intensities do not comprise an intensity that is highly invasive to the object being estimated.

(C7) The method of any one of items C1 to C6, wherein the brainwave data or analysis data thereof comprises at least one selected from the group consisting of amplitude data and a frequency property.

(C8) An apparatus for generating a pain classifier for classifying pain of an object being estimated based on a brainwave of the object being estimated, comprising:
A) a stimulation unit for stimulating the object being estimated with a plurality of levels of stimulation intensities;
B) a brainwave data obtaining unit for obtaining brainwave data or analysis data thereof of the object being estimated corresponding to the stimulation intensities; and C) a pain classifier generation unit for plotting, and fitting to a sigmoid function pattern, the stimulation intensities or a subjective pain sensation level corresponding to the stimulation intensities and the brainwave data or analysis data thereof to obtain a sigmoid curve specific to the object being estimated, and identifying a pain classifier for separating a pain level to at least two based on the sigmoid curve.

(C9) The apparatus of item C8, further having one or more features of items C2 to C7.

(C10) A method of classifying pain of an object being estimated based on a brainwave of the object being estimated, comprising the steps of:
a) stimulating the object being estimated with a plurality of levels of stimulation intensities;
b) obtaining brainwave data or analysis data thereof of the object being estimated corresponding to the stimulation intensities;
c) plotting, and fitting to a sigmoid function pattern, the stimulation intensities or a subjective pain sensation level corresponding to the stimulation intensities and the brainwave data or analysis data thereof to obtain a sigmoid curve specific to the object being estimated;
d) identifying a pain classifier for separating a pain level to at least two based on the sigmoid curve when a regression coefficient for fitting to the sigmoid function pattern is equal to or greater than a predetermined value;
e) obtaining the brainwave data or analysis data thereof of the object being estimated; and
f) classifying the brainwave data or analysis data thereof to a pain level of the object being estimated based on the pain classifier.

(C11) The method of item C10, wherein the fitting of the brainwave data or analysis data thereof to the pain classifier is characterized by using a mean value.

(C12) The method of C10, wherein the mean value is characterized by using a mean value between about 15 seconds to 120 seconds.

(C13) An apparatus for classifying pain of an object being estimated based on a brainwave of the object being estimated, comprising:
A) a stimulation unit for stimulating the object being estimated with a plurality of levels of stimulation intensities;
B) a brainwave data obtaining unit for obtaining brainwave data or analysis data thereof of the object being estimated (wherein brainwave data corresponding to the stimulation intensities and actual brainwave amplitude data or analysis data thereof can be obtained);
C) a pain classifier generation unit for plotting, and fitting to a sigmoid function pattern, the stimulation intensities or a subjective pain sensation level corresponding to the stimulation intensities and the brainwave data or analysis data thereof to obtain a sigmoid curve specific to the object being estimated, and identifying a pain classifier for separating a pain level to at least two based on the sigmoid curve; and
D) a pain classification unit for classifying the brainwave data or analysis data thereof to a pain level of the object being estimated based on the pain classifier.

(C14) The apparatus of item C13, further having one or more features of item C11 and C12.

(C14A) The apparatus of any one of items C11 to C14, further having one or more features of item C2 to C7.

(C15) A method of classifying pain of an object being estimated based on a brainwave of the object being estimated, comprising the steps of:
e) obtaining brainwave data or analysis data thereof of the object being estimated; and
f) classifying the brainwave data or analysis data thereof to a pain level of the object being estimated based on a predetermined pain classifier;
wherein the pain classifier is obtained by fitting the brainwave data or analysis data thereof of the object being estimated to a sigmoid curve.

(C15A) The method of item C15, further having one or more features of items C2 to C7 and C11 to C12.

(C16) An apparatus for classifying pain of an object being estimated based on a brainwave of the object being estimated, comprising:
X) an amplitude data obtaining unit for obtaining brainwave data or analysis data thereof of the object being estimated; and
Y) a pain classification unit for classifying the brainwave data or analysis data thereof to a pain level of the object being estimated based on the pain classifier, wherein the pain classifier is obtained by fitting the brainwave data or analysis data thereof of the object being estimated to a sigmoid curve.

(C16A) The apparatus of item C16, further having one or more features of items C2 to C7 and C11 to C12.

(C17) A program for having a computer perform a method of generating a pain classifier for classifying pain of an object being estimated based on a brainwave of the object being estimated, the method comprising the steps of:
a) stimulating the object being estimated with a plurality of levels of stimulation intensities;
b) obtaining brainwave data or analysis data thereof of the object being estimated corresponding to the stimulation intensities;
c) plotting, and fitting to a sigmoid function pattern, the stimulation intensities or a subjective pain sensation level corresponding to the stimulation intensities and the brainwave data or analysis data thereof to obtain a sigmoid curve specific to the object being estimated; and
d) identifying a pain classifier for separating a pain level to at least two based on the sigmoid curve when a regression coefficient for fitting to the specific pain function is equal to or greater than a predetermined value.

(C17A) The program of item C17, further having one or more features of items C2 to C7 and C11 to C12.

(C18) A storage medium comprising a program for having a computer perform a method of generating a pain classifier for classifying pain of an object being estimated based on a brainwave of the object being estimated, the method comprising the steps of:
a) stimulating the object being estimated with a plurality of levels of stimulation intensities;
b) obtaining brainwave data or analysis data thereof of the object being estimated corresponding to the stimulation intensities;
c) plotting, and fitting to a sigmoid function pattern, the stimulation intensities or a subjective pain sensation level corresponding to the stimulation intensities and the brainwave data or analysis data thereof to obtain a sigmoid curve specific to the object being estimated; and
d) identifying a pain classifier for separating a pain level to at least two based on the sigmoid curve when a regression coefficient for fitting to the sigmoid function pattern is equal to or greater than a predetermined value.

(C18A) The storage medium of item C18, further having one or more features of items C2 to C7 and C11 to C12.

(C19) A program for having a computer execute a method of classifying pain of an object being estimated based on a brainwave of the object being estimated, the method comprising the steps of:
a) stimulating the object being estimated with a plurality of levels of stimulation intensities;
b) obtaining brainwave data or analysis data thereof of the object being estimated corresponding to the stimulation intensities;
c) plotting, and fitting to a sigmoid function pattern, the stimulation intensities or a subjective pain sensation level corresponding to the stimulation intensities and the brainwave data or analysis data thereof to obtain a sigmoid curve specific to the object being estimated;
d) identifying a pain classifier for separating a pain level to at least two based on the sigmoid curve when a regression coefficient for fitting to the sigmoid function pattern is equal to or greater than a predetermined value;
e) obtaining the brainwave data or analysis data thereof of the object being estimated; and
f) classifying a pain level of the object being estimated by fitting the brainwave data or analysis data thereof to the pain classifier.
(C19A) The program of item C19, further having one or more features of items C2 to C7 and C11 to C12.
(C20) A storage medium comprising a program for having a computer execute a method of classifying pain of an object being estimated based on a brainwave of the object being estimated, the method comprising the steps of:
a) stimulating the object being estimated with a plurality of levels of stimulation intensities;
b) obtaining brainwave data or analysis data thereof of the object being estimated corresponding to the stimulation intensities;
c) plotting, and fitting to a sigmoid function pattern, the stimulation intensities or a subjective pain sensation level corresponding to the stimulation intensities and the brainwave data or analysis data thereof to obtain a sigmoid curve specific to the object being estimated;
d) identifying a pain classifier for separating a pain level to at least two based on the sigmoid curve when a regression coefficient for fitting to the sigmoid function pattern is equal to or greater than a predetermined value;
e) obtaining the brainwave data or analysis data thereof of the object being estimated; and
f) classifying the brainwave data or analysis data thereof to a pain level of the object being estimated based on the pain classifier.
(C20A) The storage medium of item C20, further having one or more features of items C2 to C7 and C11 to C12.
(C21) A program for having a computer execute a method of classifying pain of an object being estimated based on a brainwave of the object being estimated, the method comprising the steps of:
e) obtaining brainwave data or analysis data thereof of the object being estimated; and
f) classifying the brainwave data or analysis data thereof to a pain level of the object being estimated based on a predetermined pain classifier;
wherein the pain classifier is obtained by fitting the brainwave data or analysis data thereof of the object being estimated to a sigmoid curve.
(C21A) The program of item C21, further having one or more features of items C2 to C7 and C11 to C12.
(C22) A storage medium comprising a program for having a computer execute a method of classifying pain of an object being estimated based on a brainwave of the object being estimated, the method comprising the steps of:
e) obtaining brainwave data or analysis data thereof of the object being estimated; and
f) classifying the brainwave data or analysis data thereof to a pain level of the object being estimated based on a predetermined pain classifier;
wherein the pain classifier is obtained by fitting the brainwave data or analysis data thereof of the object being estimated to a sigmoid curve.
(C22A) The storage medium of item C22, further having one or more features of items C2 to C7 and C11 to C12.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description as needed.

It is also intended that the features of any one or more of A series, B series, and C series can be provided in combination with one another. Additional embodiments and advantages of the present invention are recognized by those skilled in the art by reading and understanding the following detailed description as needed.

In one aspect, the present invention provides a pain estimation method and apparatus. The apparatus is for estimating and classifying a magnitude of pain of an object being estimated based on a brainwave of the object being estimated. The apparatus and method measure a brainwave a plurality of times from the object being estimated to obtain a plurality of brainwave data or analysis data thereof, and fit a relationship between an amplitude of a brainwave or frequency property and pain to a pain function to generate a pain classifier from the amplitude, frequency, or the like of the plurality of brainwave data. Optionally, a pain classifier is calibrated, and then a relative pain level is estimated using the pain classifier.

This configuration can estimate a relative magnitude of pain upon measurement of a brainwave a plurality of times to estimate the pain level from an amplitude or frequency property of the plurality of brainwave data or analysis data thereof, based on a relative relationship between the amplitude of brainwave data and pain. The existence of a certain relative relationship between the amplitude or frequency property of a brainwave and pain is a phenomenon elucidated by the inventor. The present invention can further classify the magnitude and level of pain without using the magnitude of pain declared by the object being estimated by fitting the relative relationship to a pain function, such that pain of the object being estimated can be objectively and accurately classified. Furthermore, the quality of pain can be classified by "unbearable" pain, "bearable" pain, "comfortable pain" and the like, so that the therapeutic effect can be more accurately evaluated.

For example, the plurality of brainwave data or analysis data thereof comprise a sufficient number of brainwave data or analysis data thereof to enable fitting to an exemplified pain function such as a linear function or a sigmoid curve. For such fitting, brainwave data or analysis data thereof for at least three stimulation intensities, preferably brainwave data or analysis data thereof for 4, 5, 6, 7, or more stimulation intensities can be used.

Once such fitting to a pain function is completed in the present invention, a regression coefficient is optionally evaluated to determine whether the fitting is appropriate. Generally, 0.5 or greater, or preferably 0.6 or greater can be used as a threshold value of a regression coefficient. If a suitable regression coefficient is accomplished, the fitting is suitable, so that analysis proceeds to the next analysis. If a regression coefficient is evaluated to be unsuitable, additional brainwave data or analysis data thereof can be obtained for re-fitting to a pain function with the existing data, brainwave data or analysis data thereof is obtained again for re-fitting to a pain function only with the newly obtained data.

Once fitting is completed, a pain classifier is generated based on a pain function. A pain classifier refers to a specific value of brainwave data (e.g., amplitude) or analysis data thereof for classifying pain into at least two classes. For example, a pain classifier can be a value for classification into "weak pain" and "strong pain". It is desirable to be able to clinically classify pain into "unbearable pain requiring therapy" and "bearable pain that does not require therapy". Such a pain classifier can be determined by considering an inflection point or the like.

A pain classifier that is generated can be utilized directly, but the classifier can be optionally calibrated. For example, calibration is materialized, when classified into "weak pain" and "strong pain", by fitting the classifier to actually obtain brainwave data (e.g., amplitude) or analysis data thereof and change the classifier to a value with less deviation (i.e., classification into a different class, including determination as strong pain when it should be weak pain or vice versa) or to a value with the least deviation.

For brainwave data or analysis data thereof, (i) first pain corresponding to first brainwave data (e.g., amplitude) or analysis data thereof can be estimated to be greater than second pain corresponding to second brainwave data (e.g., amplitude) or analysis data thereof if the first brainwave data or analysis data thereof is greater than the second brainwave data or analysis data thereof, which is different from the first brainwave data or analysis data thereof, and (ii) the first pain can be estimated to be less than the second pain if the first brainwave data (e.g., amplitude) or analysis data thereof is less than the second brainwave data or analysis data thereof, in which case the data can be further compared to a pain classifier to classify which level of pain (e.g., strong pain, weak pain, or the like) the first and second pain falls under.

This embodiment can estimate which of the first pain corresponding to the first brainwave data or analysis data thereof (e.g., amplitude) and the second pain corresponding to the second brainwave data or analysis data thereof (e.g., amplitude) is greater by comparing the first brainwave data or analysis data thereof with the second brainwave data or analysis data thereof. For example, the magnitude of pain before, during, and/or after therapy can therefore be compared to evaluate a therapeutic effect by measuring brainwave data or analysis data thereof before and after therapy.

For example, the plurality of brainwave data or analysis data thereof can obtain additional brainwave data or analysis data thereof.

The pain estimation apparatus and method according to another embodiment of the invention is a pain estimation apparatus and method for estimating a magnitude of pain of an object being estimated based on a brainwave of the object being estimated, measuring a brainwave from the object being estimated inflicted with a plurality of magnitudes of stimulation to obtain brainwave data (amplitude, frequency property, or the like) or analysis data thereof corresponding to stimulation of each magnitude (in the apparatus, a measurement unit performs the action of obtaining) and identifying brainwave data (also referred to as a brainwave property; includes amplitude, frequency property and the like) or analysis data thereof corresponding to one or more magnitudes of stimulation based on the brainwave data or analysis data thereof as a pain classifier (in the apparatus, a pain classifier generation unit performs this action). Preferably, the pain estimation apparatus and method further measure a brainwave from the object being estimated, obtain new brainwave data, classify the newly obtained brainwave data or analysis data thereof based on the pain classifier, and classify the magnitude of pain corresponding to the object's brainwave data. Such classification is executed by a pain classification unit in the apparatus.

This configuration can classify a magnitude of pain based on a pain classifier. By utilizing a pain classifier, a magnitude of pain can be classified without using a magnitude of pain declared by an object being estimated, so that pain of the object being estimated can be expressed and classified objectively and accurately. Furthermore, stimulation corresponding to strong pain does not need to be collected, or can be kept to a minimum, from an object being estimated or the like. Thus, a magnitude of pain can be readily estimated without inflicting pain on an object. For example, the magnitude of pain before, during, and/or after therapy can be compared and/or classified to evaluate a therapeutic effect by measuring brainwave data or analysis data thereof before, during, and/or after therapy.

Certain embodiments provide a method and apparatus for generating a pain classifier for classifying pain of an object being estimated based on a brainwave of the object being estimated, where the object being estimated is stimulated at a plurality of levels of stimulation intensities. As the number of stimulation intensity levels (magnitudes), a sufficient number that enables fitting to a pain function is provided. At least two, preferably at least 3, preferably at least 4, preferably at least 5, preferably at least 6 or more levels (magnitudes) of stimulation intensities can be used for fitting to a pain function.

These comprehensive or specific embodiments of the invention can be materialized with a system, method, integrated circuit, computer program, or a storage medium such as a computer readable CD-ROM or any combination of a system, method, integrated circuit, computer program, and storage medium.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description as needed.

Advantageous Effects of Invention

The pain estimation apparatus according to one embodiment of the invention can be objectively and accurately estimate pain of an object being estimated.

The present invention can readily classify pain. A preferred embodiment provides a pain classifier without inflicting strong pain to an object, or by using a minimum number of pain. This can be used to perform various treatments without inflicting strong pain, or with minimum pain, or classify a therapeutic effect.

BRIEF DESCRIPTION OF DRAWINGS

FIG. 10B is a flow chart depicting an example of an estimation process according to embodiment 1.

FIG. 10C is a flow chart depicting another example of a pain estimation process according to embodiment 1.

FIG. 15 shows absolute amplitude data (one subject) of 18 epochs associated with 6 intensity levels immediately before averaging for each level in Example 1.

FIG. 2 shows standardized absolute amplitude averaging three epochs in each intensity level. The horizontal and vertical axes indicate stimulation intensity and standardized amplitude, respectively.

FIG. 3 clearly shows a decreasing sigmoid function between intensity level and amplitude, which supports that lower level 2 and higher level 1 have statistically significantly different amplitudes by a statistical result (t=2.886, p=0.013)

FIG. 18 shows a binary pain classifier for one patient.

FIG. 27 depicts a schematic diagram of a linearly approximated portion of a sigmoid function.

DESCRIPTION OF EMBODIMENTS

Figure 1:
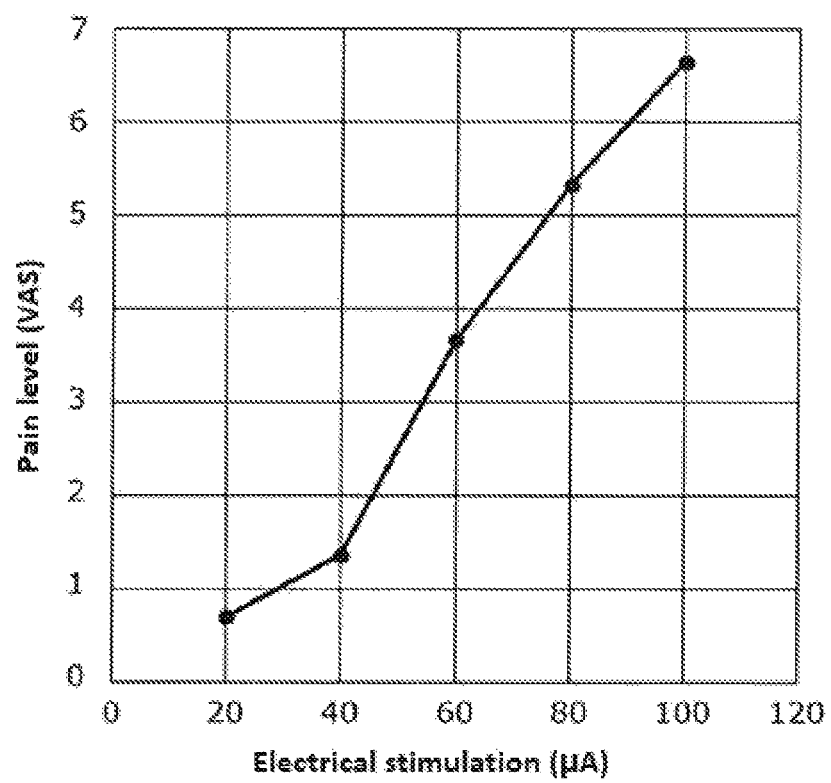
FIG. 1 is a graph showing the relationship between electrical stimulation and pain level (VAS).

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definition

The terms and the general technologies used herein are first explained.

As used herein, "object" is used synonymously with patient and subject and refers to any organism or animal which is subjected to the technology in the disclosure such as pain measurement and brainwave measurement. An object is preferably, but is not limited to, humans. As used herein, an object may be referred to an "object undergoing estimation" when estimating pain, but this has the same meaning as object or the like.

As used herein, "brainwave" has the meaning that is commonly used in the art and refers to a current generated by a difference in potential due to neurological activity of the brain when a pair of electrodes is placed on the scalp. Brainwave encompasses electroencephalogram (EEG), which is obtained from deriving and recording temporal changes in the current. A wave with an amplitude of about 50 µV and a frequency of approximately 10 Hz is considered the primary component at rest. This is referred to an a wave. During neurological activity, a waves are suppressed and a fast wave with a small amplitude of 17 to 30 Hz appears, which is referred to as a β wave. During a period of shallow sleep, α waves gradually decrease and θ waves of 4 to 8 Hz appear. During a deep sleep, δ waves of 1 to 4 Hz appear. These brainwaves can be described by a specific amplitude and frequency power. In the present invention, analysis of amplitudes can be important.

As used herein, "brainwave data" is any data related to brainwaves (also referred to as "amount of brain activity", "brain characteristic amount", or the like), such as amplitude data (EEG amplitude, frequency property, or the like). "Analysis data" from analyzing such brainwave data can be used in the same manner referred to as "brainwave data or analysis data thereof" herein. Examples of analysis data include mean amplitude and peak amplitude of brainwave data (e.g., Fz, Cz, C3, C4), frequency power (e.g., Fz(δ), Fz(Γ), Fz(α), Fz(β), Fz(γ), Cz(δ), Cz(θ), Cz(α), Cz(β), Cz(γ), C3(δ), C3(θ), C3(α), C3(β), C3(γ), C4(δ), C4(θ), C4(α), C4(β), C4(γ)) and the like. Of course, this does not exclude other data commonly used as brainwave data or analysis data thereof.

As used herein, "amplitude data" is one type of "brainwave data" and refers to data for amplitudes of brainwaves. This is also referred to as simply "amplitude" or "EEG amplitude". Since such amplitude data is an indicator of brain activity, such data can also be referred to as "brain activity data", "amount of brain activity", or the like. Amplitude data can be obtained by measuring electrical signals of a brainwave and is indicated by potential (can be indicated by µV or the like). Amplitude data that can be used include, but are not limited to, mean amplitude.

As used herein, "frequency power" expresses frequency components of a waveform as energy and is also referred to as power spectrum. Frequency power can be calculated by extracting and calculating frequency components of a signal embedded in a signal contained in noise in a time region by utilizing fast Fourier transform (FFT) (algorithm for calculating discrete Fourier transform (DFT) on a computer at a high speed). FFT of a signal can, for example, use the function periodogram in MATLAB to normalize the output thereof and calculate the power spectrum density PSD or power spectrum, which is the source of measurement of power. PSD indicates how power of a time signal is distributed with respect to frequencies, and the unit thereof is watt/Hz. Each point of PSD is integrated over the range of frequencies where the points are defined (i.e., over the resolution bandwidth of PSD) to calculate the power spectrum. The unit of a power spectrum is watt. The value of power can be read directly from power spectrum without integration over the range of frequencies. PSD and power spectrum are both real numbers, so that no phase information is included. In this manner, frequency power can be calculated with a standard function in MATLAB.

"Pain" refers to a sensation that is generated as stimulation, generally upon intense injury such as damage/inflammation to a body part. In humans, this includes common sensation as sensation accompanying unpleasant feeling. In addition, cutaneous pain and the like also has an aspect of external receptor, which plays a role in determining the quality such as hardness, sharpness, hotness (thermal pain), coldness (cold pain), or spiciness of an external object in cooperation with other skin sensation or taste. The sensation of pain of humans can occur at almost any part of the body (e.g., pleura, peritoneum, internal organs (visceral pain, excluding the brain), teeth, eyes, ears, and the like) except the skin and mucous membrane, which can all be sensed as a brainwave or a change thereof in the brain. Additionally, internal sensation of pain represented by visceral pain is also encompassed by sensation of pain. The aforementioned sensation of pain is referred to as somatic pain relative to visceral pain. In addition to somatic pain and visceral pain, sensation of pain called "referred pain", which is a phenomenon where pain is perceived at a surface of a site that is different from a site that is actually damaged, is also reported. This can also be classified in the present invention.

For sensation of pain, there are individual differences in sensitivity (pain threshold), as well as qualitative difference due to a difference in the receptor site or how a pain stimulation occurs. Sensation of pain is classified into dull pain, sharp pain, and the like, but sensation of pain of any type can be measured, estimated, and classified in the present disclosure. The disclosure is also compatible with fast sensation of pain (A sensation of pain), slow sensation of pain (B sensation of pain), (fast) topical pain, and (slow) diffuse pain. The present invention is also compatible with abnormality in sensation of pain such as hyperalgesia. Two nerve fibers, i.e., "Aδ fiber" and "C fiber", are known as peripheral nerves that transmit pain. For example, when a hand is hit, the initial pain is transmitted as sharp pain from a clear origin (primary pain: sharp pain) by conduction through the Aδ fiber. Pain is then conducted through the C fiber to feel throbbing pain (secondary pain; dull pain) with an unclear origin. Pain is classified into "acute pain" lasting 4 to 6 weeks or less and "chronic pain" lasting 4 to 6 weeks or more. Pain is an important vital sign along with pulse, body temperature, blood pressure, and breathing, but is difficult to express as objective data. Representative pain scales VAS (Visual Analogue Scale) and faces pain rating scale are subjective evaluation methods that cannot compare pain between patients. Meanwhile, the inventor has focused on brainwaves which are hardly affected by the peripheral circulatory system as an indicator for objectively evaluating pain, arriving at the conclusion that any type of pain can be determined and classified by observing the change in amplitude/latency to pain stimulation and fitting this to a sigmoid curve, which is one of the pain functions. While instantaneous stimulation and sustained stimulation can both be detected, one of the advantages is that sustained stimulation is remarkably detected in particular.

One of the important points of the present invention is in the ability to determine whether pain is pain "requiring therapy", rather than the intensity in itself. Therefore, it is important that "pain" can be clearly categorized based on the concept of "therapy". For example, this leads to "qualitative" classification of pain such as "pleasant/unpleasant" or "unbearable". For example, the position of a "pain classifier", infection point, width of a classifier, and the relationship thereof can be defined. In addition to a case of n=2, cases where n=3 or greater can also be envisioned. When n is 3 or greater, pain can be separated into "not painful", "comfortable pain", and "painful". For example, pain can be determined as "unbearable, need therapy", "moderate", "painful, but not bothersome". The determination using a sigmoid function of the invention can identify "unbearable" and "painful but bearable, no need for therapy".

As used herein, "subjective pain sensation level" refers to the level of sensation of pain of the object, and can be expressed by conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like.

As used herein, "pain classifier" refers to a value or range of brainwave data (e.g., amplitude) or analysis data thereof identified for classifying the type of pain. In this disclosure, a unit, apparatus, or instrument for generating a "pain classifier" (and thus predicting pain) can also be referred to as a "pain classification instrument", "pain prediction instrument", or the like. In this disclosure, a pain classifier can be determined by, for example, but not limited to, utilizing an inflection point or the like based on a specific pain function (e.g., also referred to as a linear function or sigmoid curve specific to an object being estimated) obtained by stimulating the object being estimated and plotting, and applying and fitting into a pain function, stimulation intensity or a subjective pain sensation level corresponding thereto from data such as amplitude data of brainwaves obtained therefrom. A pain classifier, once generated, can be improved by calibration. A pain classifier can be denoted as pain classifier, pain predictor, or the like, which are synonymous. It is possible to determine whether it is "change within the strong level of pain" or "qualitative change indicating low level of pain, which is a deviation from the strong level of pain" by using a "pain classifier". If there is a reaction with a deviation beyond a change within the strong level of pain, this can be determined from a change within the strong level of pain using the pain classifier of the invention. If there is a change within the strong level of pain, a change that is not an error can be identified, and anything beyond this can be processed as a deviating reaction.

As used herein, "pain function" is the relationship between pain level and stimulation level expressed in a mathematical function of a dependent variable (variable Y) and an independent variable (variable X), where the function expresses the relationship based on the "broadly defined" linearity between brainwave or analysis data thereof (including, for example, amplitude) and pain elucidated by the inventor as a function. In view of this relationship, (i) first pain corresponding to first brainwave data or analysis data thereof (including, for example, amplitude) can be estimated to be greater than second pain corresponding to second brainwave data or analysis data thereof (including, for example, amplitude) if the first brainwave data is greater than the second brainwave data, and (ii) the first pain can be estimated to be less than the second pain if the first brainwave data or analysis data thereof (including, for example, amplitude) is less than the second brainwave data or analysis data thereof (including, for example, amplitude). Any function that can express this is understood to be within the scope of the pain function. Examples of such a pain function include linear functions and sigmoid functions. More specific examples include linear functions with linear approximation of the modulation range and more comprehensive sigmoid functions encompassing the same. Linearity can also be, in addition to amplitude, any brainwave characteristic amount such as frequency or wavelet processing value. The present invention has discovered that linearity in the modulation range can be found in not only brainwave characteristic amounts, but also in subjective evaluation.

As used herein, "stimulation" includes any stimulation that can cause sensation of pain. Examples thereof include electrical stimulation, cold stimulation, thermal stimulation, physical stimulation, chemical stimulation, and the like. In the present invention, stimulation used for generating a pain classifier can be any stimulation, but temperature stimulation (cold stimulation or thermal stimulation) or electrical stimulation is generally used. 3 or more stimulation levels are generally used, preferably 4 or more, more preferably 5 or more, and still more preferably 6 or more, or more types of stimulation can be used. For temperature, for example when low temperature stimulation is used, temperature can be reduced to an appropriate sensation in the range of, for example, −15° C. to 10° C. When 6 points are obtained, the temperature can be reduced by 5° C. to generate stimulation of 6 temperature levels. Evaluation of stimulation can be matched with subjective pain sensation levels using, for example, conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like. Examples of values that can be employed as stimulation intensity include nociceptive threshold (threshold for generating neurological impulses to nociceptive fiber), pain detection threshold (intensity of nociceptive stimulation that can be sensed as pain by humans), pain tolerance threshold (strongest stimulation intensity among experimentally tolerable nociceptive stimulation by humans), and the like.

As used herein, "sigmoid function" or "sigmoid curve" refers to a real function exhibiting a sigmoidal shape. In the present invention, normalized subjective pain intensity and normalized EEG amplitude can be used to generate a sigmoid curve, which has been actually demonstrated.

A sigmoid function is generally represented by $\sigma_a(x)=1/(1+e^{-ax})=(\tanh(ax+2)+1)/2$. A decreasing sigmoid function can be expressed by subtraction from 1 or a reference value. A monotonically increasing continuous function of $(-\infty, \infty) \to (0, 1)$ has one inflection point. This function has an asymptote at $y=0$ and $y=1$. In such a case, the inflection point is $(0, \frac{1}{2})$. For setting an asymptote, the function may not have an asymptote at 0 or 1 depending on the measured (and optionally normalized) amplitude data (EEG amplitude), but the maximum value and minimum value can be used as an asymptote in such a case.

As used herein, "fitting" to a linear function, sigmoid function, or the like refers to a technique of fitting measured values or a curve obtained therefrom to approximate a pain function (e.g., linear function or nonlinear function), which can be performed based on any approach. For example, a known sigmoid function can be used. Examples of such fitting include least square fitting, nonlinear regression fitting (MATLAB nlinfit function or the like), and the like. After fitting, a regression coefficient can be calculated for the approximated sigmoid curve to determine whether the sigmoid curve can be used or preferable in the present invention. For a regression coefficient, a regression model is effective. The adjusted coefficient of determination ($R^2$) is desirable with a numerical value closer to "1" such as 0.5 or greater, 0.6 or greater, 0.7 or greater, 0.8 or greater, 0.85 or greater, 0.9 or greater, or the like. A higher numerical value has higher confidence. The precision of fitting can be investigated by using a specific threshold value to categorize and compare an estimated value and an actual measurement value (this is referred to as precision of determination in the analysis of the invention).

As used herein, "calibration", for a pain classifier, refers to any step for correcting the pain classifier or a corrected value thereof generated by fitting to a pain function more in line with the classification of the object of measurement. Examples of such calibration include an approach to increase/decrease the value so that the classification of a pain level is at a maximum and the like. Other examples include, but are not limited to, approaches such as a method of applying a specific reference stimulation at a specific time interval and weighting using a coefficient or the like from the change in the amount of brain activity to correct the determination of a change in pain within an individual.

As used herein, "classification" of pain can be made from various viewpoints. Representative examples include classification to whether it is "painful" or "not painful" for the object being estimated, and additionally include, but are not limited to, classification of feeling pain, but with quantitative distinction between strong pain and weak pain, as well as qualitative distinction ("bearable" pain and "unbearable" pain).

Preferred Embodiments

The preferred embodiments of the present invention are explained hereinafter. It is understood that the embodiments provided hereinafter are provided to better facilitate the understanding of the present invention, so that the scope of the invention should not be limited by the following descriptions. Thus, it is apparent that those skilled in the art can refer to the descriptions herein to make appropriate modifications within the scope of the invention. It is also understood that the following embodiments of the invention can be used individually or as a combination.

Each of the embodiments explained below describes a comprehensive or specific example. The numerical values, shapes, materials, and constituent elements, arrangement positions and connection forms of the constituent elements, steps, orders of steps, and the like in the following embodiments are one example, which is not intended to limit the Claims. Further, the constituent elements in the following embodiments that are not recited in the independent claims indicating the most superordinate concept are explained as an optional constituent element.

Linearity

The inventor has found that the technology in Patent Literature 1 described in the section of "Technical Field" results in the following problem.

Patent Literature 1 classifies a set of reference data indicating brainwave activity of a plurality of individuals into reference data of several pain states and compares the characteristics extracted from each classified reference data with characteristics extracted from brainwave data to estimate pain from the brainwave data. In this regard, the pain states used in classifying reference data are based on pain declared by subjects. Therefore, it is difficult to suitable classify reference data unless the declared pain is accurate.

Pain is often declared by subjects according to Visual Analog Scale (VAS). VAS is a method for a subject to declare a pain level by indicating which position, on a 10 cm straight line representing pain levels, from 0 to 100 the current pain level is. However, in VAS, declared pain levels are dependent on the past experience to pain of a subject, such that it is difficult to objectively evaluate pain.

Therefore, it is difficult to objectively and accurately estimate pain of a subject with the technology of Cited Reference 1, which estimates pain of a subject using reference data classified with a pain level declared by the subject.

In this regard, the inventor has elucidated the relationship between pain and brainwave by evaluating a plurality of types of pain by a plurality of methods. The relationship between pain and brainwaves elucidated by the inventor is explained with reference to the drawings.

First, the relationship between pain from electrical stimulation and brainwaves is explained. Data provided below indicates data of a representative subject among a plurality of subjects.

Figure 2:
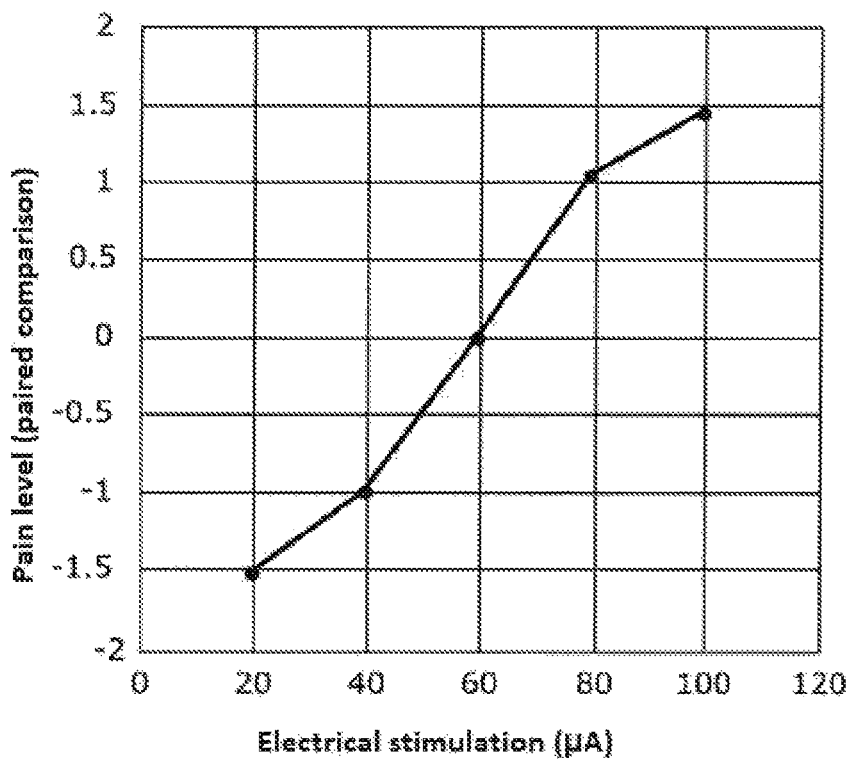
FIG. 2 is a graph showing the relationship between electrical stimulation and pain level (paired comparison).
Figure 3:
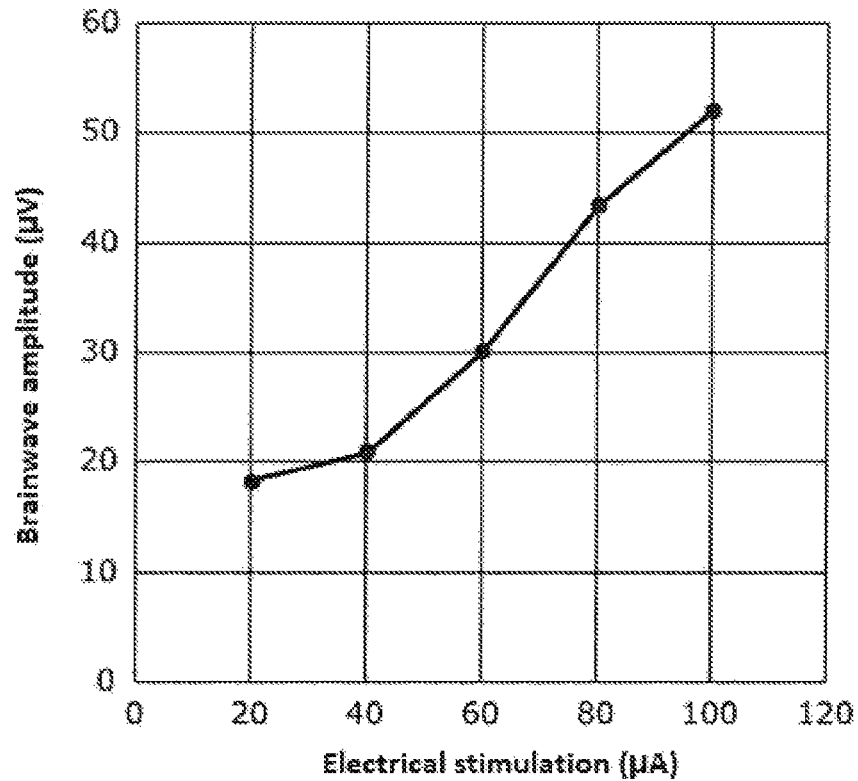
FIG. 3 is a graph showing the relationship between electrical stimulation and brainwave amplitude.
Figure 4:
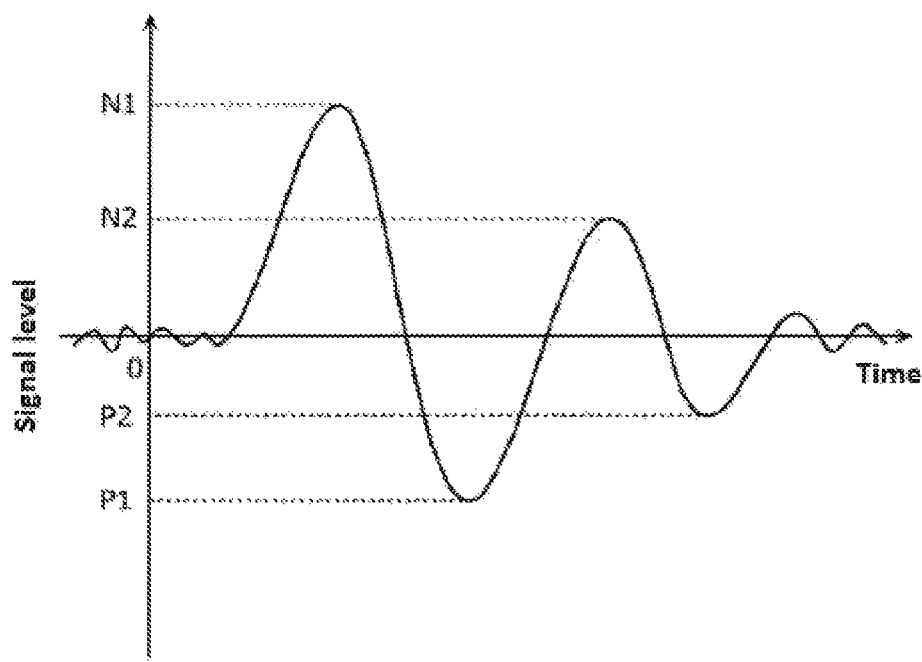
FIG. 4 is a graph showing an example of a brainwave waveform.

FIG. 1 is a graph showing the relationship between electrical stimulation and pain level (VAS). FIG. 2 is a graph showing the relationship between electrical stimulation and pain level (paired comparison). FIG. 3 is a graph showing the relationship between electrical stimulation and brainwave amplitude. FIG. 4 is a graph showing an example of a brainwave waveform.

The horizontal axes of FIGS. 1, 2, and 3 indicate a current value of electrical stimulation. The vertical axis in FIG. 1 indicates the pain level declared by a subject according to VAS. The vertical axis in FIG. 2 indicates the pain level declared by a subject according to paired comparison. The vertical axis in FIG. 3 indicates an amplitude value of a brainwave. In FIG. 4, the horizontal axis indicates time, and the vertical axis indicates a signal level.

Paired comparison is a method for a subject to declare which electrical stimulation is how much more painful for each of the plurality of sets of electrical stimulation, with electrical stimulation of two magnitudes as a set, by a numerical value. In such a case, a pain level is declared by comparing a pair of pain, so that the effect of past experiment of the subject on pain levels can be alleviated.

As shown in FIGS. 1 and 2, the relationship between a current value of electrical stimulation (i.e., intensity of stimulation) and pain level exhibits strong linearity in the intermediate region of electrical stimulation intensities in either the method by VAS or paired comparison. The linearity in the intermediate region can be included in a part of a more comprehensive sigmoid (S-shaped) curve, and the shape thereof (e.g., upper limit value, lower limit value, and the like) varies by subjects.

As shown in FIG. 3, the relationship between a current value of electrical stimulation and amplitude value of a brainwave also exhibits strong linearity in the intermediate region of electrical stimulation intensities. In this regard, a value of difference between the maximum peak value and the minimum peak value (i.e., peak-to-peak value) is used as the amplitude value of a brainwave. For example in FIG. 4, the maximum value of difference (N1–P1) among the three values of difference (N1–P1, N2–P2, and N1–P2) is used as an amplitude value.

In this manner, both the relationship between the intensity of electrical stimulation and pain level and the relationship between the intensity of electrical stimulation and amplitude value of a brainwave have linearity in the intermediate region. In other words, the pain level and amplitude of a brainwave both have an upper limit and lower limit to electrical stimulation and exhibit a similar change to the intensity of electrical stimulation. When the relationship between the amplitude value of a brainwave and pain level was analyzed in this regard, the relationship between the amplitude value of a brainwave and pain level was represented as in FIGS. 5 and 6.

Figure 5:
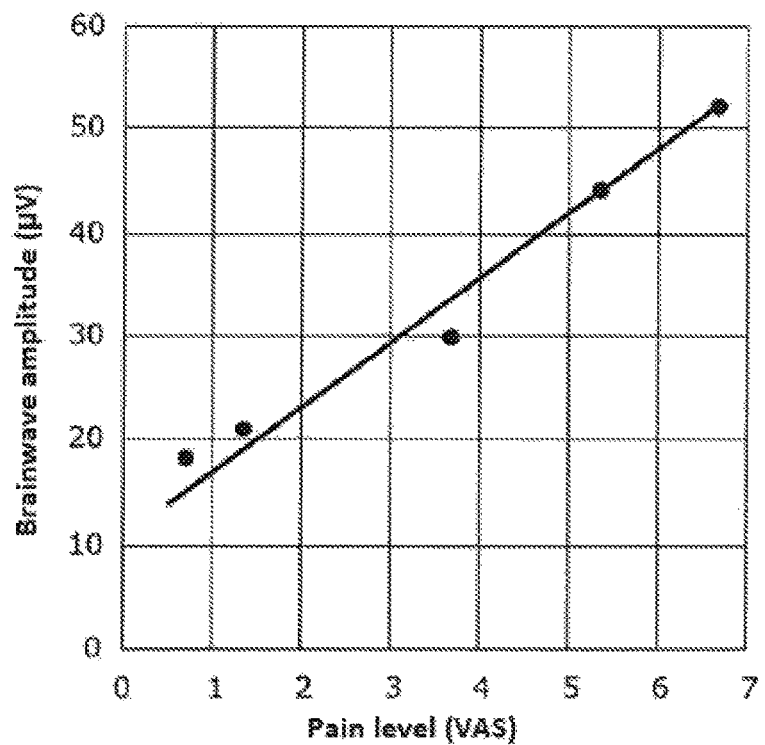
FIG. 5 is a graph showing a linear relationship between the pain level (VAS) from electrical stimulation and brainwave amplitude.
Figure 6:
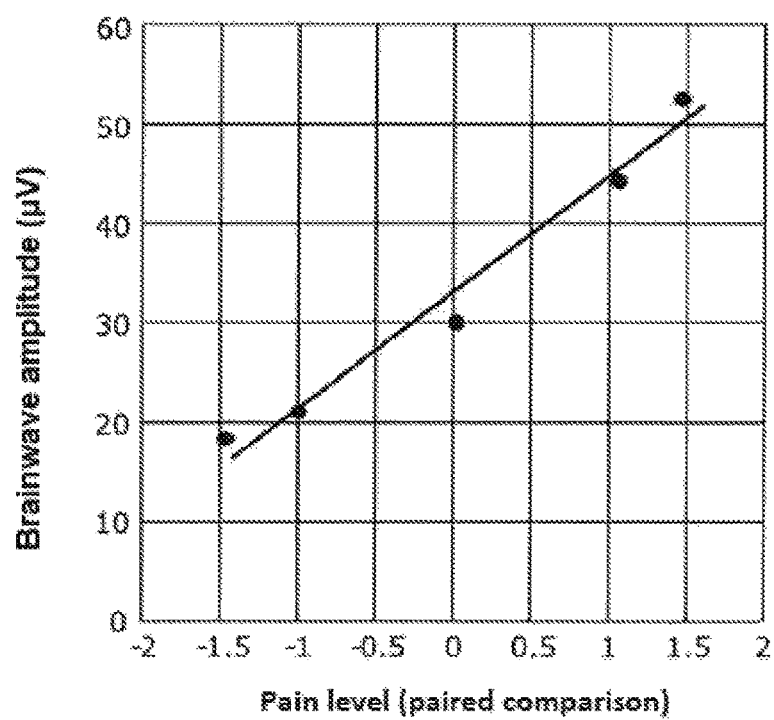
FIG. 6 is a graph showing the linear relationship between pain level (paired comparison) from electrical stimulation and brainwave amplitude.

FIG. 5 is a graph showing the relationship between pain level (VAS) from electrical stimulation and brainwave amplitude. FIG. 6 is a graph showing the relationship between pain level (paired comparison) from electrical stimulation and brainwave amplitude. In FIGS. 5 and 6, the vertical axis indicates the amplitude of a brainwave, and the horizontal axis indicates the pain level.

As shown in FIGS. 5 and 6, the pain level from electrical stimulation and amplitude value of a brainwave have linearity in either VAS or paired comparison. In other words, amplitude values of brainwaves are proportional to pain levels.

In this disclosure, linearity includes focused linearity that is partially included in a more comprehensive nonlinear function in addition to strict linearity. In other words, linearity includes relationships that can be approximated to a linear function within a range of a given tolerance for the entire data or within a given range. The range of a given tolerance is defined, for example, by a coefficient of determinant $R^2$ in regression analysis. The coefficient of determinant $R^2$ is a value obtained by subtracting a result of dividing residual sum of squares with total sum of squares from 1. The range of a given tolerance is for example a range where $R^2$ is 0.5 or greater.

The relationship between pain from thermal stimulation and brainwave also has linearity between the pain level and brainwave amplitude as in the case of electrical stimulation.

Figure 7:
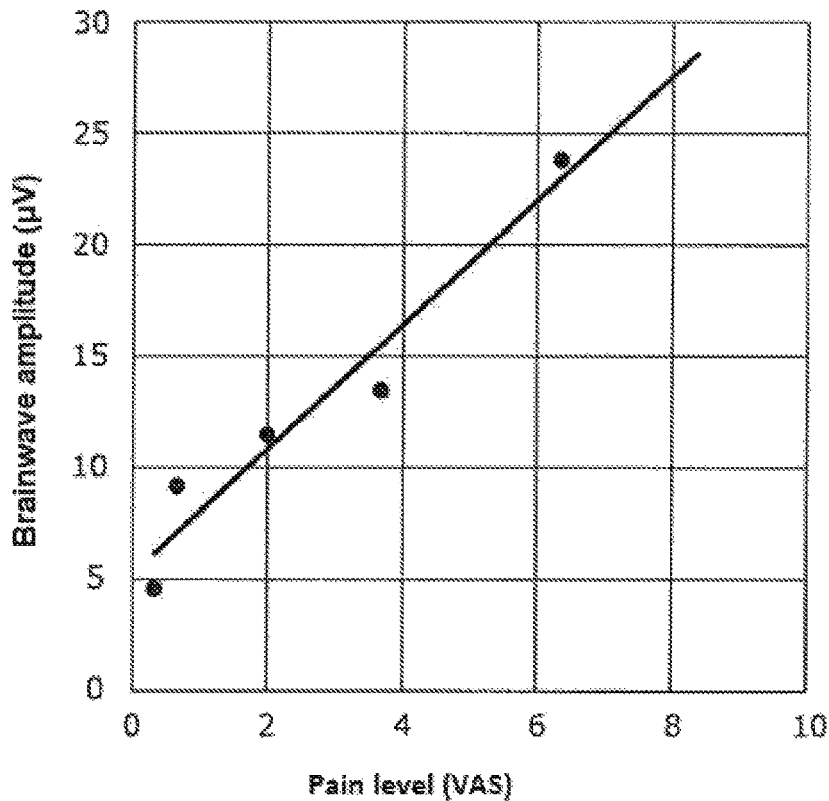
FIG. 7 is a graph showing the linear relationship between pain level (VAS) from thermal stimulation and brainwave amplitude.
Figure 8:
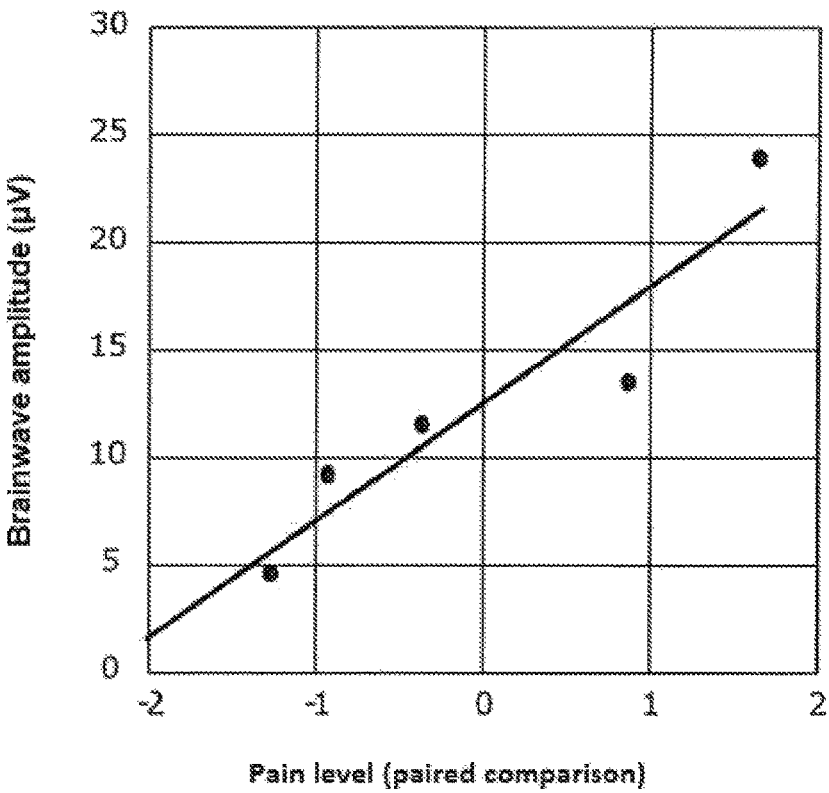
FIG. 8 is a graph showing the linear relationship between pain level (paired comparison) from thermal stimulation and brainwave amplitude.

FIG. 7 is a graph showing the relationship between pain level (VAS) from thermal stimulation and brainwave amplitude. FIG. 8 is a graph showing the relationship between pain level (paired comparison) from thermal stimulation and brainwave amplitude. In FIGS. 7 and 8, the vertical axis indicates the amplitude of a brainwave, and the horizontal axis indicates pain levels.

As shown in FIGS. 7 and 8, the pain level from thermal stimulation and amplitude value of a brainwave have linearity in both VAS and paired comparison. While the upper limit value and the lower limit value of an amplitude value of a brainwave varies by subjects, it was found from the experiment of the inventor that the upper limit value of an amplitude value does not exceed about 60 µV.

In this manner, the inventor has elucidated that the amplitude of a brainwave and pain have linearity as a result of analyzing the relationship between an amplitude value of a brainwave and pain level from evaluating a plurality of types of pain by a plurality of methods.

Estimation of Pain by Linearity

In this regard, the present invention estimates the magnitude of pain based on linearity in the relationship between an amplitude of a brainwave and pain. The present invention is specifically explained below with reference to the drawings based on the embodiments.

Each of the embodiments explained below describes a comprehensive or specific example. The numerical values, shapes, materials, constituent elements, arrangement positions and connection forms of the constituent elements, steps, orders of steps, and the like in the following embodiments are one example, which is not intended to limit the Claims. Further, the constituent elements in the following embodiments that are not recited in the independent claims indicating the most superordinate concept are explained as an optional constituent element.

Embodiment 1 of Estimation by Linearity

Embodiment 1 estimates the relative magnitude of pain upon measurement of brainwaves a plurality of times by utilizing the characteristic of amplitude of a brainwave and pain having linearity. Embodiment 1 is explained below with reference to FIGS. 9 to 10C.

[Configuration of Pain Estimation System]

Figure 9:
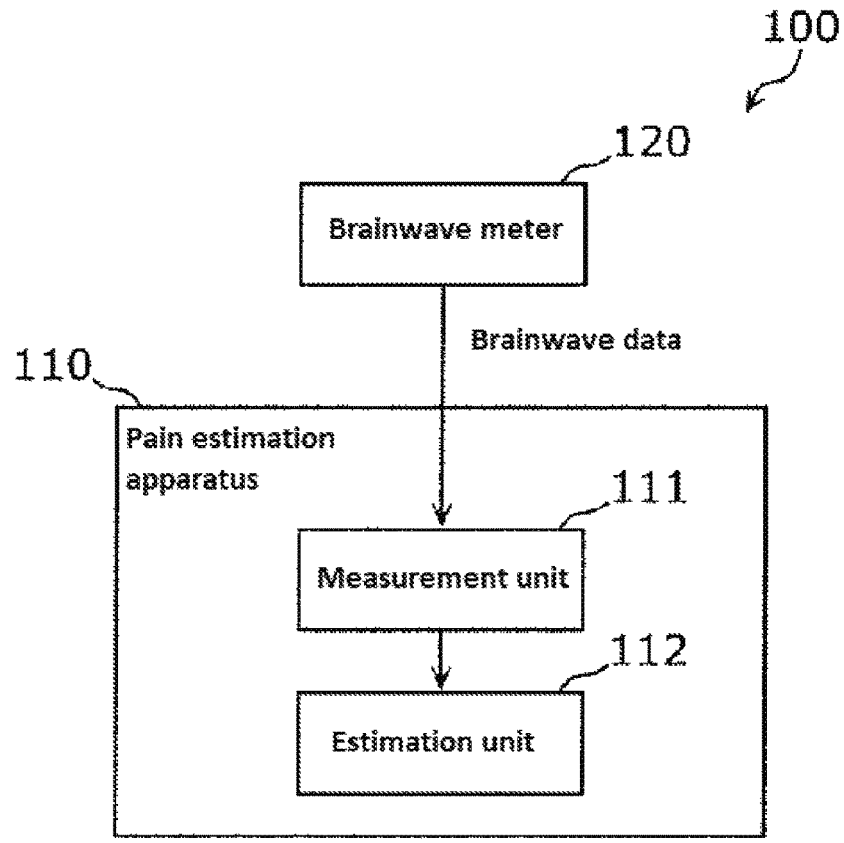
FIG. 9 is a block diagram depicting a function configuration of the pain estimation system according to embodiment 1.

FIG. 9 is a block diagram depicting a functional configuration of the pain estimation system 100 according to embodiment 1. The pain estimation system 100 comprises a pain estimation apparatus 110 and a brainwave meter 120.

The pain estimation apparatus 110 comprises a measurement unit 111 and an estimation unit 112. The pain estimation apparatus 110 is materialized by, for example, a computer comprising a processor and a memory. In such a case, the pain estimation apparatus 110 makes the processor function as the measurement unit 111 and the estimation unit 112 when a program stored in the memory is executed by the processor. The pain estimation apparatus 110 can also be materialized by, for example, a dedicated electrical circuit. A dedicated electrical circuit can be a single integrated circuit or a plurality of electrical circuits.

The measurement unit 111 obtains a plurality of brainwave data by measuring a brainwave a plurality of times from an object being estimated via the brainwave meter 120. An object being estimated is an organism generating a change in brainwave by pain and is not limited to humans.

The estimation unit 112 estimates a relative magnitude of pain upon measurement of a brainwave a plurality of times from an amplitude of a plurality of brainwave data based on linearity in the relationship between the amplitude of a brainwave and pain. In other words, the estimation unit 112 estimates the relative magnitude of pain corresponding to a plurality of brainwave data based on a property of greater pain for greater amplitude of a brainwave.

For example, when a brainwave is measured twice by the measurement unit 111, the estimation unit 112 can estimate the relative magnitude of first pain corresponding to first brainwave data and second pain corresponding to second brainwave data. First, the estimation unit 112 estimates that the first pain is greater than the second pain if an amplitude of the first brainwave data is greater than an amplitude of the second brainwave data. On the other hand, the estimation unit 112 estimates that the first pain is less than the second pain if the amplitude of the first brainwave data is less than the amplitude of the second brainwave data. The estimation unit 112 estimates that the first pain is the same as the second pain if the amplitude of the first brainwave data is the same as the amplitude of the second brainwave data.

For example, when a brainwave is measured four or more times by the measurement unit 111, the estimation unit 112 can further estimate the relative amount of change in pain in the following manner. First, the estimation unit 112 calculates a first value of difference between an amplitude value of the first brainwave data and an amplitude value of the second brainwave data. The estimation unit 112 further calculates a second value of difference between an amplitude value of third brainwave data and an amplitude value of fourth brainwave data. The estimation unit 112 then estimates a relative amount of change between a first change from the first pain corresponding to the first brainwave data to the second pain corresponding to the second brainwave data and a second change from third pain corresponding to the third brainwave data to fourth pain corresponding to the fourth brainwave data, based on the first value of difference and the second value of difference.

Specifically, the estimation unit 112 estimates that the amount of the first change is greater than the amount of the second change if the first value of difference is greater than the second value of difference. On the other hand, the estimation unit 112 estimates that the amount of the first change is less than the amount of the second change if the first value of difference is less than the second value of difference. The estimation unit 112 estimates that the first amount of change is the same as the second amount of change if the first value of difference is the same as the second value of difference.

The brainwave meter 120 measures electrical activity generated within the brain of the object being estimated with an electrode on the scalp. The brainwave meter 120 then outputs brainwave data that is the result of measurement.

[Processing of Pain Estimation System]

Figure 10A:
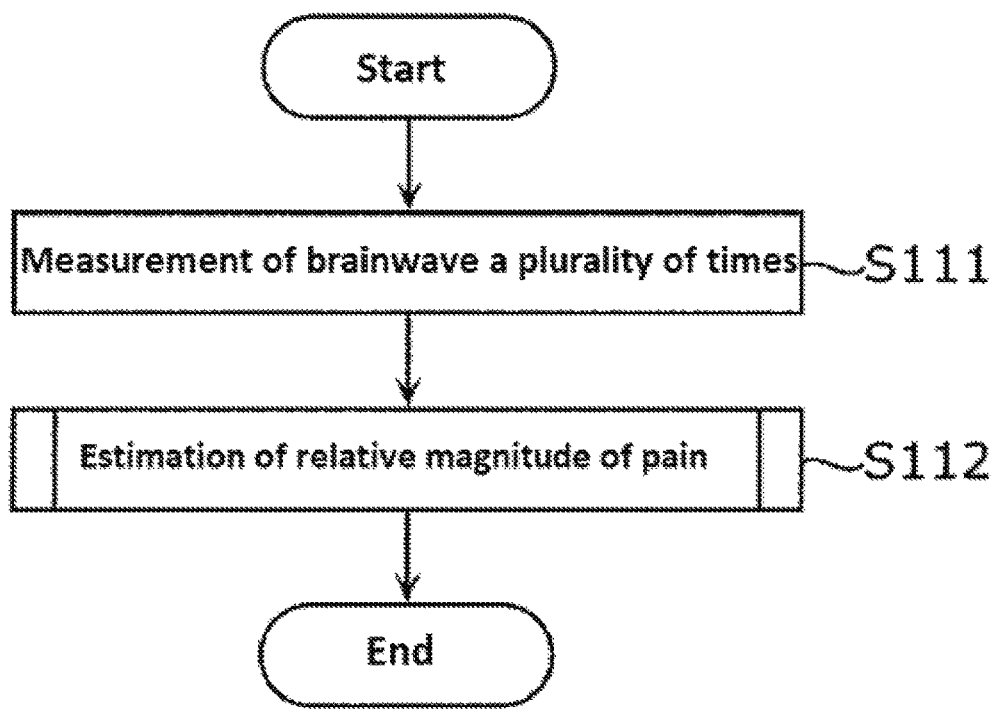
FIG. 10A is a flow chart depicting processing of the pain estimation apparatus according to embodiment 1.

Next, the processing of the pain estimation system 100 configured in the above manner is explained. FIG. 10A is a flow chart depicting the processing of the pain estimation system 100 according to embodiment 1. FIG. 10B is a flow chart depicting an example of the pain estimation process according to embodiment 1. FIG. 10C is a flow chart depicting another example of the pain estimation process according to embodiment 1. Specifically, FIGS. 10B and 10C depict the detailed process of step S112 in FIG. 10A.

First, the measurement unit 111 obtains a plurality of brainwave data by measuring a brainwave a plurality of times from an object being estimated via the brainwave meter 120 (S111). In other words, the measurement unit 111 measures a brainwave at a plurality of times.

Next, the estimation unit 112 estimates a relative magnitude of pain upon measurement of a brainwave a plurality of times from an amplitude of a plurality of brainwave data based on linearity in the relationship between the amplitude of a brainwave and pain (S112). In other words, the estimation unit 112 estimates a relative magnitude of pain at a plurality of times.

For example, the estimation unit 112 can estimate the relative magnitude between first pain at first measurement of brainwave and second pain at the second measurement of brainwave by using the first brainwave data obtained by the first measurement of brainwave and the second brainwave data obtained by the second measurement of brainwave. Specifically, as depicted in FIG. 10B, the estimation unit 112 compares a first amplitude of the first brainwave data and a second amplitude of the second brainwave data (S121). In this regard, the estimation unit 112 estimates that the first pain is greater than the second pain if the first amplitude is greater than the second amplitude (S122). The estimation unit 112 estimates that the first pain is the same as the second pain if the first amplitude is the same as the second amplitude (S123). The estimation unit 112 estimates that the first pain is less than the second pain if the amplitude of the first brainwave data is less than the amplitude of the second brainwave data (S124).

For example, the estimate unit 112 can also estimate a relative amount of change between a first change from the first pain at the first measurement of brainwave to the second pain at the second measurement of brainwave and a second change from third pain at the third measurement of brainwave to fourth pain at the fourth measurement of brainwave. Specifically, as depicted in FIG. 10C, the estimation unit 112 first calculates a first value of difference between an amplitude value of first brainwave data and an amplitude value of second brainwave data (S131). The estimation unit 112 further calculates a second value of difference between an amplitude value of third brainwave data and an amplitude value of fourth brainwave data (S132). The estimation unit 112 then compares the first value of difference with the second value of difference (S133). In this regard, the estimation unit 112 estimates that the first amount of change is greater than the second amount of change if the first value of difference is greater than the second value of difference (S134). The estimation unit 112 estimates that the first amount of change is the same as the second amount of change if the first value of difference is the same as the second value of difference (S135). The estimation unit 112 estimates that the first amount of change is less than the second amount of change if the first value of difference of the brainwave data is less than the second value of difference of the brainwave data (S136).

[Effect]

In view of the above, the pain estimation apparatus 110 according to this embodiment can estimate the relative magnitude of pain upon measurement of a brainwave a plurality of times from amplitudes of a plurality of brainwave data based on linearity in the relationship between the amplitude of a brainwave and pain. Existence of linearity between the amplitude of a brainwave and pain is a phenomenon elucidated by the inventor. The magnitude of pain can be estimated without using the magnitude of pain declared by the object being estimated by utilizing the linearity in the relationship between the amplitude of a brainwave and pain, so that pain of the object being estimated can be objectively and accurately estimated. Furthermore, brainwave data does not need to be collected in advance from the object being estimated or the like, such that the magnitude of pain can be more readily estimated.

The pain estimation apparatus 110 according to this embodiment can also estimate which of first pain corresponding to first brainwave data and second pain corresponding to second brainwave data is greater by comparing the amplitude of the first brainwave data with the amplitude of the second brainwave data. For example, the magnitude of pain before and after therapy can therefore be compared to evaluate a therapeutic effect by measuring brainwave data before and after therapy.

The pain estimation apparatus 110 according to this embodiment can also estimate the relative amount of change in pain by comparing a pair of values of difference in amplitudes of two sets of brainwave data. For example, a change in pain from first therapy can therefore be compared with a change in pain from second therapy, to relatively evaluate therapeutic effects of the first and second therapy.

Embodiment 2 of Estimation by Linearity

Embodiment 2 is now explained. This embodiment uses the upper limit value and lower limit value of an amplitude of a brainwave of an object being estimated when inflicted with stimulation to estimate a magnitude of pain corresponding to object's brainwave data. Embodiment 2 is explained hereinafter with reference to FIGS. 11 to 14 primarily with respect to the differences from Embodiment 1.

[Configuration of Pain Estimation System]

Figure 11:
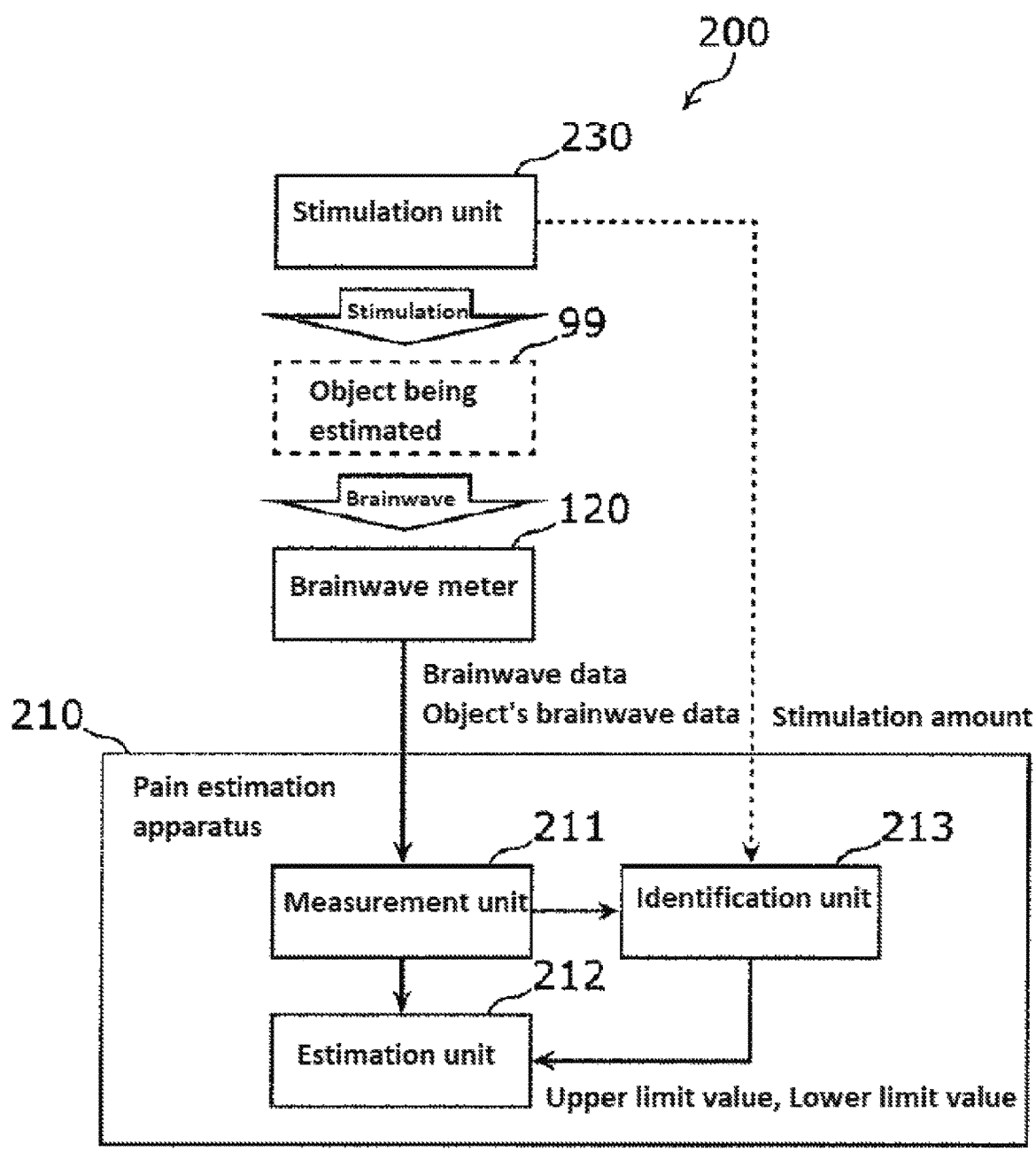
FIG. 11 is a block diagram depicting a functional configuration of the pain estimation system according to embodiment 2.

FIG. 11 is a block diagram depicting a functional configuration of the pain estimation system 200 according to embodiment 2. In FIG. 11, a function block that is similar in FIG. 9 is assigned the same symbol and explanation is appropriately omitted.

The pain estimation system 200 according to this embodiment comprises a pain estimation apparatus 210, a brainwave meter 120, and a stimulation apparatus 230.

The pain estimation apparatus 210 comprises a measurement unit 211, an estimation unit 212, and an identification unit 213. The pain estimation apparatus 210 is materialized, for example, with a computer comprising a processor and a memory. In such a case, the pain estimation apparatus 210 makes the processor function as the measurement unit 211, the estimation unit 212, and the identification unit 213 when a program stored in the memory is executed by the processor. The pain estimation apparatus 210 can also be materialized by, for example, a dedicated electrical circuit. A dedicated electrical circuit can be a single integrated circuit or a plurality of electrical circuits.

The measurement unit 211 obtains brainwave data corresponding to stimulation of each magnitude by measuring a brainwave from an object being estimated 99 sequentially inflicted with stimulation of a plurality of magnitudes via the brainwave meter 120. The brainwave data is used for the process of identifying the upper limit value and the lower limit value of brainwave amplitudes discussed below.

The measurement unit 211 further obtains object's brainwave data by measuring a brainwave from the object being estimated 99. The object's brainwave data is used for the process of estimating pain. In other words, the pain estimation apparatus 210 estimates a value of the magnitude of pain of the object being estimated 99 when measuring a brainwave of the object's brainwave data.

The estimation unit 212 estimates a value of the magnitude of pain corresponding to the object's brainwave data based on a relative magnitude of an amplitude value of the object's brainwave data to the upper limit value and the lower limit value of the brainwave amplitude of the object being estimated 99 identified by the identification unit 213. Specifically, the estimation unit 212 estimates the value of the magnitude of pain corresponding to the object's brainwave data using a ratio of a value of difference between an amplitude value of the object's brainwave data and the lower limit value of the brainwave amplitude to a value of difference between the upper limit value and the lower limit value of the brainwave amplitude.

The identification unit 213 identifies the upper limit value and the lower limit value of the brainwave amplitude of the object being estimated 99 based on the brainwave data obtained by the measurement unit 211. For example, the identification unit 213 identifies the maximum value and the minimum value of amplitudes of a plurality of brainwave data corresponding to stimulation of a plurality of magnitudes as the upper limit value and the lower limit value. For example, the identification unit 213 can also identify the upper limit value and the lower limit value of the brainwave amplitude by analyzing a plurality of brainwave data. Specifically, the identification unit 213 can fit the amplitudes of a plurality of brainwave data for a plurality of magnitudes of stimulation to a sigmoid curve to identify the upper limit value and the lower limit value of the brainwave amplitudes.

The stimulation apparatus 230 inflicts stimulation of a plurality of magnitudes to the object being estimated 99. Specifically, the stimulation apparatus 230 sequentially inflicts a plurality of stimulations to the object being estimated 99 while changing the amount of stimulation. Stimulation is, for example, electrical stimulation, thermal stimulation, or the like.

[Processing of Pain Estimation System]

The processing of the pain estimation system 200 configured in the above manner is now explained. The processing of the pain estimation system 200 includes an identification process for identifying the upper limit value and the lower limit value of a brainwave amplitude and an estimation process for estimating the magnitude of pain corresponding to the object's brainwave data using the identified upper limit value and the lower limit value.

Figure 12:
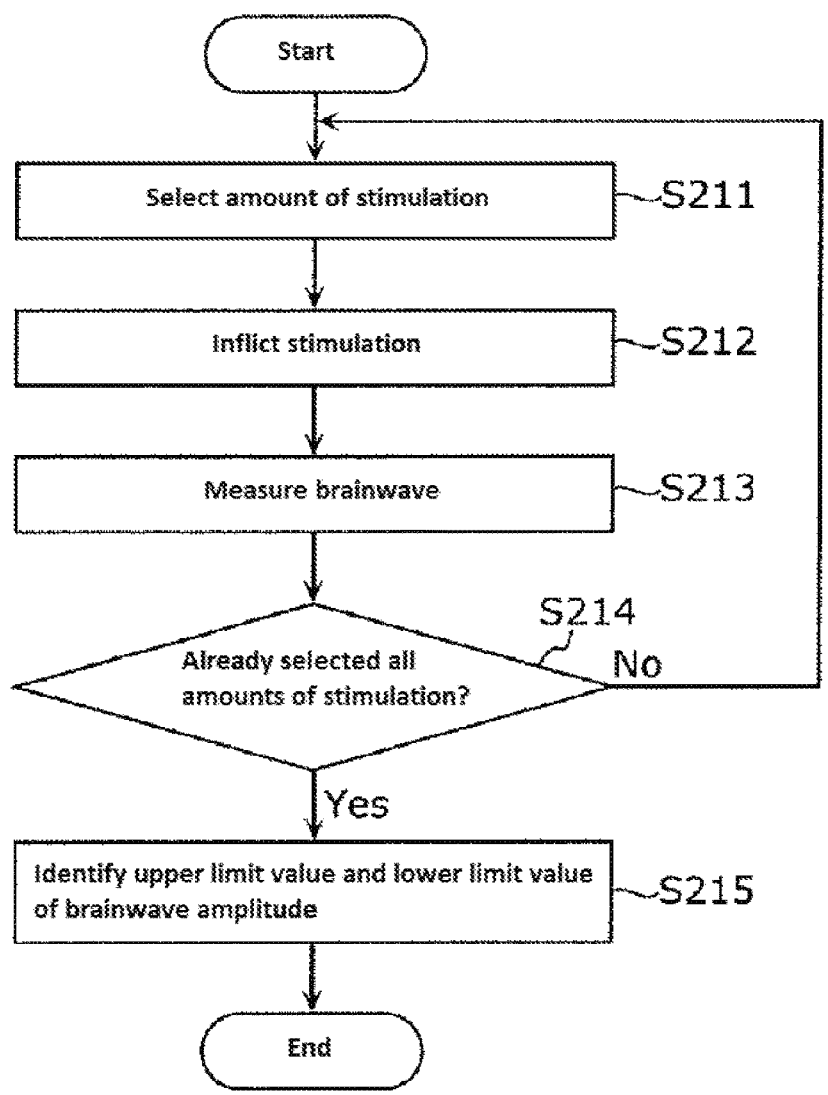
FIG. 12 is a flow chart depicting an identification process in the pain estimation system according to embodiment 2.

FIG. 12 is a flow chart depicting an identification process in the pain estimation system 200 according to embodiment 2.

First, one amount of stimulation that has not been selected is selected from a plurality of amounts of stimulation in the stimulation apparatus 230 (S211). For example, one amount of stimulation that has not been selected is selected from electrical stimulation amounts of 20 µA, 40 µA, 60 µA, 80 µA, and 100 µA.

Next, the stimulation apparatus 230 inflicts the object being estimated 99 with stimulation in the selected amount (S212). When stimulation is inflicted in step S212, the brainwave meter 120 measures a brainwave from the object being estimated 99, and the measurement unit 211 obtains the brainwave data (S213).

If all of the plurality of amounts of stimulation have been selected (Yes in S214), the identification unit 213 identifies the upper limit value and the lower limit value of brainwave amplitudes of the object being estimated 99 based on brainwave data corresponding to each amount of stimulation (S215). If, on the other hand, one of the plurality of amounts of stimulation has not been selected (No in S214), the procedure returns to S211.

In the above manner, a brainwave from the object being estimated 99 sequentially inflicted with stimulation of a plurality of amounts is measured to identify the upper limit value and the lower limit value of a brainwave amplitude in the object being estimated 99 based on the brainwave data corresponding to the plurality of amounts of stimulation.

Figure 13:
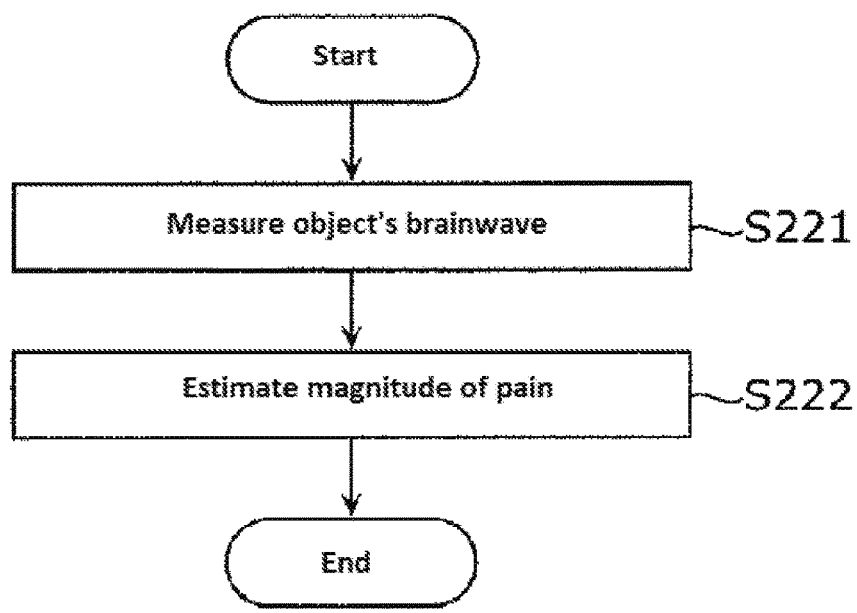
FIG. 13 is a flow chart depicting an estimation process in the pain estimation system according to embodiment 2.
Figure 14:
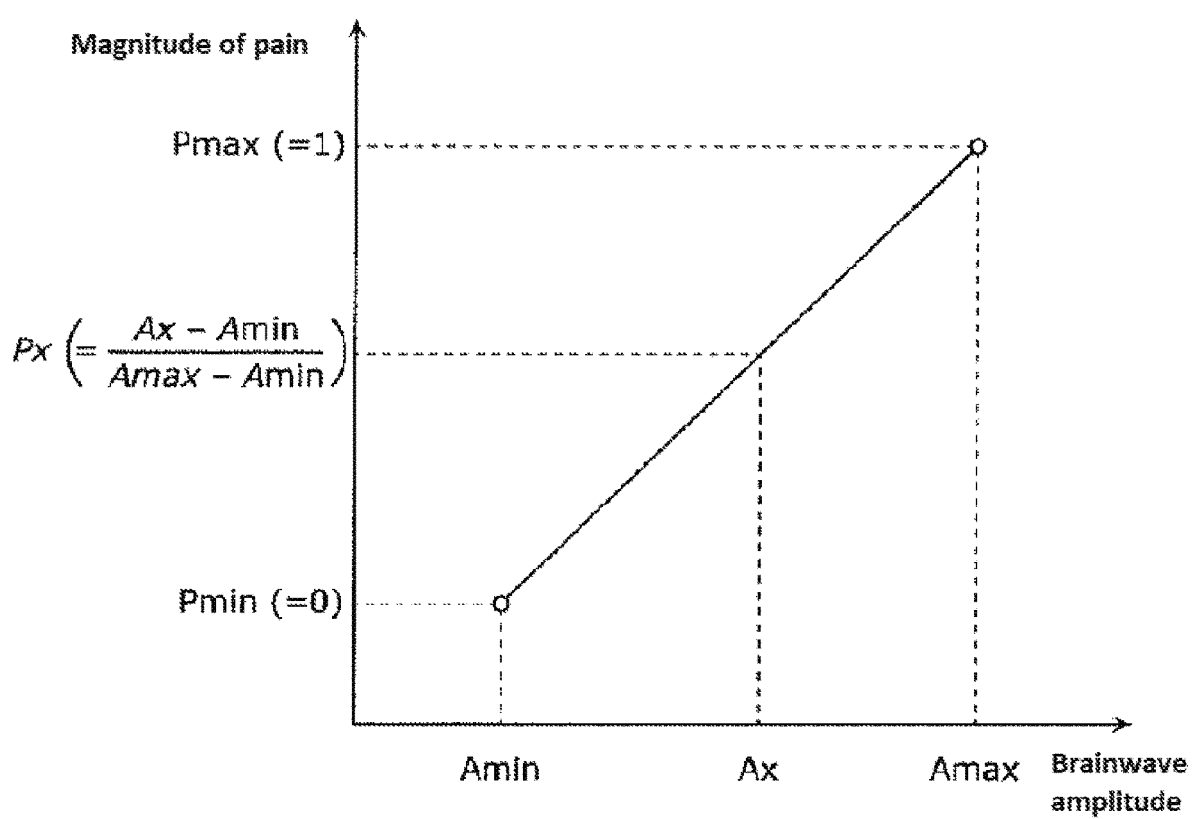
FIG. 14 is a graph for explaining the estimation process in embodiment 2.

Next, the estimation process is explained. FIG. 13 is a flow chart depicting an estimation process in the pain estimation system 200 according to embodiment 2. FIG. 14 is a graph for explaining the estimation process in embodiment 2. In FIG. 14, the vertical axis indicates the magnitude of pain and the horizontal axis indicates the magnitude of a brainwave amplitude.

As depicted in FIG. 13, the brainwave meter 120 first measures a brainwave from the object being estimated 99, and the measurement unit 211 obtains object's brainwave data (S221). In other words, a brainwave is measured when it is desirable to estimate pain of the object being estimated 99.

Next, the estimation unit 212 estimates the magnitude of pain in the object being estimated 99 based on the object's brainwave data (S222). Specifically, the estimation unit 212 estimates the magnitude of pain corresponding to the object's brainwave data based on the relative magnitude of an amplitude value of the object's brainwave data to the upper limit value and the lower limit value of the brainwave amplitude of the object being estimated 99 identified in step S215 of FIG. 12.

For example, as depicted in FIG. 14, the estimation unit 212 estimates the value of the magnitude of pain Px when the amplitude value of object's brainwave data is Ax and the upper limit value and the lower limit value of the brainwave amplitude is Amax and Amin by the following equation.

$$Px = (Ax - A\text{min})/(A\text{max} - A\text{min})$$

In other words, the estimation unit 212 estimates the magnitude of pain corresponding to the object's brainwave data using a ratio of a value of difference between the amplitude value of the object's brainwave data and the lower limit value of the brainwave amplitude to the value of difference between the upper limit value and the lower limit value of the brainwave amplitude in the object being estimated 99.

[Effect]

In the above manner, the pain estimation apparatus 210 according to this embodiment can estimate the value of magnitude of pain corresponding to object's brainwave data based on the relative magnitude of an amplitude value of the object's brainwave data to the upper limit value and the lower limit value of the brainwave amplitude of the object being estimated to quantify the magnitude of pain. Further, neither identification of the upper limit value and the lower limit value nor estimation of a value of the magnitude of pain needs to use the magnitude of pain declared by an object being estimated, so that pain of the object being estimated can be objectively estimated.

Further, the pain estimation apparatus 210 according to this embodiment can estimate a value of the magnitude of pain using a ratio of a value of difference between the amplitude value of object's brainwave data and the lower limit value to the value of difference between the upper limit value and the lower limit value. Therefore, a value of the magnitude of pain can be more readily estimated.

Other Embodiments

The pain estimation apparatuses according to one or more embodiments of the invention have been explained based on the embodiments above, but the present invention is not limited to such embodiments. Various modifications applied to the present embodiments and embodiments constructed by combining constituent elements in different embodiments conceivable to those skilled in the art without departing from the intent of the inventions are also encompassed within the scope of the one or more embodiments of the invention. Linearity can be a value other than amplitude such as a frequency or wavelet processing value, as long as the value is a characteristic amount of brainwaves. Linearity of a modulation range is found not only in the characteristic amount of brainwaves, but also in subjective evaluation. Therefore, it is understood that the portion of the present specification explained with amplitudes as an example is similarly applicable for other characteristic amounts of brainwaves (e.g., frequencies which are characteristic amount of brainwaves, wavelet processing value which is an analysis value thereof, and the like).

For example, each of the above embodiments used a peak-to-peak value as the amplitude value of brainwave data, but amplitude values are not limited thereto. For example, a simple peak value can be used as the amplitude value.

Embodiment 2 has set the range of values of magnitude of pain so that the value Pmax of the magnitude of pain corresponding to the upper limit value Amax of a brainwave amplitude is 1, and the value Pmin of the magnitude of pain corresponding to the lower limit value Amin of the brainwave amplitude is 0, but this is not a limiting example. For example, the magnitude of pain can be represented by 0 to 100. In such a case, the estimation unit 212 can estimate the value Px of magnitude of pain by the following equation.

$$Px = Pmax \times (Ax - Amin)/(Amax - Amin)$$

Embodiment 2 explains curve fitting as an example of identifying the upper limit value and the lower limit value of a brainwave amplitude by analyzing a plurality of brainwave data, but this is not a limiting example. For example, the upper limit value of a brainwave amplitude can be identified using a learning model for estimating a brainwave amplitude for large stimulation from a brainwave amplitude corresponding to small stimulation. In such a case, large stimulation does not need to be inflicted upon an object being estimated, so that physical burden on the object being estimated can be alleviated. Further, a predetermined value can be used as the upper limit value of a brainwave amplitude. The predetermined value is for example 50 μV, which can be experimentally or empirically determined.

Stimulation inflicted upon the object being estimated 99 by the stimulation apparatus 230 is not limited to electrical stimulation and thermal stimulation. Any type of stimulation can be inflicted as long as the magnitude of pain sensed by the object being estimated 99 changes in accordance with the magnitude of stimulation.

Some or all of the constituent elements of the pain estimation apparatus in each of the above embodiments can be comprised of a single system LSI (Large Scale Integration). For example, the pain estimation apparatus 110 can be comprised of system LSI having the measurement unit 111 and the estimation unit 112.

System LSI is ultra-multifunctional LSI manufactured by integrating a plurality of constituents on a single chip, or specifically a computer system comprised of a microprocessor, ROM (Read Only Memory), RAM (Random Access Memory), and the like. A computer program is stored in a ROM. The system LSI accomplishes its function by the microprocessor operating in accordance with the computer program.

The term system LSI was used herein, but the term IC, LSI, super LSI, and ultra LSI can also be used depending on the difference in the degree of integration. The approach for forming an integrated circuit is not limited to LSI, but can be materialized with a dedicated circuit or universal processor. After the manufacture of LSI, a programmable FPGA (Field Programmable Gate Array) or reconfigurable process which allows reconfiguration of the connection or setting of circuit cells inside the LSI can be utilized.

If a technology of integrated circuits that replace LSI by advances in semiconductor technologies or other derivative technologies becomes available, functional blocks can obviously be integrated using such technologies. Application of biotechnology or the like is also a possibility.

One embodiment of the invention can be not only such a pain estimation apparatus, but a pain estimation method using characteristic constituent units contained in the pain estimation apparatus as steps. Further, one embodiment of the invention can be a computer program for having a computer execute each characteristic step in the pain estimation method. Further, one embodiment of the invention can be a computer readable non-transient storage medium on which such a computer program is recorded.

In each of the above embodiments, each constituent element can be materialized by being set up with a dedicated hardware or by executing software program suited to each constituent element. Each constituent element can be materialized by a program execution unit such as a CPU or a processor reading out and executing a software program recorded on a storage medium such as a hard disk or semiconductor memory. In this regard, software materialized with the pain estimation apparatus of each of the above embodiments is a program such as those described below.

In other words, this program makes a computer execute a pain estimation method for estimating a magnitude of pain based on a brainwave of an object being estimated, comprising: a measurement step for measuring a brainwave a plurality of times from the object being estimated to obtain a plurality of brainwaves; and an estimation step for estimating a relative magnitude of pain upon the measurement of a brainwave a plurality of times from an amplitude of the plurality of brainwaves based on linearity in a relationship between the amplitude of a brainwave and pain.

This program can also make a computer execute a pain estimation method for estimating a magnitude of pain of an object being estimated based on a brainwave of the object being estimated, comprising: a first measurement step for measuring a brainwave from the object being estimated sequentially inflicted with stimulation of a plurality of magnitudes to obtain brainwave data corresponding to stimulation of each magnitude; an identification step for identifying an upper limit value and a lower limit value of a brainwave amplitude of the object being estimated based on the brainwave data; a second measurement step for measuring a brainwave from the object being estimated to obtain object's brainwave data; and an estimation step for estimating a magnitude of pain corresponding to the object's brainwave data, based on a relative size of a value of amplitude of the object's brainwave data to the upper limit value and the lower limit value.

In this manner, the inventor has elucidated that brainwave data or analysis data thereof (e.g., amplitude) and pain have a specific relationship and explained that various embodiments can be designed as a result of analyzing the relationship between pain levels from evaluating a plurality of types of pain by a plurality of methods and brainwave data or analysis data thereof (e.g., amplitude value). In addition, the inventor has found that it is possible to calculate a pain classifier for estimating a magnitude of pain by fitting to a pain function based on the specific relationship between brainwave data or analysis data (e.g., amplitude) and pain.

(Pain Classifier Generation)

In one aspect, the present invention provides a method of generating a pain classifier for classifying pain of an object being estimated based on a brainwave of the object being estimated. This method comprises the steps of: a) stimulating the object being estimated with a plurality of levels of stimulation intensities; b) obtaining brainwave data (also referred to as brain activity data, amount of brain activity or the like, such as brainwave amplitude data ("EEG amplitude"), frequency property, and the like) of the object being estimated corresponding to the stimulation intensities; c) plotting, and fitting to a pain function such as a linear function with a linear approximation of the modulation range or a more comprehensive sigmoid function pattern encompassing the same, the stimulation intensities or a subjective pain sensation level corresponding to the stimulation intensities and the brainwave data to obtain a pain function specific to the object being estimated; and d) identifying a pain classifier for separating a pain level to at least two (strong, moderate, and week and the like is also possible) based on the specific pain function when a regression coefficient for fitting to the specific pain function is equal to or greater than a predetermined value.

Alternatively, the present invention provides an apparatus for generating a pain classifier for classifying pain of an object being estimated based on a brainwave of the object being estimated. This apparatus comprises A) a stimulation unit for stimulating the object being estimated with a plurality of levels of stimulation intensities; B) a brainwave data obtaining unit for obtaining brainwave data (e.g., amplitude data) of the object being estimated corresponding to the stimulation intensities; and C) a pain classifier generation unit for plotting, and fitting to a pain function such as a linear function with a linear approximation of the modulation range or a more comprehensive sigmoid function pattern encompassing the same, the stimulation intensities or a subjective pain sensation level corresponding to the stimulation intensities and the brainwave data to obtain a pain function specific to the object being estimated, and identifying a pain classifier for separating a pain level to at least two based on the specific pain function. Typically, step a) is performed at the A) stimulation unit, step b) is performed at the B) brainwave data obtaining unit, and step c) and step d) are performed at the C) pain classifier generation unit.

In the present invention, pain can be "estimated" or "determined" by "classification". It is understood that if pain can be found to be strong or weak by "pain classification", an operation can be administered so that strong stimulation is not inflicted, and an effect of objectively finding a therapeutic effect of an analgesic or the like is attained. If "strong stimulation" can be estimated from "weak stimulation", and "whether not weak pain is felt" can be estimated as "increase in frequency of appearance of an amount characteristic of deviation=pain is intensifying" if the variation range of characteristic amount of brain activity associated with weak pain can identified. Since there is no label of what level of pain a patient feels as strong in actual settings, it is preferable to provide reference stimulation from weak pain to about the middle of a modulation point to identify a pattern of change in brain activity. Based thereon, pain can be estimated from brain activity of the patient to determine the status of pain. If a "variation range of the characteristic amount of brain activity associated with weak pain" can be found, it can be estimated that "non-weak pain is felt" when the frequency of deviating from the range increases.

Figure 23:
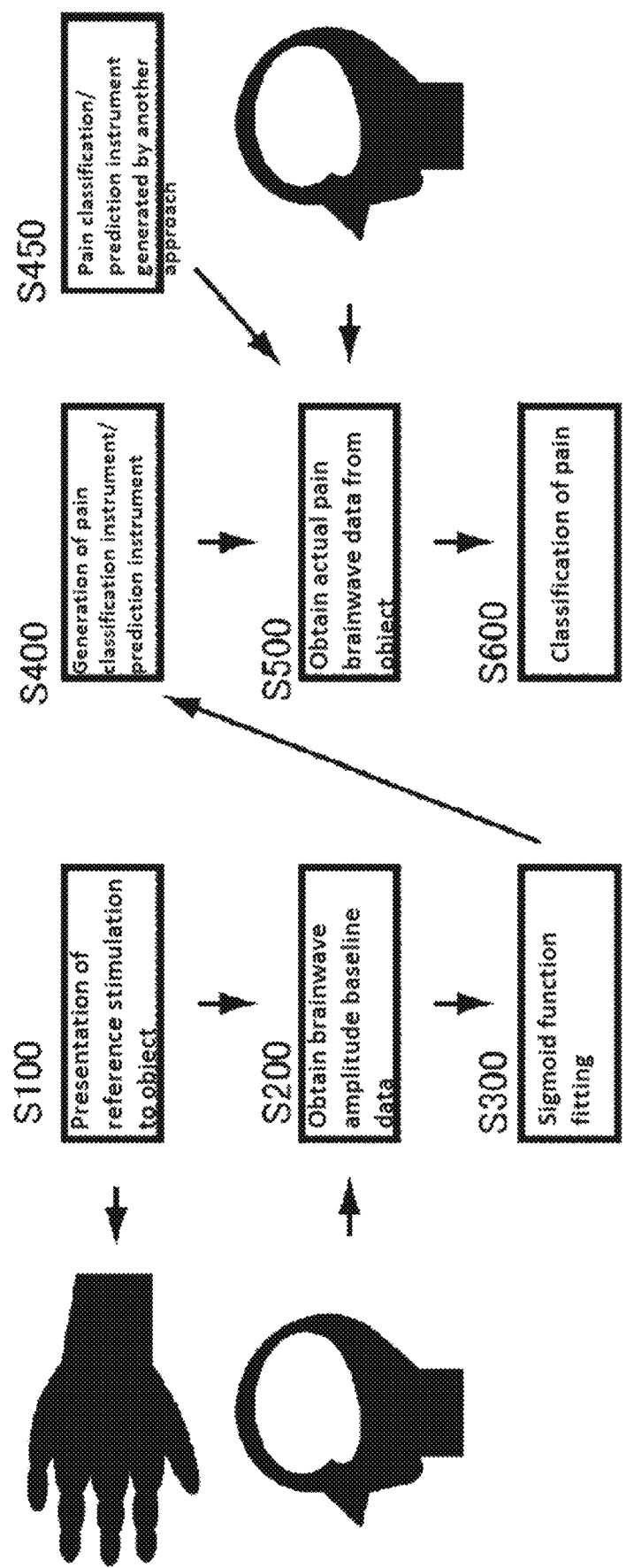
FIG. 23 is an example of a flow chart depicting the flow of the invention.

A schematic diagram is used hereinafter to explain the approach for generating a pain classifier (FIG. 23).

In the step (S100) for stimulating the object being estimated with a plurality of levels of stimulation intensities of step a), the object being estimated is stimulated with a plurality of levels (intensity of magnitude) of stimulation (e.g., cold temperature stimulation, electrical stimulation, or the like). The number of stimulation intensities can be a number required for fitting to a pain function, e.g., at least three is generally required. Even if the number is 1 or 2, fitting to a pain function can be possible by combining this with information obtained in advance. Thus, this number is not necessarily required. Meanwhile, for new fitting, it can be advantageous to stimulate with generally at least 3, preferably 4, 5, 6, or more levels of stimulation. In this regard, burden on an object being estimated should be minimized, so that a number of stimulation intensities that is highly invasive to the object being estimated (in other words, intensity that is unbearable to a subject) is preferably at a minimum or zero. Meanwhile, highly invasive stimulation to an object being estimated can be necessary for more accurate fitting, so that a minimum number can be included in accordance with the objective. For example, the number of such highly invasive levels of stimulation can be at least 1, at least 2, or at least 3, or 4 or more if tolerable by the object being estimated.

Step b) is a step of obtaining brainwave data (also referred to as brain activity data, amount of brain activity or the like, such as amplitude data ("EEG amplitude"), frequency property, or the like) of the object being estimated corresponding to the stimulation intensity (S200). Such brainwave data can be obtained using any method that is well known in the art. Brainwave data can be obtained by measuring an electrical signal of a brainwave and described in terms of potential (can be described by $\mu V$ or the like) as amplitude data or the like. The frequency property is described in terms of power spectrum density or the like.

In a preferred embodiment, the present invention is preferably practiced 1) with minimum number of electrodes (about 2), 2) by avoiding scalp with hair as much as possible, and 3) by a simple method that can record even while sleeping to obtain brainwave data, but the number of electrodes can be increased as needed (e.g., 3, 4, 5, or the like)

Step c) is a step for plotting, and fitting to a pain function (linear function or sigmoid curve), the stimulation intensities and the brainwave data to obtain a pain function specific to the object being estimated (S300).

This step creates a plotted diagram using stimulation intensities used in step a) and brainwave data obtained in step b) which is fitted to a pain function. Fitting to a pain function can be performed using any approach that is known in the art. In addition to linear functions, specific examples of such a fitting function include, but are not limited to, Boltsmann function, double Boltsmann function, Hill function, logistic dose response, sigmoid Richards function, sigmoid Weibull function, and the like. Among them, standard logistic functions are called sigmoid functions, and standard functions or modified forms are common and preferred.

Step d) is a step for identifying a pain classifier for separating a pain level to at least two (or a pain level to 2, 3 or more quantitative or qualitative levels) based on the pain function when a regression coefficient for fitting to the pain function is equal to or greater than a predetermined value as needed (S400). A pain classifier can be identified and determined based on an inflection point (median value or the like) of a pain function, but this is not a limiting example. A pain classifier can be calibrated so that the classification of a pain level is maximized as needed. For example, brainwave data corresponding to an inflection point of a pain function can be temporarily determined as a pain classifier. This pain classifier can be calibrated so that the original brainwave data and stimulation intensity corresponding thereto or subjective pain sensation level of an object corresponding to the stimulation intensity is actually evaluated to keep outliers low or preferably to minimize outliers. Such a pain classifier can be applied to calculate or classify pain levels and utilized in determining therapeutic effects.

If the same subject is subjected to estimation, the process can include a step of keeping or updating a classifier by using the previous classifier data.

In the apparatus for generating a pain classifier of the invention, A) a stimulation unit for stimulating the object being estimated at a plurality of levels of stimulation intensities is configured to perform step a), i.e., has means or function capable of providing a plurality of stimulation intensities. In addition, the stimulation unit is configured to be able to inflict such stimulation to an object.

B) a brainwave data obtaining unit for obtaining brainwave data (e.g., amplitude data) or analysis data thereof of the object being estimated corresponding to the stimulation intensities is configured to obtain brainwave data or analysis data thereof of an object being estimated. A brainwave data obtaining unit can have other functions (e.g., step e) in a classification apparatus) in addition to performing step b).

C) a pain classifier generation unit for plotting, and fitting to a pain function such as a linear function with a linear approximation of the modulation range or a more comprehensive sigmoid function pattern encompassing the same, the stimulation intensities or a subjective pain sensation level corresponding to the stimulation intensities and the brainwave data to obtain a pain function specific to the object being estimated, and identifying a pain classifier for separating a pain level to at least two based on the specific pain function can have a function of fitting to a calculated specific pain function and generating a pain classifier. Generally, C) a pain classifier generation unit performs step c) and step d). These two functions can be materialized in separate apparatuses, devices, CPU, terminals or the like, or as one unit. In general, a CPU or a calculating apparatus is configured so that a program for materializing such calculation is integrated or capable of being integrated.

Figure 24:
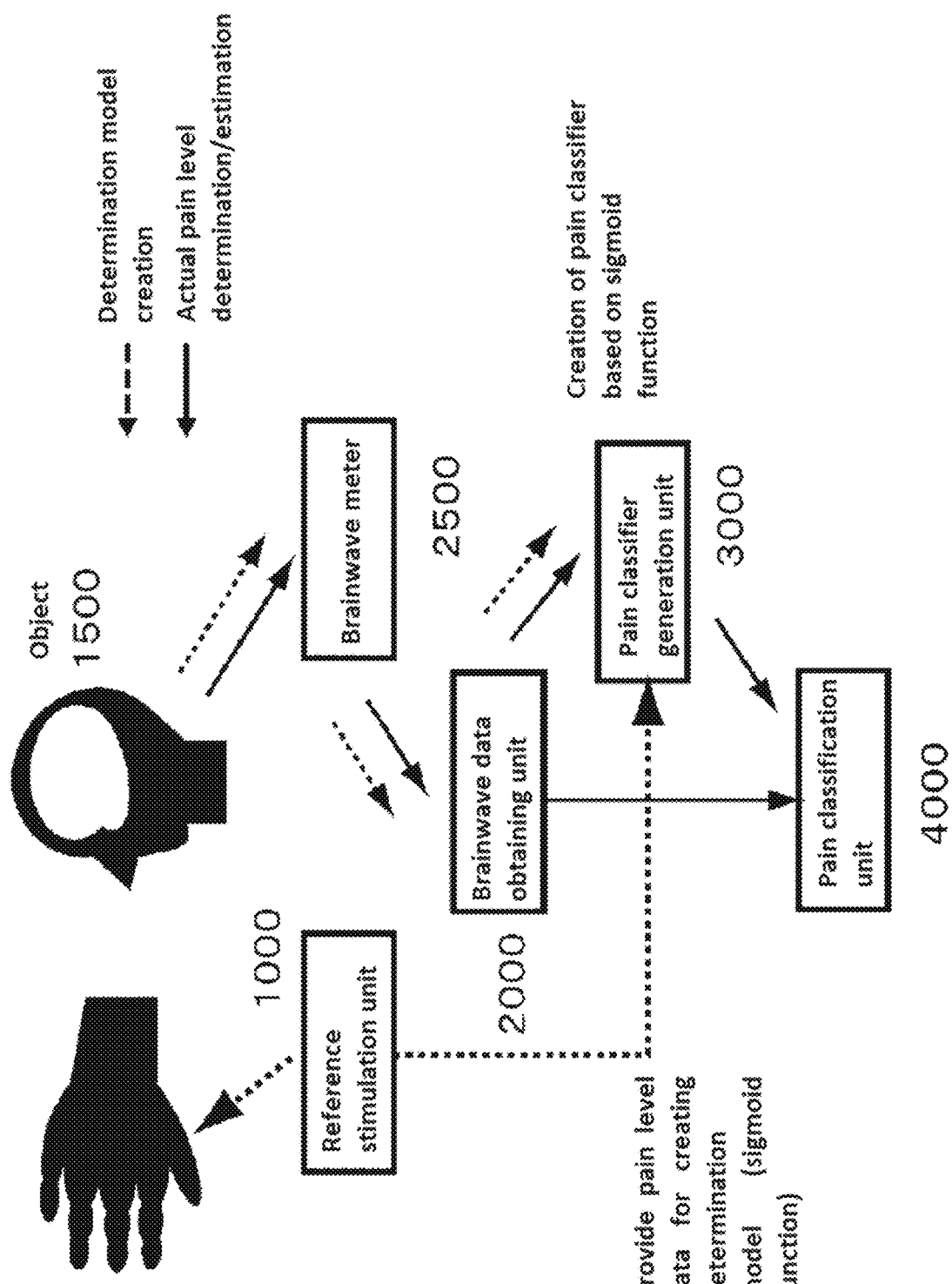
FIG. 24 is an example of a block diagram depicting the functional configuration of the invention.

FIG. 24 describes a schematic diagram of the apparatus of the invention. Since this embodiment is a pain classifier measurement apparatus therein, 1000 to 3000 are involved. The stimulation unit 1000 corresponds to A), where a value of stimulation is communicated to a brainwave data obtaining unit 2000 and a pain classifier generation unit 3000. The brainwave data obtaining unit 2000 is configured (2500) to comprise or to be linked to a brainwave meter that is or can be linked to a subject (1500) so that brainwave data or analysis data thereof from stimulation emanated from a reference stimulation unit to the subject (1500) can be obtained.

Figure 25:
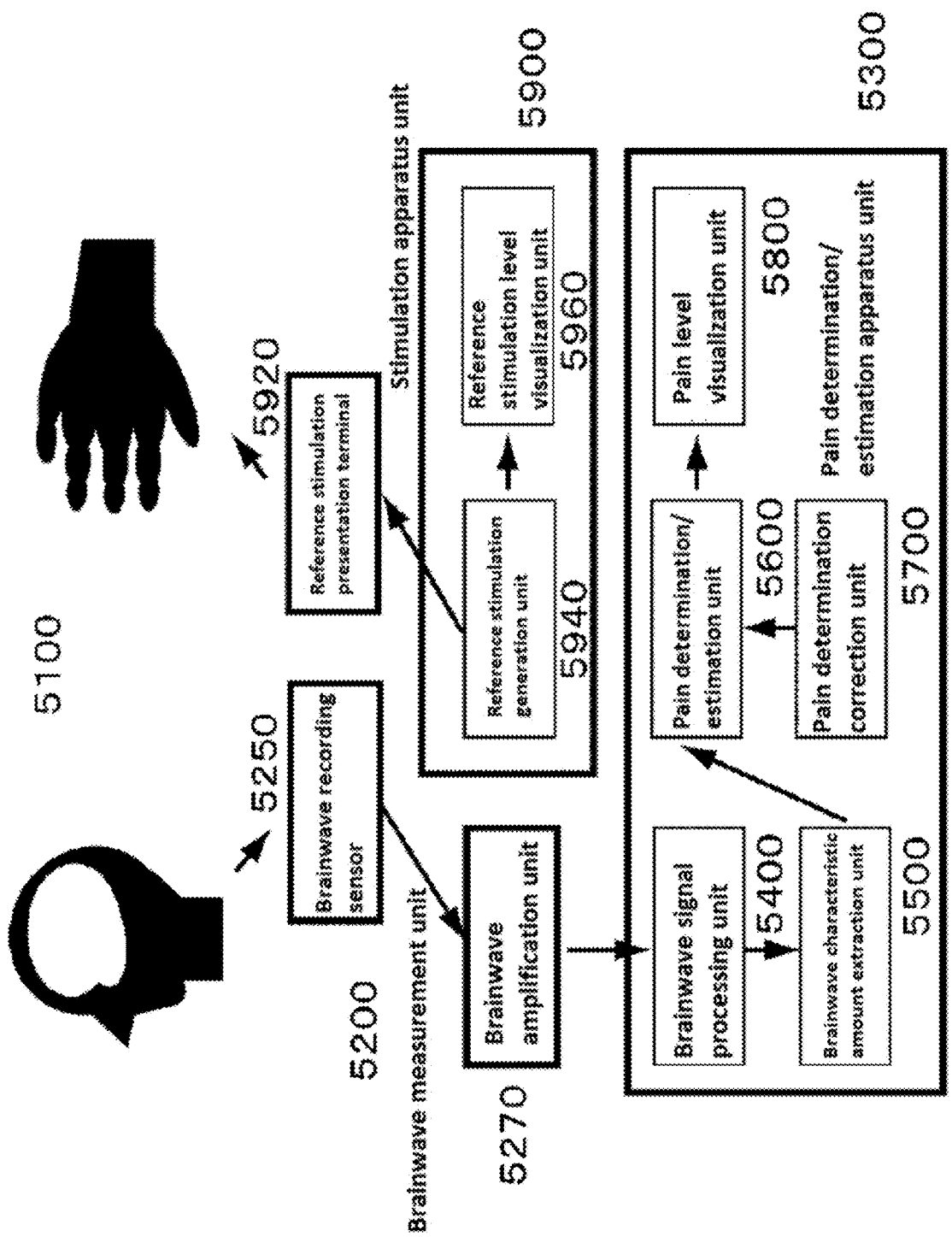
FIG. 25 is an example of a block diagram depicting the functional configuration of the invention.

FIG. 25 is a block diagram depicting the functional configuration of a pain estimation or pain classification or pain classifier generation system 5100 in one embodiment (it should be noted that some parts of the configurational diagrams are optional configurational units that can be omitted). The system 5100 comprises a brainwave measurement unit 5200, which internally comprises, or externally connects to, a brainwave recording sensor 5250 and optionally a brainwave amplification unit 5270, and processes pain signals and determines/estimates pain at a pain determination/estimation apparatus unit 5300. The pain determination/estimation apparatus unit 5300 processes a brainwave signal at a brainwave signal processing unit 5400, (if necessary extracts a characteristic amount of brainwave at a brainwave characteristic amount extraction unit 5500), estimates/determines pain at a pain determination/estimation unit 5600, and (optionally) visualizes pain with a pain level visualization unit 5800. The system also comprises a stimulation apparatus unit 5900 inside or outside. The stimulation apparatus unit 5900 comprises a reference stimulation presentation apparatus unit (terminal) 5920, contributing to creation of a pain classification instrument for a patient. The stimulation apparatus unit can optionally comprise a reference stimulation level visualization unit 5960 comprising a reference stimulation generation unit 5940.

Such a pain classifier generation system 5100 comprises the brainwave measurement unit 5200 and the pain determination/estimation apparatus unit estimation unit 5300, and optionally comprises the stimulation apparatus unit 5900 (can include a reference stimulation unit). The pain determination/estimation apparatus unit 5300 is materialized, for example, by a computer comprising a processor and a memory. In such a case, the pain determination/estimation apparatus unit estimation unit 5300 makes the processor function as the brainwave amplification unit 5270 as needed, brainwave signal processing unit 5400, pain determination/estimation unit 5600 (as needed), pain level visualization unit 5800 (as needed) or the like when a program stored in the memory is executed by the processor. The processor is also made to perform reference stimulation generation and visualization as needed. The system 5100 and the apparatus unit 5300 of the invention can be materialized, for example, by a dedicated electronic circuit. A dedicated electronic circuit can be a single integrated circuit or a plurality of electrical circuits. The brainwave data obtaining unit and the pain classifier generation unit can have the same configuration as the pain estimation apparatus.

The brainwave measurement unit 5200 obtains a plurality of brainwave data by measuring a brainwave a plurality of times from an object being estimated via a brainwave meter (brainwave recording sensor 5250). An object being estimated is an organism generating a change in a brainwave by pain, which does not need to be limited to humans.

The pain determination/estimation unit 5600 generates a pain classifier. A pain classifier is used for estimating or classifying a magnitude of pain from amplitudes of a plurality of brainwave data. In other words, the pain determination/estimation unit 5600 can generate a pain classifier for estimating or classifying pain of an object from brainwave data.

The brainwave recording sensor 5250 measures electrical activity generated in the brain of an object being estimated with electrodes on the scalp. In addition, the brainwave recording sensor 5250 outputs brainwave data, which is a result of measurement. The brainwave data can be amplified as needed.

Next, a method or a process of an apparatus configured in the above matter is explained. FIG. 23 is a flow chart depicting a series of processes. In this aspect, S100 to S400 are involved. In S400, a pain classifier (also referred to as a pain classification instrument/pain prediction instruction) is generated.

Stimulation of a plurality of levels (magnitudes) of stimulation intensities is inflicted on an object through a reference stimulation unit 1000 (S100).

Next, brainwave data (brainwave amplification baseline data such as amplitude data) is obtained (S200). Brainwave data is obtained by the brainwave data obtaining unit 2000 in FIG. 24. In terms of FIG. 25, a plurality of brainwave data are obtained by measuring a brainwave a plurality of times from an object being estimated by the brainwave measurement unit 5200 via the brainwave meter (brainwave recording sensor 5250) and is used as the brainwave data (e.g., amplitude data). The brainwave measurement unit 5200 can also measure brainwaves at a plurality of times.

The pain classifier generation unit 3000 (see FIG. 24) performs pain function fitting (S300). When pain function fitting is performed and a regression coefficient is optionally determined to be a suitable value, a pain classifier (pain classification instrument/pain prediction instrument) can be generated using the pain function (S400).

After a pain classifier is generated, the value can be calibrated as needed.

(Pain Classification/Estimation)

In another aspect, the present invention provides a method of classifying pain of an object being estimated based on a brainwave of the object being estimated. This method comprises the steps of: e) obtaining brainwave data or analysis data thereof (e.g., amplitude data) of the object being estimated; and f) classifying a pain level of the object being estimated by fitting the brainwave data or analysis data thereof to a predetermined pain classifier; wherein the pain classifier is obtained by fitting the brainwave data or analysis data thereof of the object being estimated to a pain function. Such a pain classifier can be calculated by any approach described in the section of (Pain classifier generation), but the value may be generated by another approach or pre-generated (FIG. 23, S450).

In another aspect, the present invention provides an apparatus for classifying pain of an object being estimated based on a brainwave of the object being estimated. This apparatus comprises: X) a brainwave data obtaining unit for obtaining brainwave data or analysis data thereof (e.g., amplitude data) of the object being estimated; and Y) a pain classification unit for classifying a pain level of the object being estimated based on a pain classifier or by fitting the brainwave data or analysis data thereof to the pain classifier, wherein the pain classifier is obtained by fitting the brainwave data of the object being estimated to a pain function. Generally, X) a brainwave data obtaining unit performs step e) and the Y) a pain classification unit performs step f), but this is non-limiting.

Step e) is a step for obtaining brainwave data (e.g., amplitude data) of the object being estimated (S500). This step is a step of obtaining brainwave data from an object to be measured regardless of whether some type of stimulation is inflicted or treated. This step can be any approach as long as it is an approach that can obtain brainwave data. The same approach for obtaining brainwave data used in step b) can be used, and the same approach is generally used.

Step f) is a step for classifying the brainwave data to a pain level of the object being estimated based on a predetermined pain classifier (S600). A predetermined pain classifier is referred to as a "pain classification instrument" or "pain prediction apparatus" in relation to a pain level of an object being estimated. For example, when brain amplitudes associated with pain exhibit a decreasing pattern and a pain classifier classifies pain into "strong pain" and "weak pain", pain is classified as "strong pain" when brainwave data (e.g., amplitude data) lower than this value is detected, and pain is classified as "weak pain" when greater brainwave data (e.g., amplitude data) is detected. For example, if the value of a pain classification instrument indicates a standardized brainwave absolute amplitude of "0.7", brainwave amplitude data recorded online is converted to an absolute value based on existing data and standardized, and then "0.8" is classified as sensing "weak pain", and "0.2" is classified as sensing "strong pain".

In one embodiment, brainwave data or analysis data thereof (e.g., amplitude data) is fitted to the pain classifier with a mean value. Such a mean value can be 15 to 200 seconds, or a mean value exceeding 200 seconds (e.g., 300 seconds, 500 seconds, 600 seconds, 900 seconds, 1200 seconds, or the like) when data is recorded over several hours.

This aspect is explained based on FIG. 24. In FIG. 24, the brainwave data obtaining unit 2000 as well as the pain classification unit 4000 are referenced. The dotted lines indicate procedures of creating a determination model, and solid lines indicate the procedures of determining/estimating actual pain levels. In such a case, as explained in the section (Pain classifier generation), brainwave data can be obtained via a brainwave meter from an object. In other words, the brainwave data obtaining unit 2000 is configured (2500) to be linkable to the object 1500, and the brainwave data obtaining unit 2000 is configured to comprise or to be linked to a brainwave meter that is or can be linked to the object (1500) so that brainwave data or analysis data thereof obtained from the object (1500) can be obtained. The pain classification unit 4000 is configured to store a pain classifier in advance or receive data generated separately, and optionally configured to enable reference. Such a configuration of linking can be wired or wireless. A pain classifier that is stored in advance is generated based on fitting a characteristic amount to a pain function in the pain classifier generation unit 3000.

FIG. 25 is a block diagram depicting the functional configuration of a pain estimation or pain classification or pain classifier generation system 5100 in one embodiment. The system 5100 comprises the brainwave measurement unit 5200, which comprises the brainwave recording sensor 5250 and optionally internally comprises, or externally connects to, the brainwave amplification unit 5270, and processes pain signals and determines/estimates pain at a pain determination/estimation apparatus unit 5300. The pain determination/estimation apparatus unit 5300 processes a brainwave signal at the brainwave signal processing unit 5400, (optionally) estimates/determines pain at the pain determination/estimation unit 5600, and (optionally) visualizes pain with the pain level visualization unit 5800. The system comprises the stimulation apparatus unit 5900 inside or outside. The stimulation apparatus unit 5900 comprises the reference stimulation presentation apparatus unit (terminal) 5920, contributing to creation of a classification instrument for a patient. The stimulation apparatus unit (optionally) comprises the reference stimulation generation unit 5940.

In this manner, the pain classifier generation system 5100 comprises the brainwave measurement unit 5200 and the pain determination/estimation apparatus unit 5300. The pain determination/estimation apparatus unit 5300 is materialized, for example, by a computer comprising a processor and a memory. In such a case, the pain determination/estimation apparatus estimation unit 5300 makes the processor function as the brainwave amplification unit 5270 as needed, brainwave signal processing unit 5400, pain determination/estimation unit 5600 (as needed), pain level visualization unit 5800 (as needed) or the like when a program stored in the memory is executed by the processor. The processor can also be made to perform reference stimulation generation and visualization as needed. The system 5100 and the apparatus unit 5300 of the invention can be materialized, for example, by a dedicated electronic circuit. A dedicated electronic circuit can be a single integrated circuit or a plurality of electrical circuits.

The brainwave data measurement unit and the pain classifier generation unit 3000 (see FIG. 24) can have the same configuration as the pain estimation apparatus or configured to be an external unit.

The brainwave measurement unit 5200 obtains a plurality of brainwave data by measuring a brainwave a plurality of times from an object being estimated via a brainwave meter (brainwave recording sensor 5250). An object being estimated is an organism generating a change in a brainwave by pain (e.g., animals such as mammals such as primates), which does not need to be limited to humans.

The pain determination/estimation unit 5600 estimates or classifies a magnitude of pain from amplitudes of a plurality of brainwave data based on a pain classifier created by the pain classifier generation unit 3000 (see FIG. 24). In other words, the pain determination/estimation unit 5600 estimates or classifies pain of an object from brainwave data based on a pain classifier.

The brainwave recording sensor 5250 measures electrical activity generated in the brain of an object being estimated with electrodes on the scalp. In addition, the brainwave recording sensor 5250 outputs brainwave data, which is a result of measurement. The brainwave data can be amplified as needed.

Next, a method or a process of an apparatus configured in the above manner is explained. FIG. 23 is a flow chart depicting a series of processes. In this aspect, S400 to S600 can be involved. These are steps after a pain classifier (also referred to as a pain classification instrument/pain prediction instrument) is generated in S400. Alternatively, this is when a pain classifier is separately available (when such a value is previously obtained and stored or the like), and such a case starts from S450.

This pain classifier can be stored in advance in the pain classification unit 4000 after the creation thereof, or the pain classification unit 4000 can be configured to be able to receive value data. Alternatively, when the pain classifier generation unit 3000 is attached, the value can be stored in the generation unit and a storage medium can be provided separately. This value can also be received by communication.

Next, brainwave data is obtained from an object (S500). The same technique explained in S200 can be used to obtain such brainwave data to employ the same embodiment. However, it is not necessarily to use the same apparatus or device as S200, which can be the same or different.

Next, brainwave data (e.g., amplitude data) obtained in S500 is fitted to a pain classifier to classify pain corresponding to the brainwave data (S600). Such pain classification can be configured to display or speak a certain phrase (strong pain, weak pain, or the like) when a predetermined value is output. The actual value and pain classifier can be displayed together to allow a user (clinician) to review the values.

(Pain Classifier Generation and Classification/Estimation)

In another aspect, the present invention relates to a method and apparatus for performing both pain classifier generation (determination model creation) and classification/estimation (model application).

Thus, in this aspect, the present invention provides a method of classifying/estimating pain of an object being estimated based on a brainwave of the object being estimated. This method comprises the steps of: a) stimulating the object being estimated with a plurality of levels of stimulation intensities; b) obtaining brainwave data (e.g., amplitude data) of the object being estimated corresponding to the stimulation intensities; c) plotting, and fitting to a pain function such as a linear function with a linear approximation of the modulation range or a more comprehensive sigmoid function encompassing the same, the stimulation intensities or a subjective pain sensation level corresponding to the stimulation intensities and the brainwave data to obtain a pain function specific to the object being estimated; d) identifying a pain classifier for separating a pain level to at least two based on the specific pain function when a regression coefficient for fitting to the specific pain function is equal to or greater than a predetermined value; e) obtaining the brainwave data (e.g., amplitude data) of the object being estimated; and f) classifying a pain level of the object being estimated by fitting the brainwave data to a pain classifier. Each step is explained in the sections of (Pain classifier generation) and (Pain classification/estimation). Each step can be carried out by any embodiment or combination of the described matters therein.

In another aspect, the present invention provides an apparatus for classifying pain of an object being estimated based on a brainwave of the object being estimated. The apparatus comprises: A) a stimulation unit for stimulating the object being estimated with a plurality of levels of stimulation intensities; B) a brainwave data obtaining unit for obtaining brainwave data (e.g., amplitude data) of the object being estimated (obtains brainwave data corresponding to the stimulation intensities and actual brainwave data); C) a pain classifier generation unit for plotting, and fitting to a pain function, the stimulation intensities or a subjective pain sensation level corresponding to the stimulation intensities and the brainwave data to obtain a pain function specific to the object being estimated, and identifying a pain classifier for separating a pain level to at least two based on the specific pain function (linear function or sigmoid curve); and D) a pain classification unit for classifying a pain level of the object being estimated by fitting the brainwave data to a pain classifier or based on the pain classifier.

Each constituent unit is explained in the sections of "Pain classifier generation) and (Pain classification/estimation). Each step can be carried out by any embodiment or combination of the described matters therein.

Figure 26:
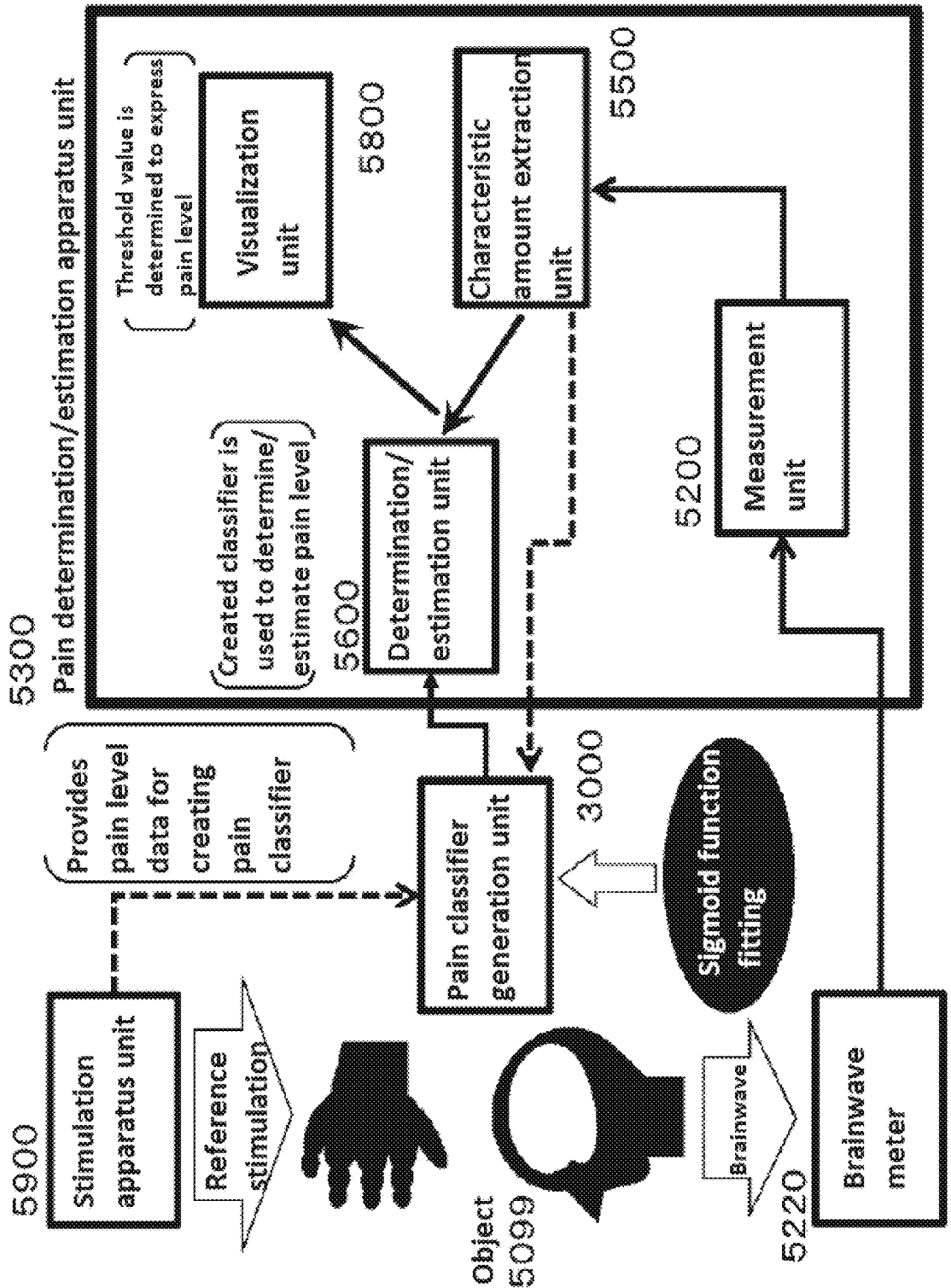
FIG. 26 is another example of a block diagram depicting the functional configuration of the invention.

An exemplary embodiment is explained based on FIG. 26.

FIG. 26 is a block diagram depicting the functional configuration of a system 5150 of the invention. In FIG. 26, functional blocks similar to FIG. 25 are assigned the same symbol, and explanation is appropriately omitted.

The system 5150 in this aspect comprises the pain determination/estimation apparatus unit 5300, the brainwave meter 5220 in the measurement unit 5200 (unlike the brainwave recording sensor 5250, this unit combines a sensor and an amplification unit), and the stimulation apparatus unit 5900 (can comprise a reference stimulation unit). The stimulation unit can have the same function as the stimulation unit 1000, can be a separate apparatus from the pain determination/estimation apparatus unit 5300 or can be integrated as a part thereof. The pain classifier generation unit 3000 is a unit for generating a pain classifier by obtaining a brainwave characteristic amount from the characteristic amount extraction unit 5500 and pain level information from the stimulation apparatus unit 5900 (can comprise a reference stimulation unit) and fitting to a sigmoid function, which is one form of a pain function. The pain classifier generation unit transmits a classifier to the estimation unit 5600.

The pain determination/estimation apparatus unit 5300 comprises an optionally integrated measurement unit 5200, estimation unit 5600, identification unit 5650, and optionally the visualization unit 5800. The pain determination/estimation apparatus unit 5300 is materialized, for example, by a computer comprising a processor and a memory. In such a case, the pain determination/estimation apparatus unit 5300 makes a processor function as at least 1, 2, 3, or all of, as needed, the measurement unit 5200, estimation unit 5600, visualization unit 5800, and when installed inside, the classifier generation unit 3000 when a program stored in the memory is executed by the processor. The pain determination/estimation apparatus unit 5300 can also be materialized by, for example, a dedicated electronic circuit. A dedicated electrical circuit can be a single integrated circuit or a plurality of electrical circuits.

The measurement unit 5200 measures a brainwave from an object being estimated 5099 sequentially inflicted with stimulation of a plurality of magnitudes to obtain brainwave data corresponding to stimulation of each magnitude via the brainwave meter 5220. The brainwave data is used in a process of fitting to a sigmoid function, which is one form of a pain function, and identifying a pain classifier.

Furthermore, the measurement unit 5200 obtains object's brainwave data by measuring a brainwave from the object being estimated 5099. The object's brainwave data is used in creating a pain classifier and in estimation process of a pain level. In other words, the pain determination/estimation apparatus unit 5300 estimates or classifies a value of magnitude of pain of the object being estimated 5099 based on a pain classifier when a brainwave for object's brainwave data is measured.

The determination/estimation unit 5600 estimates or classifies a value of magnitude of pain corresponding to object's brainwave data based on a pain classifier, based on the object's brainwave data or analysis data thereof (e.g., amplitude value) of the object being estimated 5099 identified by the classifier generation unit 3000. A classifier obtained by pain function (herein, an example includes a sigmoid function) fitting of the invention is introduced in the classifier generation unit.

The classifier generation unit 3000 identifies a pain classifier of the object being estimated 5099 based on brainwave data obtained by the measurement unit 5200. For example, the identification unit 5650 identifies an amplitude of a plurality of brainwave data corresponding to stimulation of a plurality of magnitudes. For example, the classifier generation unit 3000 can estimate or classify based on a pain classifier by analyzing a plurality of brainwave data or analysis data thereof. Specifically, the classifier generation unit 3000 can identify a pain classifier by fitting amplitudes of a plurality of brainwave data corresponding to a plurality of stimulation magnitudes to a pain function (herein, an example includes a sigmoid function). The visualization unit 5800 displays a pain level obtained by the determination/estimation unit 5600 temporally continuously or by points on a liquid crystal display or the like for monitoring pain.

The stimulation apparatus unit 5900 (can comprise a reference stimulation unit) inflicts stimulation of a plurality of magnitudes individually to the object being estimated 5099. Specifically, the stimulation apparatus unit 5900, for example, inflicts a plurality of magnitudes of stimulation sequentially to the object being estimated 5099 by changing the amount of stimulation. Stimulation is for example electrical stimulation, thermal stimulation, and the like. The stimulation apparatus unit 5900 (can comprise a reference stimulation unit) also provides information on pain levels to the pain classifier generation unit 3000.

Next, the process of the pain estimation/classification system 5150 configured in the above manner is explained. The processes of the system 5150 include an identification process for identifying an amplitude of a brainwave based on stimulation, a process for fitting to a pain function (herein, an example includes a sigmoid function) for generating a pain classifier, a process for generating a pain classifier, and a process for estimating or classifying pain from received brainwave data based on the pain classifier. First, the identification process is explained. FIG. 23 is referenced in this regard.

Stimulation of a plurality of levels (magnitude) of intensities is inflicted on an object through the stimulation unit 1000 (S100).

Next, brainwave data is obtained (S200). The brainwave data is obtained by the brainwave data obtaining unit 2000. In terms of FIG. 25, a plurality of brainwave data of analysis data thereof are obtained by measuring a brainwave a plurality of times from an object being estimated by the brainwave measurement unit 5200 via the brainwave meter (term collectively referring to a recording sensor and an amplification unit) 5220 and are used as the brainwave data for analysis The measurement unit 5200 can measure brainwaves at a plurality of times.

The pain classifier generation unit 3000 performs pain function fitting (S300). When pain function fitting is performed and a regression coefficient is optionally determined to be a suitable value, a pain classifier can be generated using the pain function (S400). After a pain classifier is generated, the value can be calibrated as needed to correct the classifier.

Such a pain classifier can be stored in the pain classification unit 4000 or the pain classifier generation unit 3000, or a storage medium can be provided separately. This value can also be transmitted/received by communication.

Next, brainwave data is obtained from an object (S500). The same technique explained in S200 can be used to obtain such brainwave data to employ the same embodiment. However, it is not necessary to use the same apparatus or device as S200, which can be the same or different.

Next, brainwave data or analysis data thereof (e.g., amplitude data) obtained in S500 is classified as pain corresponding to the brainwave data or analysis data thereof based on a pain classifier (S600). Such pain classification can be configured to display or speak a certain phrase (strong pain, weak pain, or the like) when a predetermined value is output. The actual value and pain classifier can be displayed together to allow a user (clinician) to review the value.

(Application of Pain Function)

The pain function used in the present invention has, when broadly defined, a linear relationship, in other words a one-to-one relationship, i.e., (i) first pain corresponding to first brainwave data or analysis data thereof (including, for example, amplitude) can be estimated to be greater than second pain corresponding to second brainwave data or analysis data thereof (including, for example, amplitude) if the first brainwave data is greater than the second brainwave data, and (ii) the first pain can be estimated to be less than the second pain if the first brainwave data or analysis data thereof (including, for example, amplitude) is less than the second brainwave data or analysis data thereof (including, for example, amplitude). It has been explained that any function that can express this can be used, and application examples thereof include linear functions and sigmoid functions. Since the end of an asymptote of the minimum value to the start of an asymptote of the maximum value can be partially taken out and approximated with a linear function, a sigmoid function can be understood as having a broadly defined linearity as a pain function of the invention and utilized as a pain function. In such a case, the modulation range of a sigmoid function can be considered as having "linearity" (see FIG. 27). FIG. 27 depicts a schematic diagram of a linearly approximated portion of a sigmoid function. Such linearity is significant not only as just a form of function patterns, but also in terms of reflecting "pain sensitivity property" of an individual due to a difference in the width of the modulation range and amplitude of modulation. For example, some people have the potential to exhibit slow continuity with gradual modulation, while others have the potential to exhibit a step function pattern of instant modulation. In this regard, identification of such a pain function of modulation (e.g., slope of linear function) is considered meaningful in determining pain.

Figure 28:
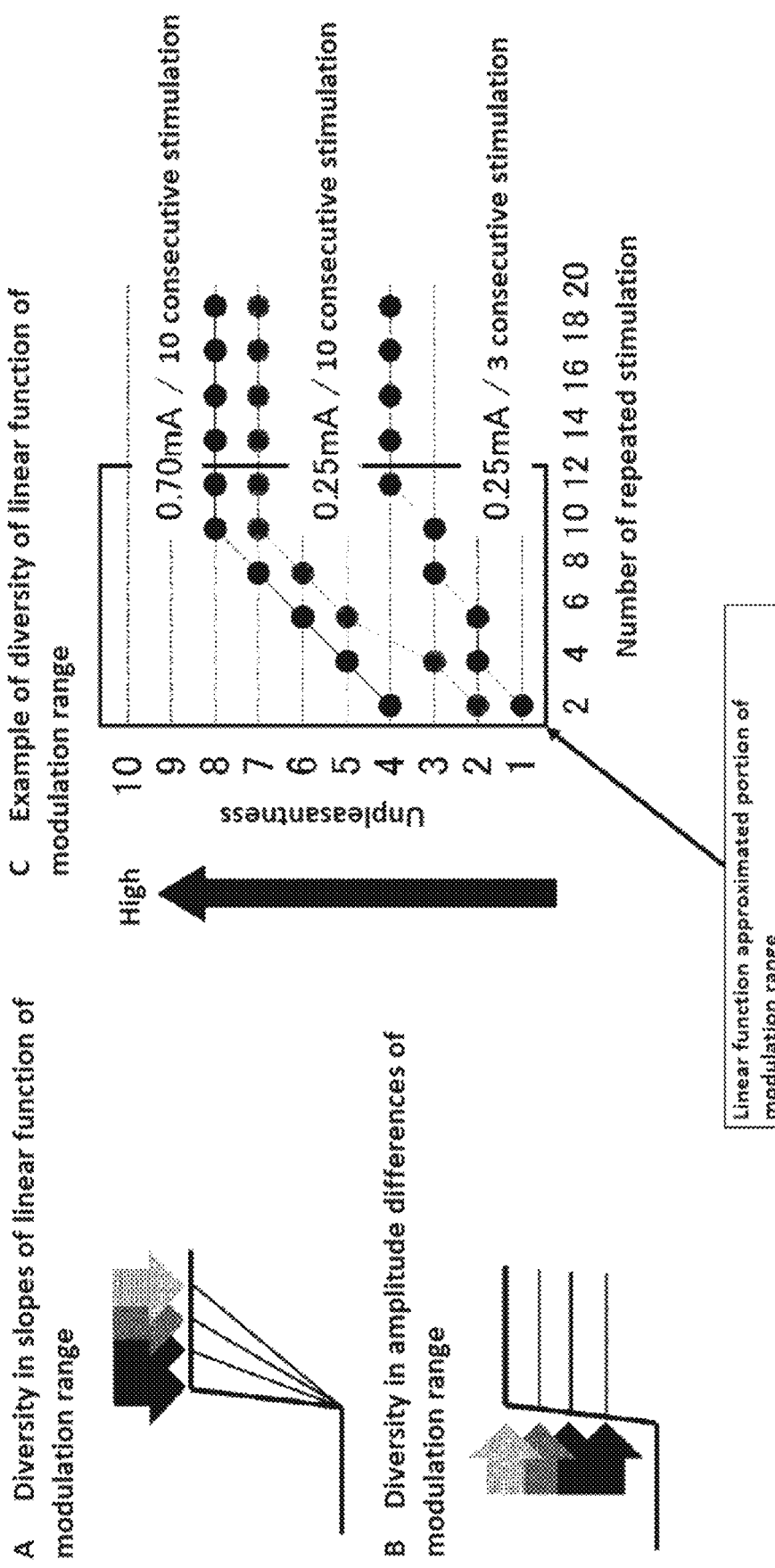
FIG. 28 shows diversity of linearity in the modulation range in a sigmoidal pain function in analytical schematic diagram of the invention. A shows the diversity of the slope of a linear function in the modulation range, and B shows the diversity of amplitude differences in the modulation range. C shows an example of a change in linearity in the modulation range observed when a pain stimulation presenting method has been changed with one subject.

The linearly approximated portion of a sigmoid function depicted in FIG. 27 is further explained. As depicted therein, the linearly approximated portion of a sigmoid function for unpleasantness can vary depending on the stimulation intensity even among individuals. A pattern of change in the pain characteristic amount of an individual can be predicted from such a property. For example, an object with a low slope can be left alone for a while even when a characteristic amount of pain starts to change, but an individual with a steep slope is envisioned to require immediate clinical attention or the like (see FIG. 28).

Other Embodiments

The pain classifier generation technologies according to one or more embodiments of the invention have been explained above based on the embodiments, but the present invention is not limited to such embodiments. Various modifications applied to the present embodiments and embodiments constructed by combining constituent elements in different embodiments conceivable to those skilled in the art without departing from the intent of the inventions are also encompassed within the scope of one or more embodiments of the invention.

For example, each of the above embodiments used a peak-to-peak value as the amplitude value of brainwave data, but amplitude values are not limited thereto. For example, a simple peak value can be used as the amplitude value.

The above embodiment of the invention for generating a pain classifier has set the range of values of magnitude of pain so that the value Pmax of the magnitude of pain corresponding to the upper limit value Amax of a brainwave amplitude is 1, and the value Pmin of the magnitude of pain corresponding to the lower limit value Amin of the brainwave amplitude is 0, but this is not a limiting example. For example, the magnitude of pain can be represented by 0 to 100. In such a case, the determination/estimation unit 5600 can estimate the value Px of magnitude of pain by the following equation.

$$Px = Pmax \times (Ax - Amin)/(Amax - Amin)$$

Curve fitting was explained above as an example of generating a pain classifier by analyzing a plurality of brainwave data, but this is not a limiting example. For example, a value corresponding to large stimulation can be identified using a learning model for estimating a brainwave amplitude for large stimulation from a brainwave amplitude corresponding to small stimulation. In such a case, large stimulation does not need to be inflicted upon an object being estimated, so that physical burden on the object being estimated can be alleviated. Further, a predetermined value can be used as the upper limit value of a brainwave amplitude. The predetermined value is for example 50 μV to 100 μV, which can be experimentally or empirically determined. In such normal analysis, data from about plus or minus 50 μV to 100 μV is eliminated as an artifact removal method. Such artifact removal can also be performed in the present invention as needed in pain classifier generation.

Stimulation inflicted upon the object being estimated 5099 by the stimulation apparatus 5900 (can comprise a reference stimulation unit) is not limited to electrical stimulation and thermal stimulation. Any type of stimulation can be inflicted as long as the magnitude of pain sensed by the object being estimated 5099 changes in accordance with the magnitude of stimulation.

Some or all of the constituent elements of the pain estimation apparatus in each of the above embodiments can be comprised of a single system LSI (Large Scale Integration). For example, the determination/estimation apparatus unit 5300 can be comprised of system LSI optionally having the measuring unit 5200 and optionally the stimulation apparatus 5900 (can comprise a reference stimulation unit).

System LSI is ultra-multifunctional LSI manufactured by integrating a plurality of constituents on a single chip, or specifically a computer system comprised of a microprocessor, ROM (Read Only Memory), RAM (Random Access Memory) and the like. A computer program is stored in a ROM. The system LSI accomplishes its function by the microprocessor operating in accordance with the computer program.

The term system LSI was used herein, but the term IC, LSI, super LSI, and ultra LSI can also be used depending on the difference in the degree of integration. The approach for forming an integrated circuit is not limited to LSI, but can be materialized with a dedicated circuit or universal processor. After the manufacture of LSI, a programmable FPGA (Field Programmable Gate Array) or reconfigurable process which allows reconfiguration of connection or setting of circuit cells inside the LSI can be utilized.

If a technology of integrated circuits that replace LSI by advances in semiconductor technologies or other derivative technologies becomes available, functional blocks can obviously be integrated using such technologies. Application of biotechnology or the like is also a possibility.

One embodiment of the invention can be not only such a pain classifier generation, pain determination/classification apparatus, but a pain classifier generation, pain determination/classification method using characteristic constituent units contained in the pain estimation apparatus as steps. Further, one embodiment of the invention can be a computer program for having a computer execute each characteristic step in the pain classifier generation, pain determination/classification method. Further, one embodiment of the invention can be a computer readable non-transient storage medium on which such a computer program is recorded.

In each of the above embodiments, each constituent element can be materialized by being configured with a dedicated hardware or by executing software program suited to each constituent element. Each constituent element can be materialized by a program execution unit such as a CPU or a processor reading out and executing a software program recorded on a storage medium such as a hard disk or semiconductor memory. In this regard, software materialized with the pain estimation apparatus of each of the above embodiments is a program such as those described below.

Specifically, this program makes a computer execute a pain determination method for estimating a magnitude of pain based on a brainwave of an object being estimated, comprising the steps of: a) stimulating the object being estimated with a plurality of levels of stimulation intensities; b) obtaining brainwave data (e.g., amplitude data) of the object being estimated corresponding to the stimulation intensities; c) plotting, and fitting to a pain function such as a linear function with a linear approximation of a modulation range or a more comprehensive sigmoid function encompassing the same, the stimulation intensities or a subjective pain sensation level corresponding to the stimulation intensities and the brainwave data to obtain a pain function specific to the object being estimated; d) identifying a pain classifier for separating a pain level to at least two based on the specific pain function when a regression coefficient for fitting to the specific pain function is equal to or greater than a predetermined value; e) obtaining the brainwave data (e.g., amplitude data) of the object being estimated; and f) classifying a pain level of the object being estimated by fitting the brainwave data to the pain classifier, and optionally converting and visualizing pain into a suitable pain indicator.

This program also makes a computer execute a method of generating a pain classifier based on a brainwave of an object being estimated, comprising the steps of: a) stimulating the object being estimated with a plurality of levels of stimulation intensities; b) obtaining brainwave data (also referred to as brain activity data, amount of brain activity, or the like, such as amplitude data (EEG amplitude), frequency property, or the like) of the object being estimated corresponding to the stimulation intensities; c) plotting, and fitting to a pain function such as a linear function with a linear approximation of a modulation range or a more comprehensive sigmoid function encompassing the same, the stimulation intensities or a subjective pain sensation level corresponding to the stimulation intensities and the brainwave data to obtain a pain function specific to the object being estimated; and d) identifying a pain classifier for separating a pain level to at least two based on the specific pain function when a regression coefficient for fitting to the specific pain function is equal to or greater than a predetermined value; or a method of classifying pain of an object being estimated based on a brainwave of the object being estimated, comprising the steps of: e) obtaining the brainwave data of the object being estimated; and f) classifying a pain level of the object being estimated by fitting the brainwave data to a predetermined pain classifier.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been explained while showing preferred embodiments to facilitate understanding. The present invention is explained hereinafter based on Examples. The above explanation and the following Examples are not provided to limit the present invention, but for the sole purpose of exemplification. Thus, the scope of the present invention is not limited to the embodiments or the Examples specifically described herein and is limited only by the scope of claims.

EXAMPLES

Examples are described hereinafter. The objects used in the following Examples were handled, as needed, in compliance with the standards of the Osaka University, and the Declaration of Helsinki and ICH-GCP in relation to clinical studies. While the products specifically described in the Examples were used for the reagents, equivalent products of other manufacturers can also be used instead.

Example 1: Generation of Pain Classifier

In this Example, a sigmoid function was used as a pain function to generate a pain classifier. The materials and methods are shown below.

(Materials and Methods)

(Participants)

72 healthy adult patients in their 20s to 70s participated in the Example. Informed consent was obtained from the participants prior to the clinical trial. All participants self-reported as never having undergoing a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Procedure) A temperature stimulation system (Pathway; Medoc Co., Ltd., Ramat Yishai, Israel) was used to inflict cold stimulation to the inside of the forearm of the participants. The test included six levels of temperature intensities. Under low temperature pain conditions, six temperature levels were linearly decreased by 5° C. in the range of −15° C. to 10° C. Each level consisted of three stimulations with a 5 second ISI (inter-stimulus interval). Each stimulation had 5 seconds of increase and maintained 15 seconds of plateau with a pseudo waiting period. The intervals between blocks were fixed at 100 seconds. The participants continuously evaluated pain intensities in the range of 0 to 100 (0: "no pain"; 100: "unbearable pain") on a computerized visual analog scale (COVAS). COVAS data was simultaneously recorded with changes in stimulation intensities.

(Electroencephalogram (EEG) Data Record)

Commercially available Bio-Amplifier (EEG 1200: Nihon Koden) was used to record EEG from four scalp Ag/AgCl scalp electrodes (Fz, Cz, C3, and C4). The frontmost electrode Fp1 was used for recording EOG activity. A reference electrode was attached to both earlobes, and an outside electrode was placed on the forehead. The sampling rate was 1000 Hz using a bandpass filter in the range of 0.3 to 120 Hz. The impedance of all electrodes was less than 15 kΩ.

(Electroencephalogram (EEG) Analysis)

Continuous EEG data was converted to 18 epoch data comprising 3 epochs in 6 temperature levels under low temperature pain conditions. Each epoch had a duration of 30 seconds after the start of stimulation. EOG artifacts were decreased based on the following regression filter.

[Numeral 1]

Raw EEG=β×EOG+C

EEG estimate=raw EEG−β×EOG

β: regression coefficient

C: intercept

EEG estimate: estimated EEG

Fp1 was the closest to the left eye and affected heavily by the eye movement, so that Fp1 data was used as EOG data. After VEOG was diminished, a baseline correction was applied separately to each intensity level. In other words, each epoch was corrected using a first epoch reference value from 5 seconds before the start of stimulation to the start of stimulation. The amplitudes corrected with the reference value were converted to an absolute value and averaged for each intensity level.

(Results)

One representative subject data is shown immediately below in order to show a sigmoid function between stimulation intensity and EEG activity.

Figure 15:
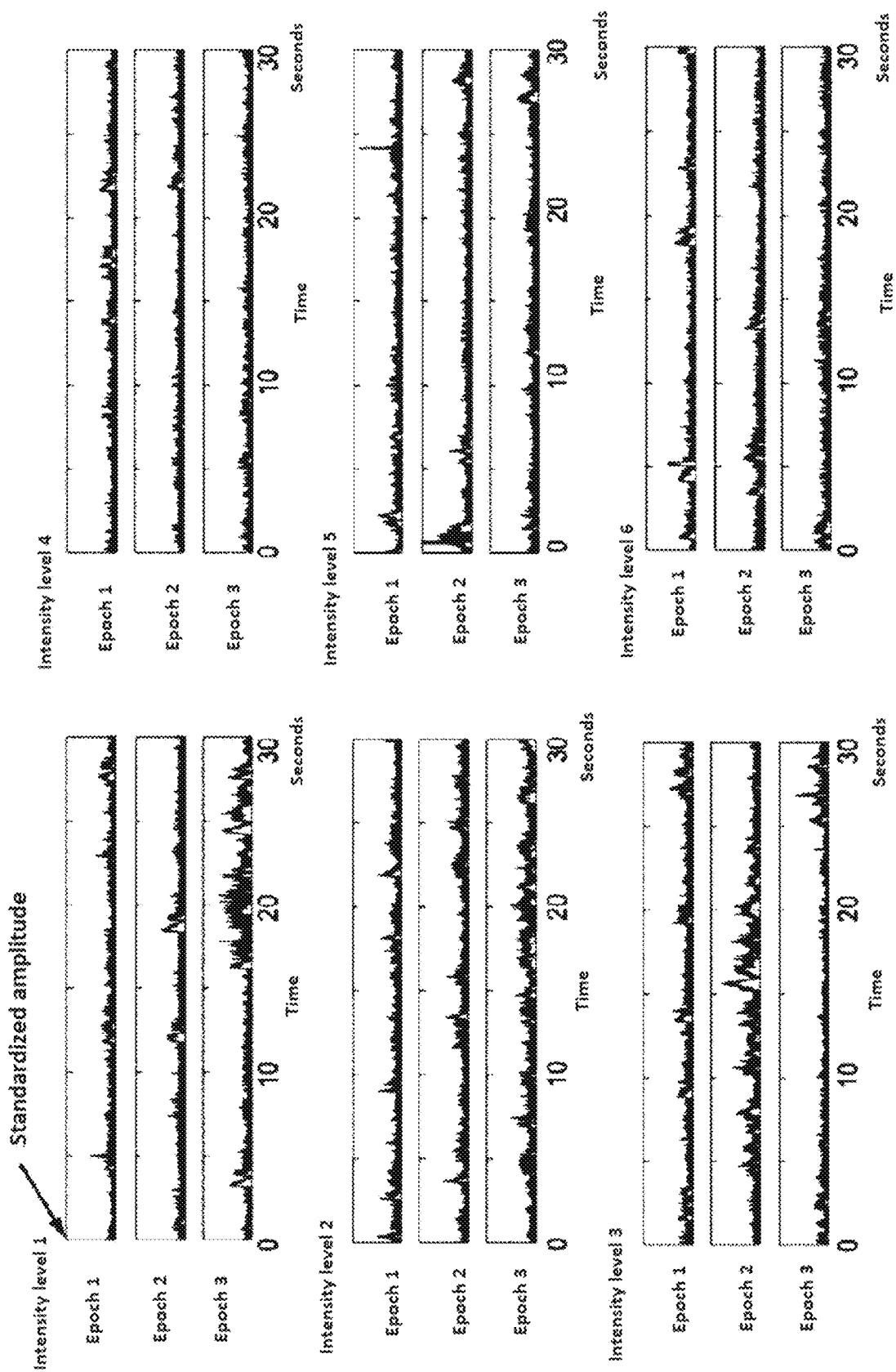
FIG. 15 shows a change in absolute amplitude over time in low temperature pain stimulation.

FIG. 15 represents absolute amplitude data (one subject) of 18 epochs associated with 6 intensity levels immediately before averaging for each level. The horizontal axis and vertical axis indicate time and standardized absolute amplitude, respectively. By observation, a change in amplitude in the three lower intensity levels (levels 1 to 3) is greater than a change in amplitude in the higher intensity levels (levels 4 to 6).

Figure 16:
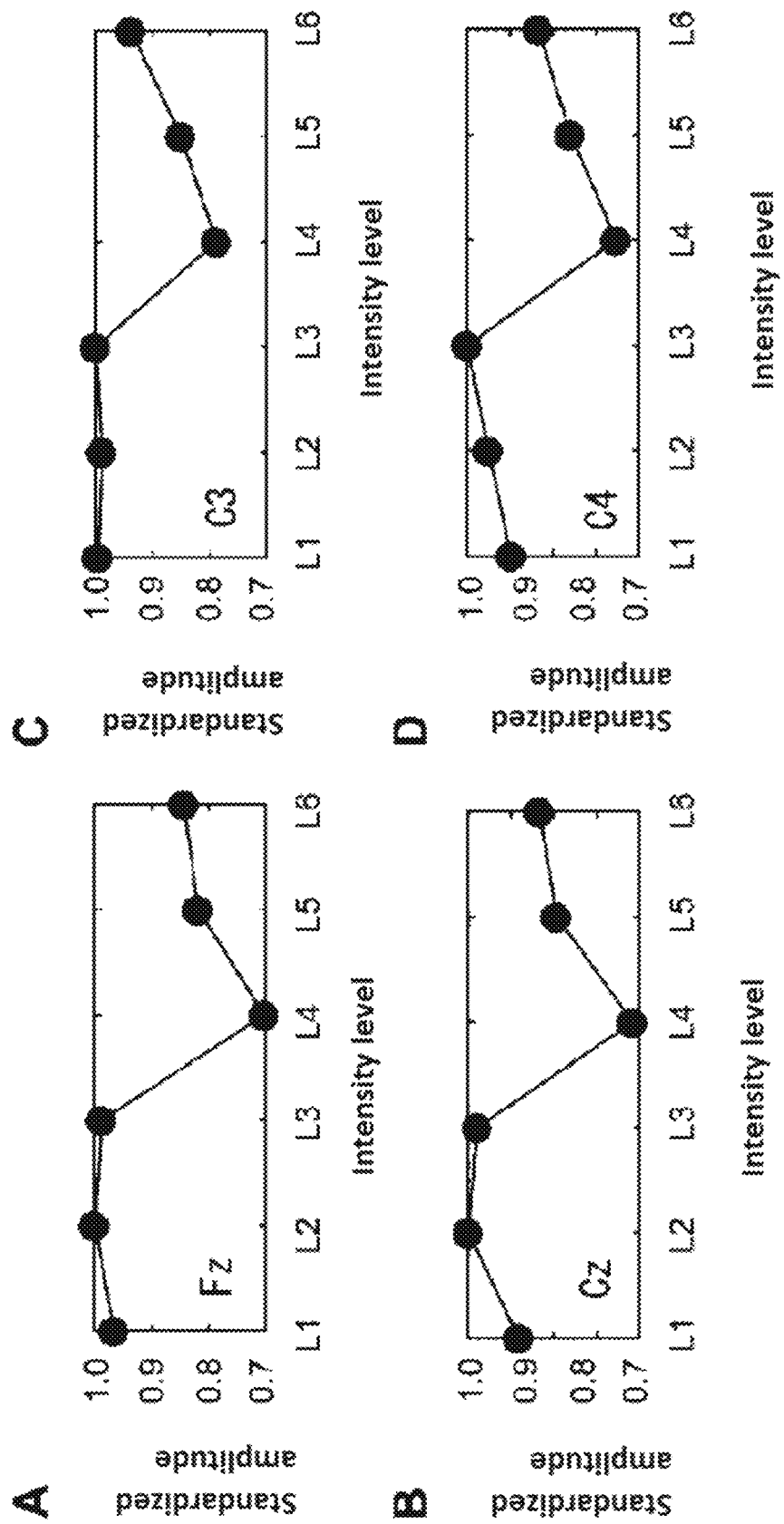
FIG. 16 shows an intensity-amplitude sigmoid function in low temperature pain stimulation.

FIG. 16 shows absolute amplitudes averaged from three epochs in each intensity level. Amplitudes are standardized with the maximum value. The horizontal and vertical axes indicate stimulation intensity and standardized amplitude, respectively. As can be observed in FIG. 16 (electrode position information is indicated by four plots), the mean amplitude more clearly shows that the lower intensity levels (levels 1 to 3) exhibit greater EEG amplitudes than the higher intensity levels (levels 4 to 6). This intensity-amplitude function is not a negative linear function, but a decreasing sigmoid function.

Figure 17:
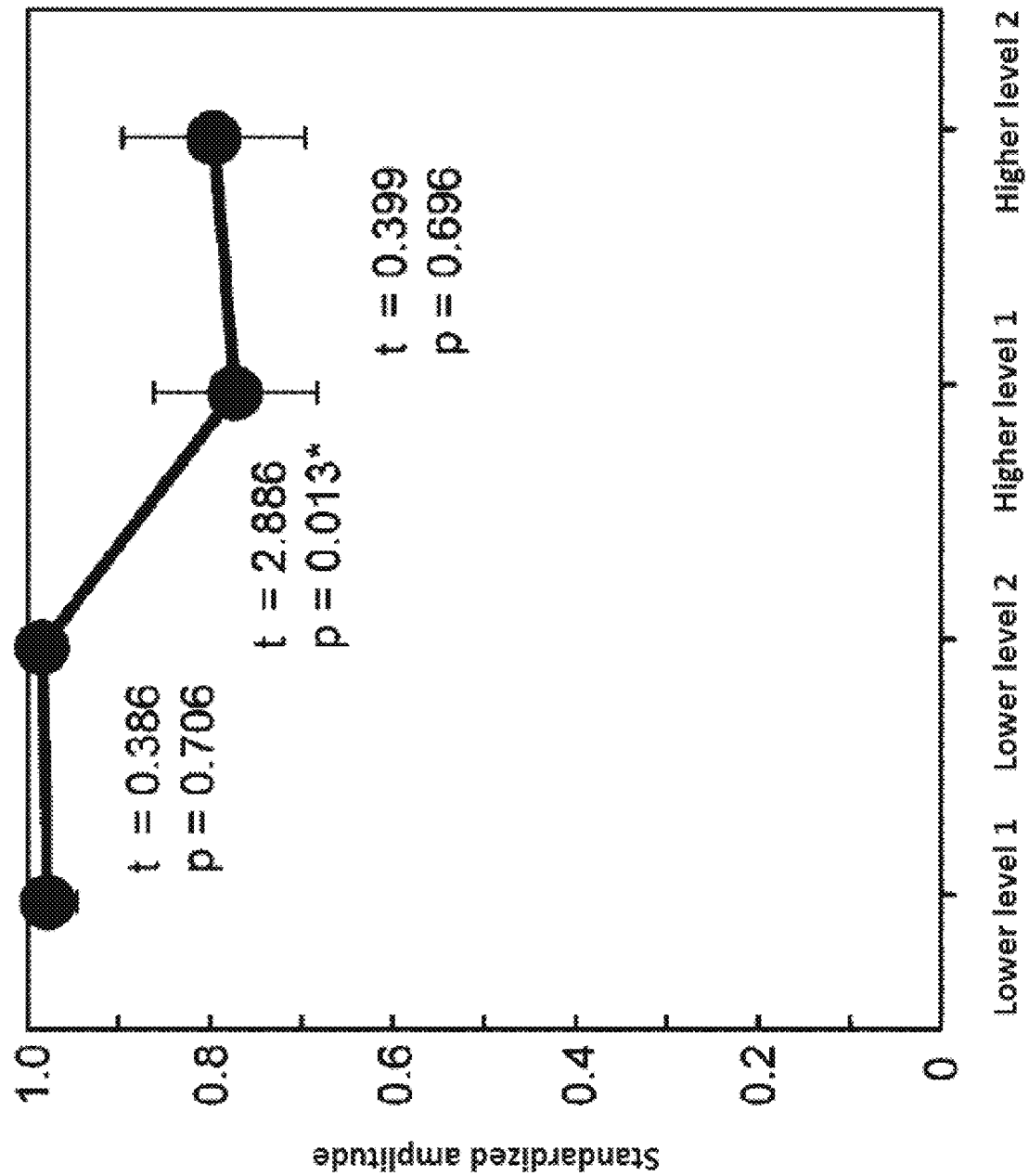
FIG. 17 shows a decreasing sigmoid function in a low temperature pain paradigm.

14 participants strictly exhibited a decreasing sigmoid function. Since a decrease in the start level of amplitude varies among participants and electrodes on individual participants, the inventor selected a suitable channel to identify four channels covering higher amplitude levels immediately before the start of the change and lower amplitude levels after the change. The overall mean of amplitudes in four levels was calculated, and statistical test was run between closely corresponding levels by a corresponding t-test. FIG. 17 clearly shows a decreasing sigmoid function between intensity level and amplitude, which is supported by a statistical result of lower level pain 2 and higher level pain 1 having statistically significantly different amplitudes (t=2.886, p=0.013). Fitting analysis indicated that this function significantly fits the following equation.

$$\text{Sigmoid function} = 0.9987 - 0.2211/(1+10^{((3.2722-x)\times 39.7591)})$$

x: EEG data standardized with maximum value

Figure 18:
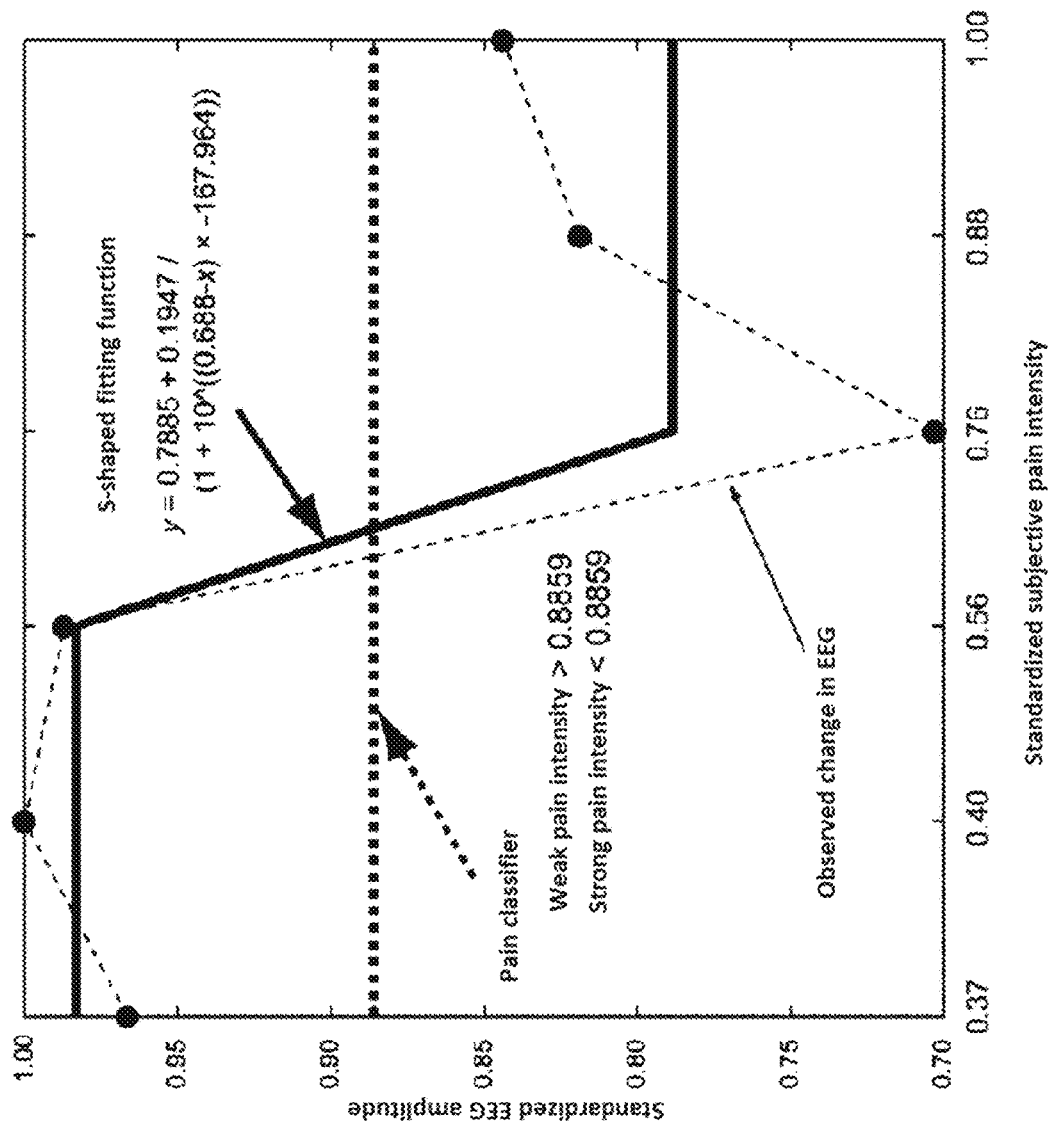
FIG. 18 shows a pain classifier based on a sigmoid fitting function.

The inventor generated a pain classifier for one patient as shown in FIG. 18 using a sigmoid fitting function. First, the inventor calculated the mean subjective pain evaluation value (x axis) and mean EEG amplitude (Fz: y axis) standardized with the maximum value. The inventor then estimated a sigmoid fitting function for these values to generate a pain classifier or a median value. In other words, standardized EEG activity exceeding a threshold value of pain classification (>0.8559) was labeled as "weaker pain intensity" and standardized EEG amplitudes below a threshold of pain classification was labeled "stronger pain intensity".

Figure 19:
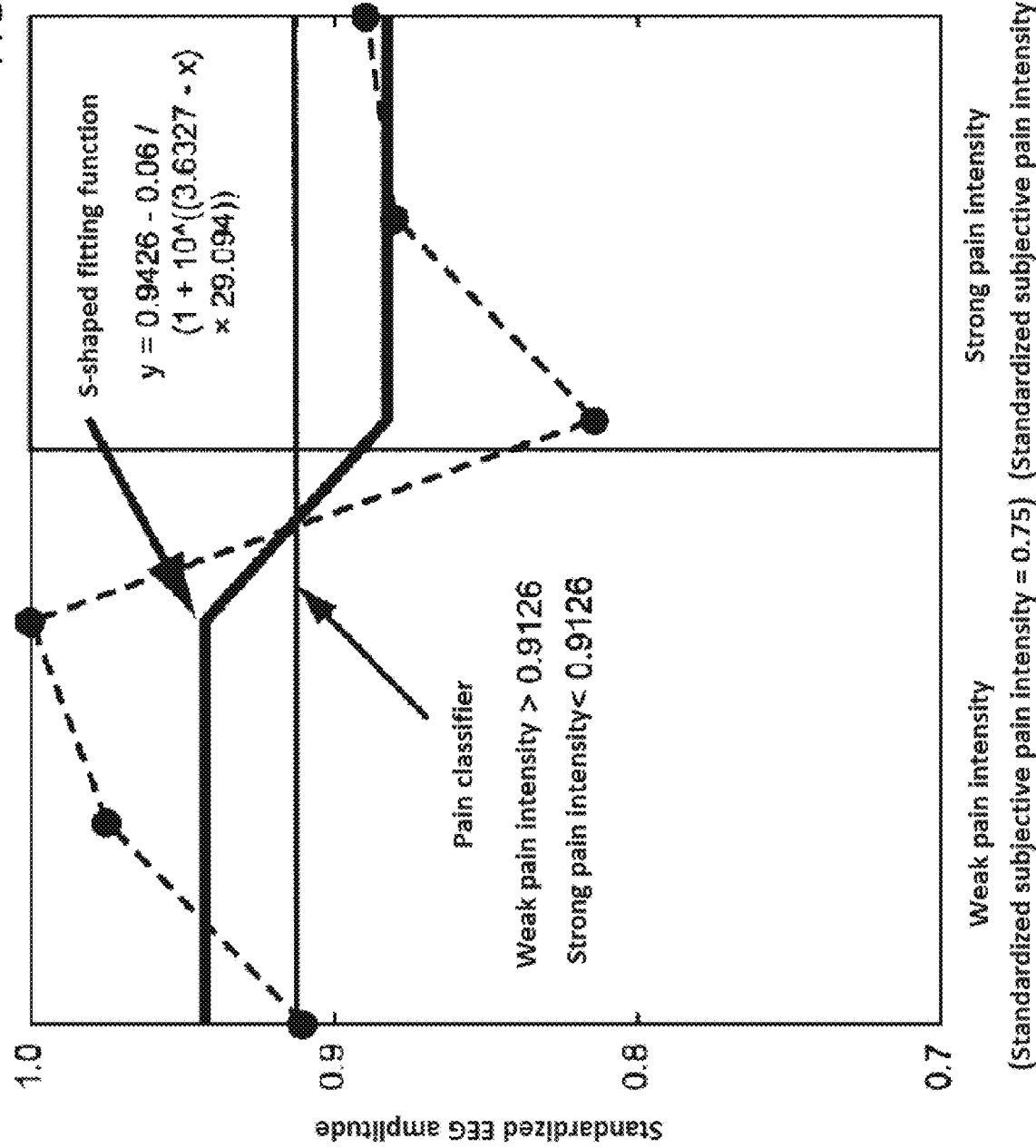
FIG. 19 shows a sigmoid fitting function and pain classification in a reference electrical pain paradigm.
Figure 20:
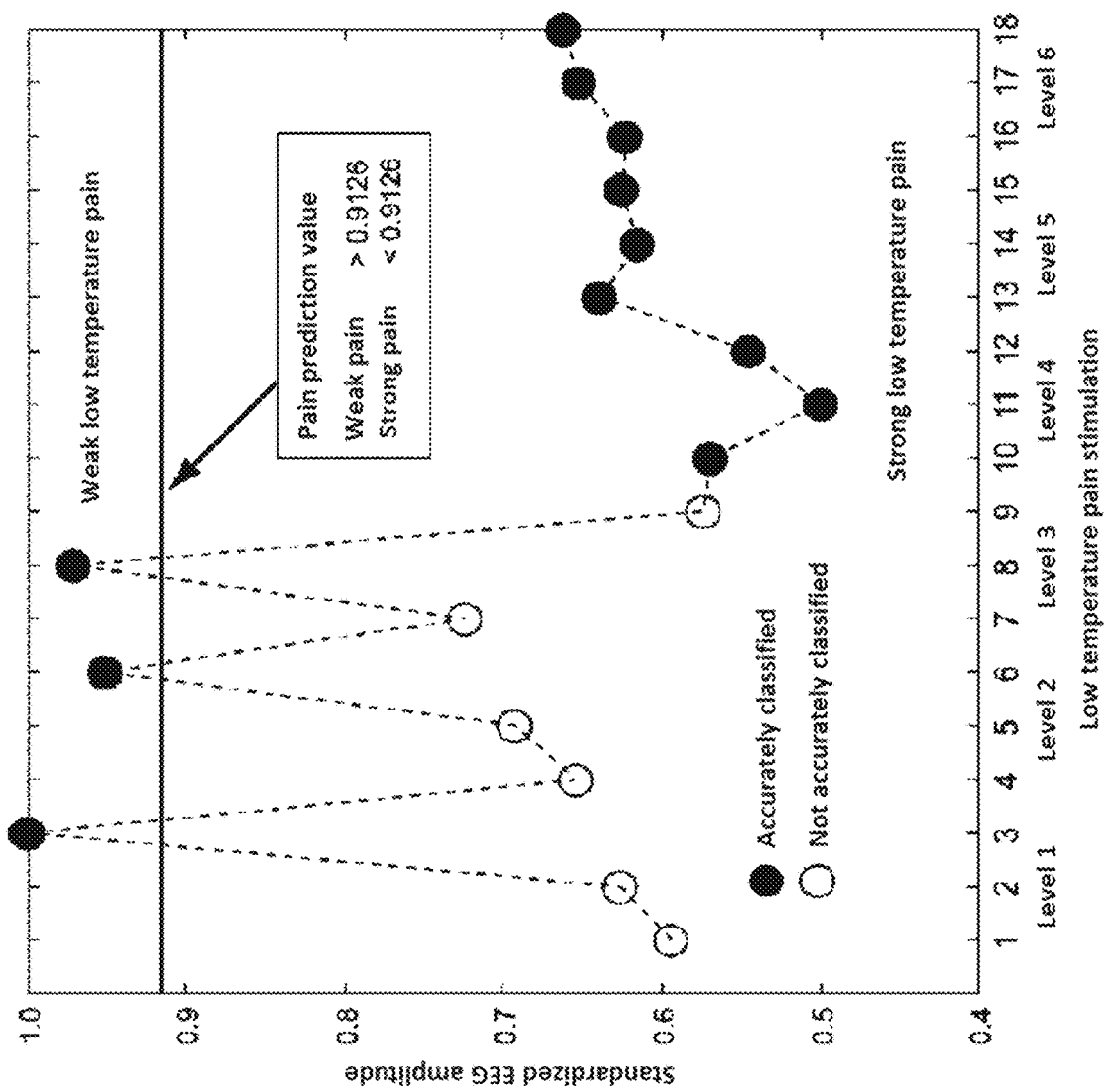
FIG. 20 shows a prediction of a low temperature pain intensity based on a reference pain prediction.
Figure 21:
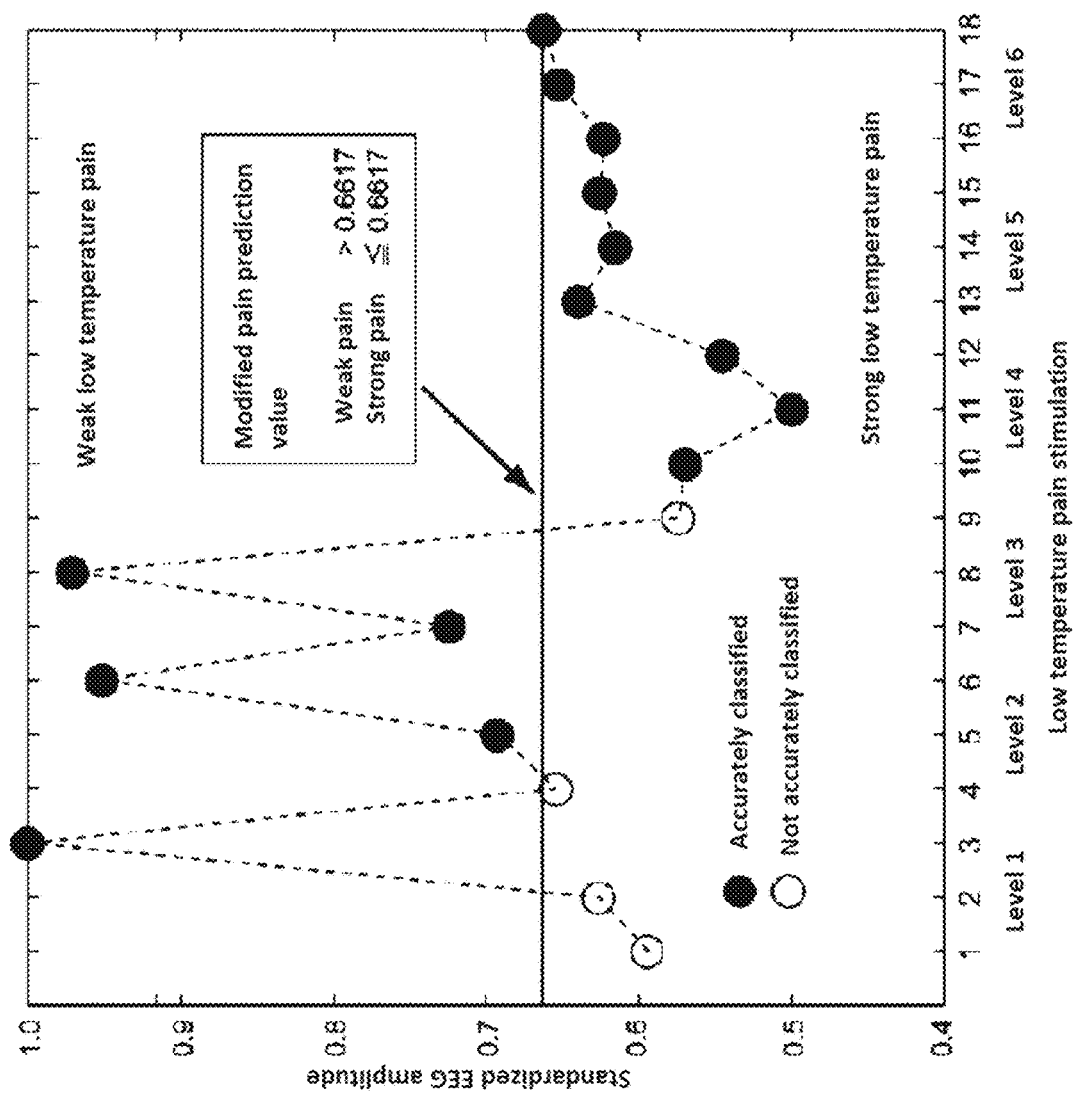
FIG. 21 shows calibration of a classification threshold related to pain prediction.

A pain classifier based on a sigmoid function can also be used as a pain prediction value for other pain. First, stimulation of weak reference electrical stimulation level 3 and strong reference electrical stimulation level 3 was inflicted three times each on one participant. The mean absolute amplitude for each stimulation was calculated over a duration of 5 seconds after stimulation and standardized with the maximum amplitude in 6 levels of data samples. Six levels of data were linearly arranged and fitted to a sigmoid function as shown in FIG. 19. The inventor obtained a pain classifier with a threshold value of 0.9126 based on such a fitting function. This pain classifier was used to predict a low temperature pain intensity level for the same participant using a different type of low temperature simulation data in FIG. 16A. Each stimulation was independently averaged over a duration of 30 seconds and standardized, and then 18 mean value data were obtained. These data were arranged linearly from the weakest level (level 1) to the strongest level (level 6) and classified with a pain classifier having a threshold value of 0.9126. Three higher levels were accurately predictable based on reference pain classification or prediction value (FIG. 20). However, a relatively large error was observed in the three lower low temperature pain levels. In fact, use of this pain prediction instrument resulted in 60% classification error, suggesting that calibration of the classification threshold value was required. In this regard, the classification threshold value was corrected by the following method. The standardized EEG amplitude maximum value for strong pain tests was clearly established to lower the threshold value to 0.661 (FIG. 21). Such a linear calibration method improved classification errors from 60% to 44%.

It was therefore demonstrated that a pain classifier can more accurately classify and estimate pain by calibration.

Example 2

Example 2 demonstrated that a change in brain activity exhibits a sigmoid function form via an inflection point in accordance with a change in pain levels by using a different analysis method.

The following analysis was conducted in this Example. The sample size was 14.

Various types of stimulation were inflicted in accordance with the description in Example 1 with the following notable modifications.

*The mean of EEG amplitude absolute value for 30 seconds after exposure to stimulation of level 1 (for three runs) and the standard error were found to find the threshold value of level 1 (mean−standard error×2). Since Example has revealed that a monotonous decreasing pattern is exhibited by an increase in pain levels, a baseline was determined to be increasing pain levels when lower than the level 1 threshold value.

*For each level from levels 2 to 6, the frequency of EEG amplitude absolute value being less than the level 1 threshold value (number of time points) was calculated.

*The frequency of points below the level 1 threshold value in level 2 and other levels was calculated for each individual, and the mean value was compared by a t-test.

In other words, it is demonstrated that a pain level is stronger for higher frequency of deviation from the level 1 threshold value, and the threshold value is effective as a pain classifier for higher degree of deviation.

(Results)

Figure 22:
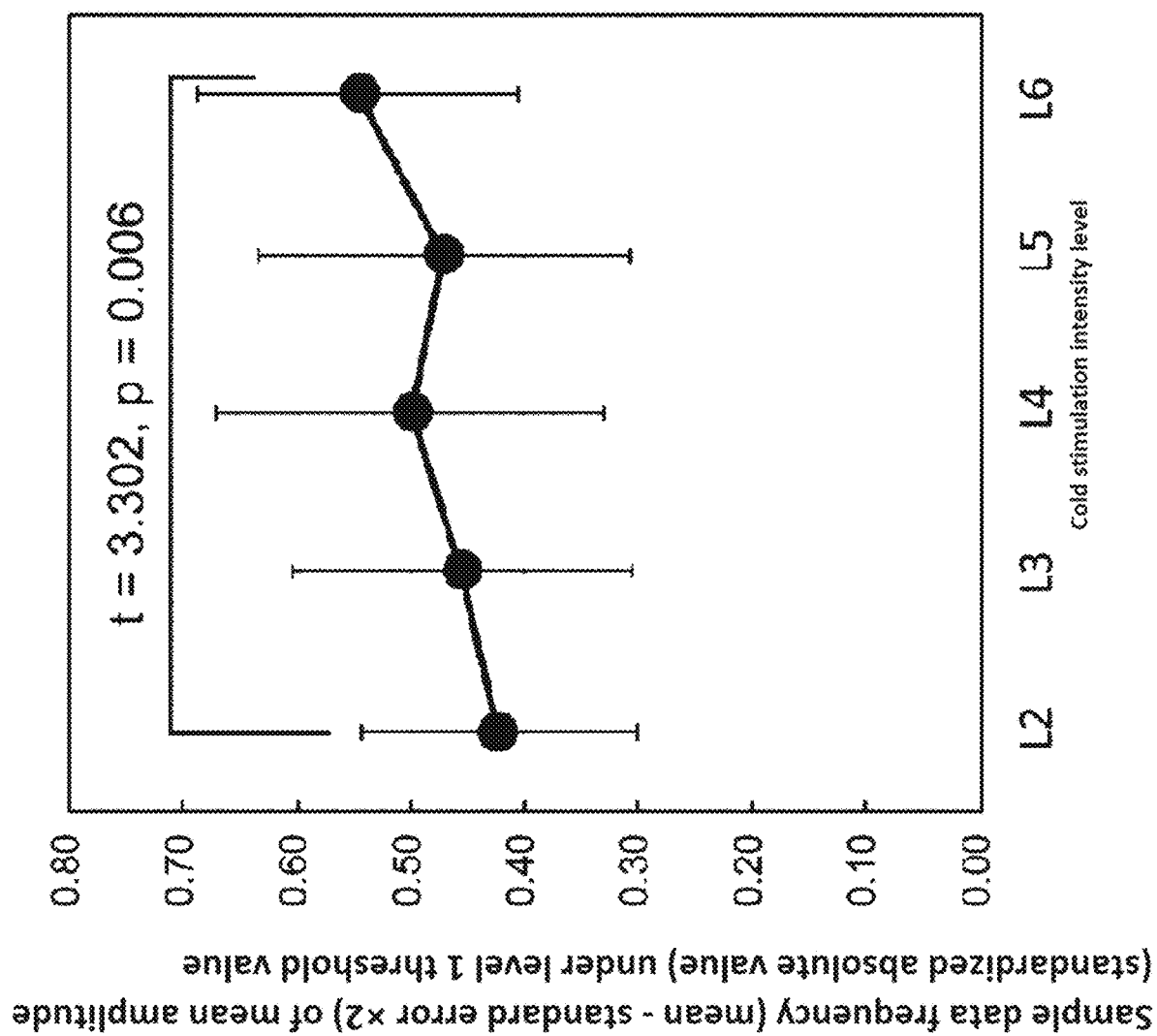
FIG. 22 shows another example related to branching (sigmoid function pattern) in the change in the amount of brain activity between the strong pain level and another pain level.

While a higher level does not always mean a higher frequency in all subjects, pain level 2 and the highest level 6 have been proven to have a statistically significant difference as shown in FIG. 22. This is data demonstrating that there is a difference, i.e., gap, via an inflection point between "unbearably painful" level 6 and other "not painful" or "weaker pain" levels due to the present invention.

Example 3: Diversity in Linearity of the Modulation Range in Sigmoidal Pain Function The objective of Example 3 was to study how the linear region of a sigmoidal pain function (modulation range) changes among individuals due to a pattern of pain stimulation. The focus was especially on the change in slope as in FIG. 28A and the change in amplitude in the modulation region as in FIG. 28B.

(Method) One healthy male was inflicted with 1) three consecutive or 10 consecutive electrical stimulation of 0.25 mA and 2) 10 consecutive electrical stimulation of 0.25 mA and 0.75 mA. After the electrical stimulation, the subject was asked to subjectively evaluate the unpleasantness of stimulation in levels of 1 to 10.

(Results) As shown in FIG. 28C, when the number of consecutive electrical stimulation of 0.25 mA was changed, the point of reaching the maximum value of unpleasantness moved up from 12 to 10 applications of stimulation, and the maximum value of unpleasantness also increased, so that the slope changed. Meanwhile, when the electrical stimulation intensity was changed, the unpleasantness score at the start of modulation doubled, so that the slope slightly decreased. In other words, this indicates that if the pain intensity is high from the beginning, a change is pain sensitivity is low and difficult to detect. This is an example showing that linearity in the modulation region in a sigmoidal pain function is effective in identifying pain sensitivity of individuals.

(Application Example)

As shown in the above Examples, a pain stimulation presentation method (i.e., reference stimulation presentation method from the stimulation apparatus unit 5900) can be changed and a linearity changing pattern in the modulation region of a sigmoid function can be identified for subjects to identify pain sensitivity of individuals and to create and correct the determination algorithm installed in the pain determination/estimation apparatus unit 5300.

Note

As disclosed above, the present invention has been exemplified by the use of its preferred embodiments. However, it is understood that the scope of the present invention should be interpreted based solely on the Claims. It is also understood that any patent, any patent application, and any other references cited herein should be incorporated herein by reference in the same manner as the contents are specifically described herein. The present application claims priority to Japanese Patent Application No. 2016-162195 filed on Aug. 22, 2016 and Japanese Patent Application No. 2017-133424 filed on Jul. 7, 2017 with the Japan Patent Office. The entire content thereof is incorporated herein by reference.

INDUSTRIAL APPLICABILITY

The present invention can be utilized as a pain estimation apparatus for estimating a magnitude of pain based on a brainwave of an object being estimated. The present invention can also precisely classify pain, estimate pain without inflicting strong pain, and finely diagnose and treat pain.

REFERENCE SIGNS LIST

99: object being estimated
100, 200: pain estimation system
110, 210: pain estimation apparatus
111, 211: measurement unit
112, 212: estimation unit
120: brainwave meter
213: identification unit
230: stimulation apparatus
1000: reference stimulation unit
1500: subject
2000: brainwave data obtaining unit
2500: brainwave meter
3000: pain classifier generation unit
4000: pain classification unit
5099: object
5100: pain classifier generation system
5150: pain estimation/classification system
5200: brainwave measurement unit
5220: brainwave meter
5250: brainwave recording sensor
5270: brainwave amplification unit
5300: pain determination/estimation apparatus unit
5400: brainwave signal processing unit
5500: brainwave characteristic amount extraction unit
5600: pain determination/estimation unit
5700: pain determination correction unit
5800: pain level visualization unit
5900: stimulation apparatus unit
5920: reference stimulation presentation terminal
5940: reference stimulation generation unit
5960: reference stimulation level visualization unit

The invention claimed is:

1. An apparatus for generating a pain classifier for classifying pain of an object being estimated based on a brainwave of the object being estimated, comprising:
   a plurality of electrodes including:
      a plurality of brainwave measurement electrodes configured to be placed on the object's scalp;
      a reference electrode configured to be attached to the subject's earlobe; and
      a front-most electrode configured to receive an eye movement activity signal;
   a brainwave recording sensor configured to record data sampled from signals transmitted from the plurality of brainwave measurement electrodes;
   a stimulation apparatus configured to apply stimuli to the object; and
   a processor, the processor configured to:
      A) stimulate the object being estimated with a plurality of levels of thermal stimulation intensities by using the stimulation apparatus;
      B) obtain, by selecting brainwave electrodes from the plurality of brainwave measurement electrodes and using the brainwave recording sensor, continuous brainwave data or analysis data thereof of the object being estimated corresponding to the plurality of levels of thermal stimulation intensities by removing artifact of eye movement activity;
      C) convert the continuous brainwave data to a first predetermined number of epoch data by removing artifact of eye movement activity, the first predetermined number of epoch data including a second predetermined number of epoch data in each of the levels of thermal stimulation intensities, each of the epoch data having a first predetermined duration after start of application of each of the levels of thermal stimulation intensities;

D) correct each of the epoch data by a baseline correction using an epoch reference value calculated from a second predetermined duration before the start of the application of the stimulation to average the second predetermined number of the absolute value of the corrected epoch data for each of the levels of thermal stimulation intensities; and E) perform plotting, and fitting to a specific pain function, with a horizontal axis indicating the plurality of levels of thermal stimulation intensities or subjective pain sensation levels corresponding to the plurality of levels of thermal stimulation intensities and with a vertical axis indicating the averaged absolute value of the corrected epoch data to obtain the fitted specific pain function specific to the object being estimated, and identifying the pain classifier for separating pain levels to at least two classes based on the specific pain function, wherein the specific pain function comprises a decreasing sigmoid function.

2. A method for generating a pain classifier for classifying pain of an object being estimated based on a brainwave of the object being estimated, comprising:

providing a brainwave recording sensor and a computer, wherein the brainwave recording sensor is configured to record data sampled from signals transmitted from a plurality of electrodes, the plurality of electrodes including a plurality of brainwave measurement electrodes configured to be placed on the object's scalp, and the computer receives the data from the brainwave recording sensor and includes a processor;

stimulating the object being estimated with a plurality of levels of thermal stimulation intensities;

obtaining, using the brainwave recording sensor, continuous brainwave data or analysis data thereof of the object being estimated corresponding to the plurality of levels of thermal stimulation intensities by removing artifact of eye movement activity;

converting the continuous brainwave data to a first predetermined number of epoch data by removing artifact of eye movement activity, the first predetermined number of epoch data including a second predetermined number of epoch data in each of the levels of thermal stimulation intensities, each of the epoch data having a first predetermined duration after start of application of each of the levels of thermal stimulation intensities;

correcting each of the epoch data by a baseline correction using an epoch reference value calculated from a second predetermined duration before the start of the application of the stimulation to average the second predetermined number of the absolute value of the corrected epoch data for each of the levels of thermal stimulation intensities; and performing, by the processor, plotting, and fitting to a specific pain function, with a horizontal axis indicating the plurality of levels of thermal stimulation intensities and with a vertical axis indicating the averaged absolute value of the corrected epoch data to obtain the fitted specific pain function specific to the object being estimated, and identifying the pain classifier for separating pain levels to at least two classes based on the specific pain function, wherein the specific pain function comprises a decreasing sigmoid function.

3. A system for classifying pain of an object being estimated based on a brainwave of the object by using a classifier, comprising:

a brainwave recording sensor, wherein the brainwave recording sensor is configured to record data sampled from signals transmitted from a plurality of electrodes including brainwave measurement electrodes configured to be placed on the object's scalp;

a first computer including a first processor, the first processor configured to:
obtain, by using the brainwave recording sensor, continuous brainwave data from the object; and
perform, based on the obtained continuous brainwave data, a process as a classifier for classifying pain of the object being estimated based on the continuous brainwave of the object, wherein the classifier is generated by a machine learning process; and a second computer including a second processor, the second processor configured to execute the machine learning process, the machine learning process including:
stimulating the object being estimated with a plurality of levels of thermal stimulation intensities and receiving the data of the object from the brainwave recording sensor;
obtaining, using the brainwave recording sensor, brainwave data or analysis data thereof of the object being estimated corresponding to the plurality of levels of thermal stimulation intensities by removing artifact of eye movement activity;
converting the continuous brainwave data to a first predetermined number of epoch data by removing artifact of eye movement activity, the first predetermined number of epoch data including a second predetermined number of epoch data in each of the levels of thermal stimulation intensities, each of the epoch data having a first predetermined duration after start of application of each of the levels of thermal stimulation intensities;
correcting each of the epoch data by a baseline correction using an epoch reference value calculated from a second predetermined duration before the start of the application of the stimulation to average the second predetermined number of the absolute value of the corrected epoch data for each of the levels of thermal stimulation intensities; and
performing, by the second processor, plotting, and fitting to a specific pain function, the plurality of levels of thermal stimulation intensities or subjective pain sensation levels corresponding to the plurality of levels of thermal stimulation intensities and the brainwave data or analysis data thereof to obtain the specific pain function specific to the object being estimated, and identifying the classifier for separating pain levels to at least two based on the specific pain function, wherein the specific pain function comprises a decreasing sigmoid function.

4. A recording medium for storing a program for implementing a method of generating a pain classifier for classifying pain of an object being estimated based on a brainwave of the object being estimated on a computer, the computer including a processor and an interface to communicate a brainwave recording sensor, wherein the brainwave recording sensor is configured to record data sampled from signals transmitted from a plurality of electrodes including brainwave measurement electrodes configured to be placed on the object's scalp, the method comprising:
stimulating the object being estimated with a plurality of levels of thermal stimulation intensities and receiving the data of the object from the brainwave recording sensor;
obtaining, using the brainwave recording sensor, continuous brainwave data of the object being estimated corresponding to the plurality of levels of thermal stimulation intensities by removing artifact of eye movement activity;
converting the continuous brainwave data to a first predetermined number of epoch data by removing artifact of eye movement activity, the first predetermined number of epoch data including a second predetermined number of epoch data in each of the levels of thermal stimulation intensities, each of the epoch data having a first predetermined duration after start of application of each of the levels of thermal stimulation intensities;
correcting each of the epoch data by a baseline correction using an epoch reference value calculated from a second predetermined duration before the start of the application of the stimulation to average the second predetermined number of the absolute value of the corrected epoch data for each of the levels of thermal stimulation intensities; and
performing, by the processor, plotting, and fitting to a specific pain function, with a horizontal axis indicating the plurality of levels of thermal stimulation intensities or subjective pain sensation levels corresponding to the plurality of levels of thermal stimulation intensities and with a vertical axis indicating the averaged absolute value of the corrected epoch data to obtain the specific pain function specific to the object being estimated, and identifying the pain classifier for separating pain levels to at least two classes based on the specific pain function, wherein the specific pain function comprises a decreasing sigmoid function.

* * * * *